(12) United States Patent
Fahey et al.

(10) Patent No.: US 9,149,386 B2
(45) Date of Patent: Oct. 6, 2015

(54) DEVICES AND SYSTEMS FOR STIMULATION OF TISSUES

(71) Applicant: Niveus Medical, Inc., Redwood City, CA (US)

(72) Inventors: Brian J. Fahey, Palo Alto, CA (US); Zachary J. Malchano, San Francisco, CA (US); Timothy Machold, Moss Beach, CA (US); Curtis Tom, San Mateo, CA (US)

(73) Assignee: NIVEUS MEDICAL, INC., Redwood City, CA (US)

( * ) Notice: Subject to any disclaimer, the term of this patent is extended or adjusted under 35 U.S.C. 154(b) by 100 days.

(21) Appl. No.: 13/926,827

(22) Filed: Jun. 25, 2013

(65) Prior Publication Data

US 2014/0005759 A1    Jan. 2, 2014

Related U.S. Application Data

(60) Continuation-in-part of application No. 13/568,859, filed on Aug. 7, 2012, now Pat. No. 8,676,332, which is a division of application No. 12/710,243, filed on Feb. 22, 2010, now Pat. No. 8,433,403.

(60) Provisional application No. 61/208,119, filed on Feb. 20, 2009, provisional application No. 61/230,587, filed on Jul. 31, 2009, provisional application No. 61/664,064, filed on Jun. 25, 2012.

(51) Int. Cl.
*A61N 1/00* (2006.01)
*A61F 7/10* (2006.01)
*A61N 1/36* (2006.01)
(Continued)

(52) U.S. Cl.
CPC ............... *A61F 7/10* (2013.01); *A61N 1/0452* (2013.01); *A61N 1/0492* (2013.01); *A61N 1/36003* (2013.01); *A61B 5/01* (2013.01); *A61B 5/04001* (2013.01); *A61B 5/4836* (2013.01); *A61F 7/03* (2013.01); *A61F 2007/0056* (2013.01); *A61F 2007/0075* (2013.01); *A61F 2007/0276* (2013.01)

(58) Field of Classification Search
CPC ............. A61N 1/36003; A61N 1/0452; A61B 2018/00791
USPC .................................................. 607/99, 48, 3
See application file for complete search history.

(56) References Cited

U.S. PATENT DOCUMENTS 4,108,146 A    8/1978   Golden
4,390,023 A    6/1983   Rise
(Continued)

FOREIGN PATENT DOCUMENTS

FR          2596654 A       10/1987
JP          2001-025510      1/2001
(Continued)

OTHER PUBLICATIONS

Fahey; U.S. Appl. No. 14/070,210 entitled "Synergistic Muscle Activation Device," filed Nov. 1, 2013.
(Continued)

*Primary Examiner* — Christopher D Koharski
*Assistant Examiner* — Philip Edwards
(74) *Attorney, Agent, or Firm* — Shay Glenn LLP

(57) ABSTRACT

NMES systems and methods for stimulating muscle tissue, and in some embodiments deep muscle tissue. The impedance near the surface of the skin is controllably increased to increase the percentage of energy delivered to a subject that stimulates muscle tissue.

16 Claims, 25 Drawing Sheets

(51) Int. Cl.
*A61N 1/04* (2006.01)
*A61F 7/03* (2006.01)
*A61F 7/00* (2006.01)
*A61F 7/02* (2006.01)
*A61B 5/01* (2006.01)
*A61B 5/04* (2006.01)
*A61B 5/00* (2006.01)

(56) References Cited

U.S. PATENT DOCUMENTS

| | | | |
|---|---|---|---|
| 4,480,830 | A | 11/1984 | Petrofsky et al. |
| 4,580,569 | A | 4/1986 | Petrofsky |
| 4,619,266 | A | 10/1986 | Hodgson |
| 4,736,752 | A | 4/1988 | Munck et al. |
| 4,805,636 | A | 2/1989 | Barry et al. |
| 4,811,742 | A | 3/1989 | Hassel et al. |
| 4,838,272 | A | 6/1989 | Lieber |
| 4,867,166 | A | 9/1989 | Axelgaard et al. |
| 4,962,761 | A | 10/1990 | Golden |
| 4,969,468 | A | 11/1990 | Byers et al. |
| 5,010,896 | A | 4/1991 | Westbrook |
| 5,016,635 | A | 5/1991 | Graupe |
| 5,070,873 | A | 12/1991 | Graupe et al. |
| 5,097,828 | A | 3/1992 | Deutsch |
| 5,314,423 | A | 5/1994 | Seney |
| 5,336,255 | A | 8/1994 | Kanare et al. |
| 5,397,338 | A | 3/1995 | Grey et al. |
| 5,507,788 | A | 4/1996 | Lieber |
| 5,549,656 | A | 8/1996 | Reiss |
| 5,674,262 | A | 10/1997 | Tumey |
| 5,702,323 | A | 12/1997 | Poulton |
| 5,702,429 | A | 12/1997 | King |
| 5,843,152 | A | 12/1998 | Tu et al. |
| 5,871,526 | A | 2/1999 | Gibbs et al. |
| 5,902,328 | A | 5/1999 | LaFontaine et al. |
| 6,216,704 | B1 | 4/2001 | Ingle et al. |
| 6,266,558 | B1 | 7/2001 | Gozani et al. |
| 6,301,500 | B1 | 10/2001 | Van Herk et al. |
| 6,324,432 | B1 | 11/2001 | Rigaux et al. |
| 6,341,237 | B1 | 1/2002 | Hurtado |
| 6,350,276 | B1 | 2/2002 | Knowlton |
| 6,480,731 | B1 | 11/2002 | DeLuca et al. |
| 6,505,078 | B1 | 1/2003 | King et al. |
| 6,567,696 | B2 | 5/2003 | Voznesensky et al. |
| 6,829,510 | B2 | 12/2004 | Nathan et al. |
| 6,840,955 | B2 | 1/2005 | Ein |
| 6,944,503 | B2 | 9/2005 | Crowe et al. |
| 7,146,220 | B2 | 12/2006 | Dar et al. |
| 7,172,564 | B2 | 2/2007 | Bosco |
| 7,204,832 | B2 | 4/2007 | Altshuler et al. |
| 7,221,980 | B2 | 5/2007 | Kotlik et al. |
| 7,236,832 | B2 | 6/2007 | Hemmerling et al. |
| 7,257,448 | B2 | 8/2007 | Crowe et al. |
| 7,276,058 | B2 | 10/2007 | Altshuler et al. |
| 7,473,251 | B2 | 1/2009 | Knowlton et al. |
| 7,483,738 | B2 | 1/2009 | Tamarkin et al. |
| 7,499,746 | B2 | 3/2009 | Buhlmann et al. |
| 8,216,218 | B2 | 7/2012 | Burns et al. |
| 8,265,763 | B2 | 9/2012 | Fahey |
| 8,285,381 | B2 | 10/2012 | Fahey |
| 8,433,403 | B2 | 4/2013 | Fahey |
| 2002/0049483 | A1 | 4/2002 | Knowlton |
| 2002/0143365 | A1 | 10/2002 | Herbst |
| 2002/0151951 | A1 | 10/2002 | Axelgaard et al. |
| 2003/0229385 | A1 | 12/2003 | Elkins |
| 2004/0044384 | A1 | 3/2004 | Leber et al. |
| 2004/0173220 | A1 | 9/2004 | Harry et al. |
| 2004/0254624 | A1 | 12/2004 | Johnson |
| 2005/0288730 | A1 | 12/2005 | Deem et al. |
| 2006/0142816 | A1 | 6/2006 | Fruitman et al. |
| 2007/0106343 | A1 | 5/2007 | Monogue et al. |
| 2007/0178579 | A1 | 8/2007 | Brown et al. |
| 2007/0203435 | A1 | 8/2007 | Novak |
| 2008/0161883 | A1 | 7/2008 | Conor |
| 2008/0195010 | A1 | 8/2008 | Lai et al. |
| 2008/0208288 | A1 | 8/2008 | Gesotti |
| 2009/0012436 | A1 | 1/2009 | Lanfermann et al. |
| 2010/0081963 | A1 | 4/2010 | Gilhuly |
| 2011/0082517 | A1 | 4/2011 | Brezel et al. |
| 2011/0093036 | A1 | 4/2011 | Mashiach |
| 2011/0112605 | A1 | 5/2011 | Fahey |
| 2011/0152972 | A1 | 6/2011 | Doerr et al. |
| 2012/0226330 | A1 | 9/2012 | Kolen et al. |
| 2012/0277818 | A1 | 11/2012 | Stancer et al. |
| 2012/0303076 | A1 | 11/2012 | Fahey |
| 2013/0030277 | A1 | 1/2013 | Fahey |

FOREIGN PATENT DOCUMENTS

| | | |
|---|---|---|
| JP | 2002-052000 | 2/2002 |
| JP | 2006510431 | 3/2006 |
| KR | 10-866543 B | 11/2008 |
| WO | WO 01/52759 A1 | 7/2001 |
| WO | WO 03/086217 A1 | 10/2003 |
| WO | WO 2004/089185 A2 | 10/2004 |
| WO | WO 2004/098703 A2 | 11/2004 |
| WO | WO 2005/075018 A1 | 8/2005 |
| WO | WO 2005/105203 A1 | 11/2005 |
| WO | WO 2007/017778 A2 | 2/2007 |
| WO | WO 2007/041540 A1 | 4/2007 |
| WO | WO 2007/046886 A1 | 4/2007 |
| WO | WO 2008/032282 A2 | 3/2008 |
| WO | WO 2008/034607 A1 | 3/2008 |
| WO | WO 2008/075250 A1 | 6/2008 |
| WO | WO 2008/116232 A1 | 9/2008 |
| WO | WO 2009/009661 A1 | 1/2009 |

OTHER PUBLICATIONS

Baker et al.; Effects of waveform on comfort during neuromuscular electrical stimulation; Clin Ortho Res; vol. 233; pp. 75-85; Aug. 1988.

Bennie et al.; Toward the optimal waveform for electrical stimulation of human muscle; Eur J Appl Physiol; vol. 88; pp. 13-19; Nov. 2002.

Covidien; Principles of Electrosurgery (white paper); p. 3; accessed from http://www.asitorg/assets/documents/Prinicpals_in_electrosurgery.pdf on Dec. 12, 2012, 4 pages.

Lacey et al.; Reductions in the amount of time spent in direct patient care by staff nurses in North Carolina; North Carolina Center for Nursing; Aug. 2002.

Lyons et al.; An investigation of the effect of electrode size and electrode location on comfort during stimulation of the gastrocnemius muscle; Medical Engineering & Physics; vol. 26; pp. 873-878; Dec. 2004.

Miklavcic et al.; Electrical Properties of Tissues; Wiley Encyclopedia of Biomedical Engineering; (year of publication is sufficiently earlier than the effective U.S. filed and any foreign priority date) 2006.

Morris, Peter E.; Moving our critically ill patients: mobility barriers and benefits; Critical Care Clinics; vol. 23; pp. 1-20; Jan. 2007.

Petrofsky et al.; Estimation of the distribution of intramuscular current during electrical stimulation of the quadriceps muscle; Eur J Appl Physiol; vol. 103(3); pp. 265-273; Jun. 2008.

Prausnitz, Mark R.; The effects of electrical current applied to skin: a review for transdermal drug delivery; Advanced Drug Delivery Reviews; vol. 18; pp. 395-425; Feb. 8, 1996.

Rafolt et al.; Dynamic force responses in electrically stimulated triceps surae muscles: effects of fatigue and temperature; Artificial Organs; vol. 23; No. 5; pp. 436-439; May 1999.

Solomon et al.; The effects of TENS, heat, and cold on the pain thresholds induced by mechanical pressure in healthy volunteers; Neuromodulation; vol. 6; No. 2; pp. 102-107; Apr. 2003.

Stecker et al.; Mechanisms of electrode induced injury. Part 1: theory; Am. J. END Tech.; vol. 46; pp. 315-342; Dec. 2006.

Snyder-Mackler et al.; Use of electrical stimulation to enhance recovery of quadriceps femoris muscle force production in patients following anterior cruciate ligament reconstruction; Phys Ther.; 74(10):901-7; Oct. 1994.

Suganuma et al., Measurement of tension of tendon tissue based on electrical impedance; J. Ortho Science; vol. 9; pp. 302-309; (year of publication is sufficiently earlier than the effective U.S. filed and any foreign priority date) 2004.

(56) References Cited

OTHER PUBLICATIONS

Xodus Medical; Electrosurgery Frequency Spectrum; accessed from http://www.xodusmedical.com/Modules/Product/ProductTraining.aspx?Launch=Electrosurgical on Dec. 12, 2012; 1 page.

Zanotti et al.; Peripheral muscle strength training in bed-bound patients with COPD receiving mechanical ventilation: effect of electrical stimulation; Chest; vol. 124; No. 1; pp. 292-296; Jul. 2003.

Fahey; U.S. Appl. No. 14/532,595 entitled "Devices, systems, and methods for automated optimization of energy delivery," filed Nov. 4, 2014.

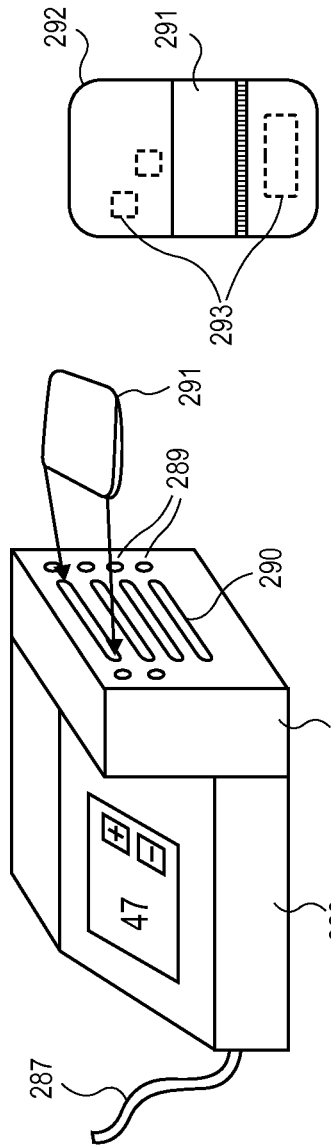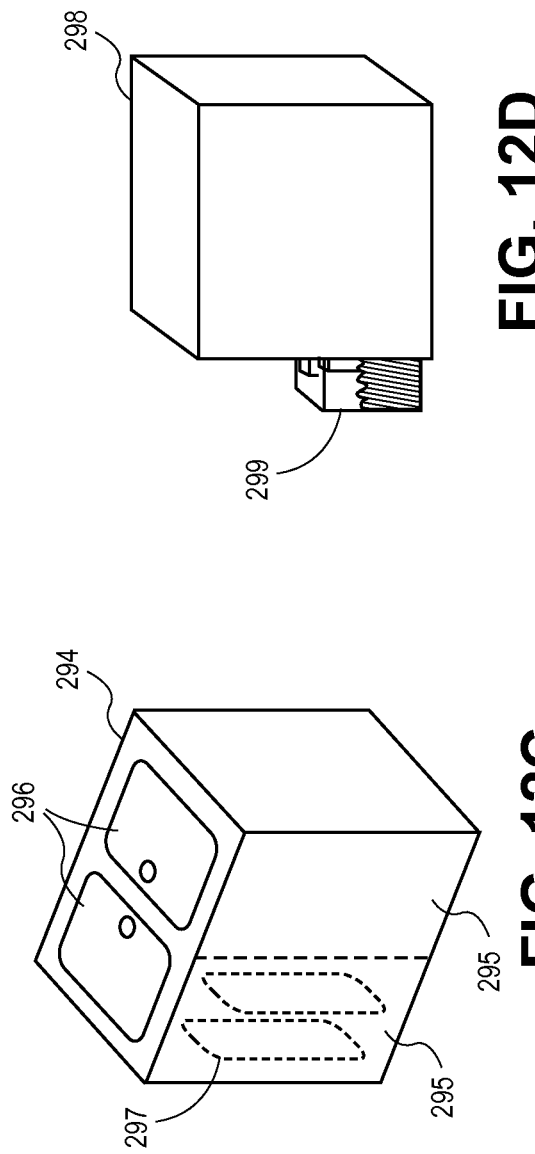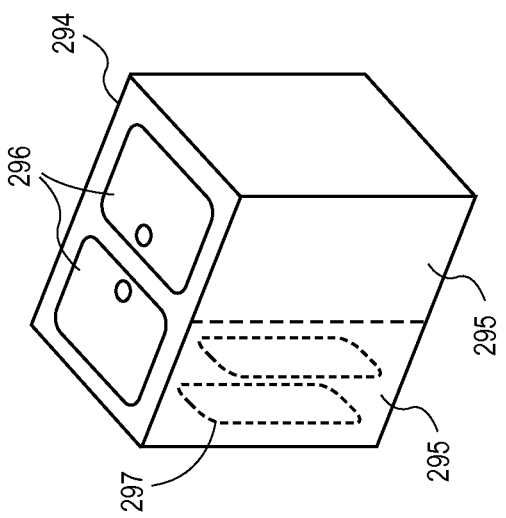

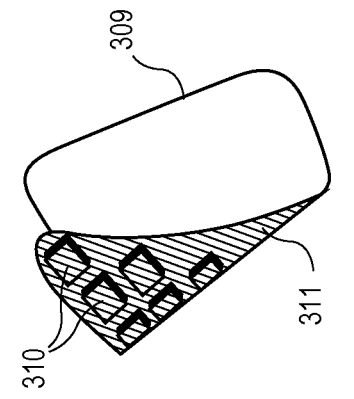
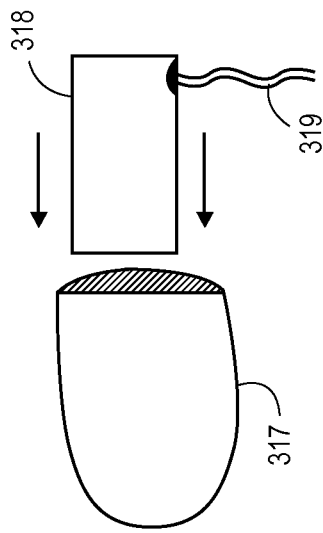
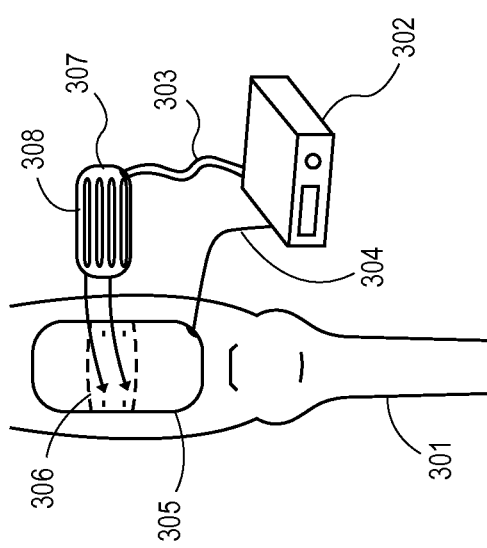
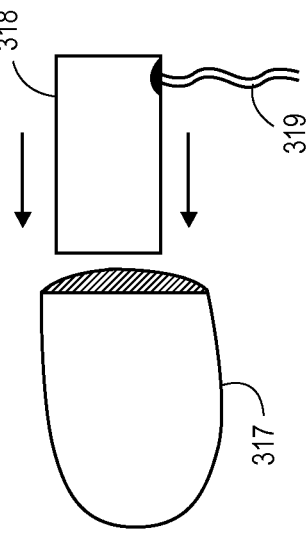
FIG. 15A
FIG. 15B
FIG. 15C
FIG. 15D

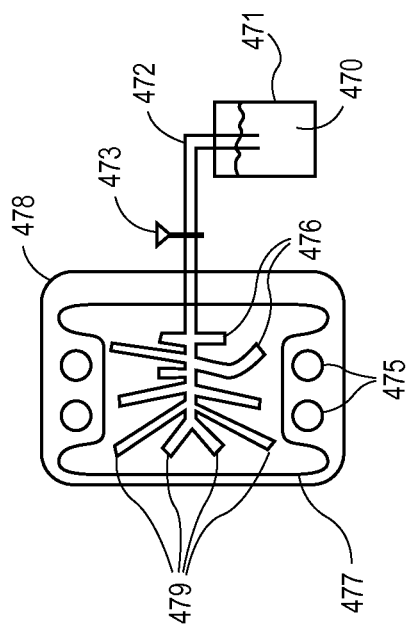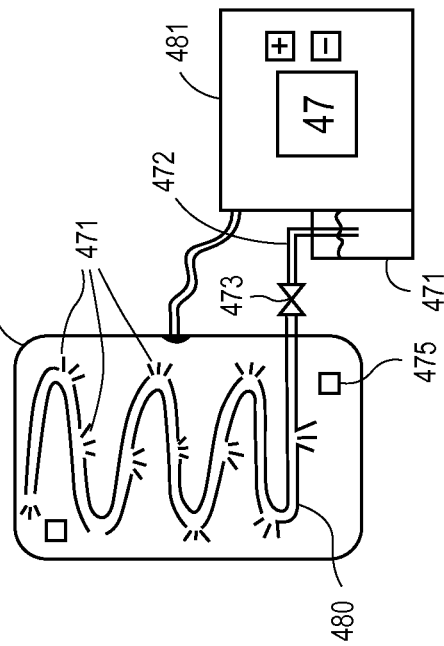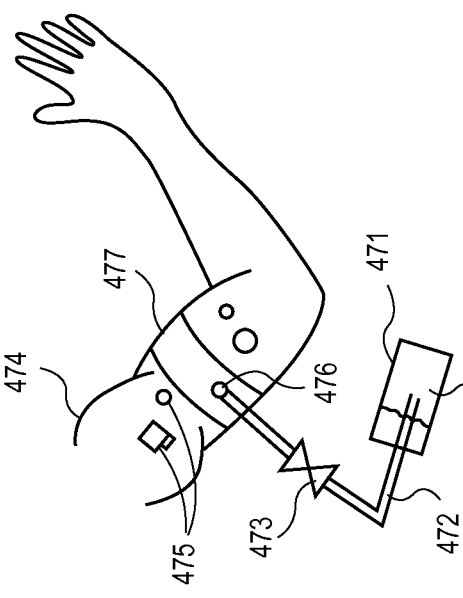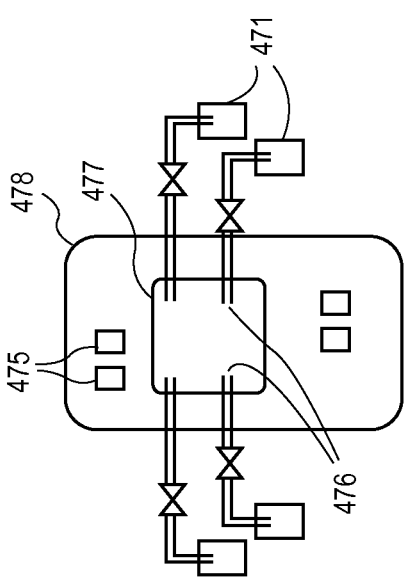
FIG. 16A
FIG. 16B
FIG. 16C
FIG. 16D

DEVICES AND SYSTEMS FOR STIMULATION OF TISSUES

CROSS-REFERENCE TO RELATED APPLICATIONS

This application is a continuation-in-part application of U.S. application Ser. No. 13/568,859, filed Aug. 7, 2012, now U.S. Pat. No. 8,676,332, which is a divisional application of U.S. application Ser. No. 12/710,243, filed Feb. 22, 2010, now U.S. Pat. No. 8,433,403, which claims the priority of U.S. Provisional Application Nos. 61/208,119, filed Feb. 20, 2009 and 61/230,587, filed Jul. 31, 2009. Each of the aforementioned applications is incorporated by reference herein in its entirety.

This application also claims the benefit of U.S. Provisional Application No. 61/664,064, filed Jun. 25, 2012, the disclosure of which is incorporated by reference herein in its entirety.

This application is related to the following copending patent applications: Application No. 61/260,324, filed Nov. 11, 2009; application Ser. No. 12/497,230, filed Jul. 2, 2009; Application No. 61/189,558, filed Aug. 19, 2008; application Ser. No. 12/548,155, filed Aug. 26, 2009; Application No. 61/190,602, filed Aug. 29, 2008; and Application No. 61/201,877, filed Dec. 15, 2008, all of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE DISCLOSURE

Neuromuscular electrical stimulation ("NMES"), which is also referred to as powered muscle stimulation, functional muscle stimulation, electrical muscle stimulation, is a known technology with many therapeutic uses, including pain relief, prevention or retardation of disuse atrophy, and improvement of local blood circulation. NMES is typically delivered as an intermittent and repeating series of short electrical pulses delivered transcutaneously by surface electrodes that are attached to a person's skin. The electrical pulses are delivered to muscle tissue and/or a muscle nerve to induce muscle contraction. The electrodes may be secured to the skin using straps, adhesives, or other mechanisms, and often contain a coupling layer composed of hydrogel that is capable of enhancing the efficiency of energy transfer from the electrode to the skin and underlying tissues.

A group of persons who could potentially show large benefit from NMES therapy are those who are immobilized or confined to bed rest. Periods of immobilization lead to muscle atrophy and weakness, and have severe effects on a person's physical capacity. Following immobilization, a previously active and functional person will typically require extensive physical therapy to reclaim their prior level of functionality. NMES may help these persons by preventing or retarding muscle atrophy during immobilization.

Critically ill patients comprise a subgroup of immobilized individuals. While virtually all of these patients are confined to bed rest, many are also suffering from conditions such as coma or are receiving interventions (such as mechanical ventilation) that generally require sedation and/or analgesia. Sedated or comatose patients are at a great risk for muscle atrophy because even simple voluntary movements (such as shifting arms/legs in bed or moving one's feet) are often not performed. Consequently, critically ill patients face long paths to recovery that are generally measured in months as opposed to days or weeks.

As part of the care for their acute illness, many critically ill patients receive UV fluids, antibiotics, and other interventions. One common side effect of these medical treatments in immobilized patients is the development of tissue edema. Generally speaking, tissue edema occurs as bodily fluids accumulate in 'the third space', or the region outside of both cells and vessels. Edema is often caused by microvasculature leakage, and typically results in tissue swelling. The presence of edema will generally negatively affect the performance of NMES, in many cases limiting the ability of the technology to adequately induce muscle contraction. This is particularly true when attempting to stimulate deep-lying muscles, such as the quadriceps, hamstrings, gluteals, rectus abdominus, transversus abdominus, internal and external obliques, pelvic floor, multifidus, erector spinae, longissimus thoracis, diaphragm, using non-invasive electrodes placed upon the surface of the skin.

There are several mechanisms of action by which tissue edema may affect NMES therapy. Tissue swelling may increase the distance between the surface of the skin and underlying muscle, resulting in a lower current density that reaches deep target muscles. Additionally, excessive ionic fluid in tissues may decrease the electrical impedance of tissue, particularly in superficial regions. The decrease in impedance in superficial regions can act to 'short-circuit' skin electrodes. The lower impedance path in superficial tissue regions can also act as a mechanism to reduce the current density in deeper muscle tissues. The latter of these mechanisms may be the dominant factor associated with decreased NMES performance in edematous patients. Although previous work in the medical literature has noted that certain types of electrical stimulation may prevent the onset of local edema after traumatic injury, these therapies have not been shown to prevent or reduce widespread edema in cases involving non-traumatic or multi-factorial medical conditions.

Existing NMES devices described in the prior art do not have features or compensation mechanisms to address tissue edema. Because of this, these devices provide highly variable performance in and are of limited utility amongst patients suffering from this condition. In many edematous patients, it is not possible to reliably stimulate the contraction of deep muscles using surface electrodes and energy levels that fall within regulatory and governing body (ex. the US FDA, ANSI, and IEC) standards. Although the use of higher energy levels may increase NMES efficacy, increasing the amplitude of delivered energy (and thus the current density in tissue), increases the risk of burns, nerve and/or muscle damage, and other potential complications (as detailed by Prausnitz *Advanced Drug Delivery Reviews* 18:395-425, 2006 and Stecker et al *Am J END Tech.*, 43:315-342, 2006, both of which are incorporated herein by reference). This is particularly true for the 'short circuit' condition, as large current densities will be present in superficial tissues. These factors and others limit the application of NMES therapy to edematous patients and to immobilized critically ill patients as a whole, a group that has been hypothesized to potentially benefit significantly from the therapy (Morris et al., *Critical Care Clinics*, 23:1-20, 2007—incorporated herein by reference). Delivery of safe and effective NMES therapy to immobilized critically ill patients would be facilitated by devices, systems, and methods designed to improve the performance of NMES, both in the presence of edema and in non-edematous persons and animals. Such devices, systems, and methods would allow for a larger patient cohort to receive the beneficial effects of a well-established medical therapy.

Short-duration superficial cooling may improve stimulation efficacy in patients both with and without peripheral tissue edema. For temperatures below 40° C., tissue impedance increases by about 2%/° C. (see Miklavcic et al., *Electrical Properties of Tissues*, Wiley Encyclopedia of Biomedical Engineering, 2006, incorporated herein by reference). Thus, when used with muscle stimulators operating in typical temperature ranges of use, surface cooling may increase the impedance of superficial tissues. Without wishing to be bound by any theory, it is believed that this may cause a greater percentage of delivered electrical energy to interact with deeper muscle tissues, facilitating more robust muscle contraction.

One application of reverse thermal gradients that has been described involves the combination of surface cooling with the targeted transcutaneous delivery of high energy radiofrequency (RF), optical, photo-acoustic, acoustic, infrared, electromagnetic, or other types of stimuli to tissues below the skin surface. Generally, these applications seek to significantly raise the temperature of tissues below the skin surface for the purposes of ablation, tissue (e.g., collagen) remodeling, or other dermatologic or therapeutic reasons. These applications seek to apply energy to target tissues non-invasively without raising temperatures in the skin and other superficial tissues to avoid damaging tissue not intended for treatment. The reverse thermal gradient assists this procedure by cooling superficial tissue without significantly cooling the deeper tissue that is intended to be treated by an increase in temperature. Accordingly, temperatures in superficial regions are kept below levels that would cause damage, even though a portion of the energy stimulus is absorbed in these regions.

A subset of thermal gradient applications described above use high amplitude RF or other forms of electromagnetic/electric energy to significantly raise temperatures in target tissue regions (e.g., hair follicles, collagen, etc.). To be effective, these treatments require temperatures in target regions of tissue to exceed about 43° C., with most applications requiring elevating tissue temperatures to about 60° C. or higher. Near these temperatures, moisture in cells and extracellular fluid is evaporated, resulting in increased tissue impedance with increased temperature. Reverse thermal gradients and surface cooling of tissues can assist energy delivery by forcing superficial tissue temperatures to remain only minimally elevated over normal body temperature, thus lowering the superficial tissue impedance (relative to the overheated tissues below), allowing for more energy to be delivered through the superficial tissue to the deeper target regions below.

For ablative, cosmetic, and other therapeutic procedures, muscle contraction is generally not induced by energy that is delivered to tissue. In virtually all cases, this is preferable, as muscle contraction in the region of desired treatment would complicate the intervention. For example, RF energy utilized by many devices is intentionally delivered in a frequency range, for example, about 100 to about 500 kHz, which is too high to elicit muscle contraction.

Additionally, in cosmetic, ablative, and therapeutic applications that use surface cooling to prevent skin burns, the reverse thermal gradient is applied at the anatomical location where energy transmits across the skin, or in larger regions that include the location at which energy is transmitted across the skin. These systems and methods utilizing the reverse thermal gradient are optimized for the energy amplitudes, frequency ranges, and temperature ranges that are common in these ablative, cosmetic, and therapeutic procedures. For muscle stimulators operating at relatively lower energy frequencies and amplitudes, with peak tissue temperatures near normal body temperature, there are drawbacks to lowering skin temperatures in the region where energy transmits across the skin. Doing so will significantly lower the efficiency of energy transfer into the body, markedly decrease the life span of surface stimulation electrodes, and decrease the overall effectiveness of the therapy.

Most muscle stimulators used in modern clinical settings are constant current (or voltage) stimulators, meaning that when tissue impedance increases, the stimulator device will increase the voltage (or current) amplitude of delivered energy (up to a predetermined limit) in an attempt to keep the electrical current (or voltage) delivered to a person constant. Without wishing to be bound by any theory, it is believed that this increase in voltage (or current) will increase energy loss and heat generation in skin electrodes. Although the risk of skin burns (generally a serious concern) may be partially reduced if the skin surface is pre-cooled, increased temperature of skin electrodes will degrade the performance of the electrodes. The most common modern-day skin electrodes used with NMES include a hydrogel coupling layer that serves as both an adhesive and a conductive (coupling) medium. These hydrogels may be composed of more than 50% water, and elevated temperatures will cause electrodes to dry prematurely, dramatically reducing reusability. This factor is particularly important in the ICU setting, where it is desirable to leave one set of electrodes in place for extended periods of time, as repeated placement and removal may cause skin trauma. Additionally, drying of hydrogel layers is a positive feedback phenomenon: as the conductive layer dries, skin/electrode impedance will increase further, causing even more heat generation at the skin, and potentially leading to the dangerous scenario of poor electrode contact due to reduced adhesive properties. This latter scenario is of serious concern, as electrodes with poor contact can cause skin burns very quickly, even when NMES is used in conjunction with surface cooling. Thus, devices employing surface cooling and temperature gradients used in the location of skin electrodes are accompanied by serious limitations if used in conjunction with NMES, since this technique raises tissue impedance in the skin electrode location. Specifically, surface cooling and temperature gradients in the location of the skin electrode(s) will typically not improve energy transfer efficiency to muscles, and may thus increase tissue impedance and decrease electrode performance in a manner that has little or no benefit for NMES.

Transcutaneous electrical nerve stimulators ("TENS") is another type of therapy that has used skin surface cooling combined with transcutaneous energy delivery. Specifically, this therapy has sought to harness the pain relief effects of hot and cold temperatures applied to the skin, and combine them with pain relief effects of nerve stimulation. Although TENS units are typically not operated at sufficient amplitude to cause muscle contraction, muscle stimulation with TENS units is theoretically possible. TENS therapy also applies temperature gradients in the anatomical locations where energy is transmitted through the skin, or over large spans of anatomical areas that include the locations where energy is transmitted through the skin. As described herein, doing so with electrical muscle stimulation therapies significantly lowers the efficiency of energy transfer into the body, markedly decreases the life span of surface stimulation electrodes, and decreases the overall effectiveness of the therapy.

Existing NMES devices and technologies that are disclosed in the prior art are not suitable for use in patients with peripheral tissue edema and/or with other challenging patients. This may be for performance reasons or for practicality reasons (i.e., technology may be viable but configured in an embodiment that is prohibitive to use in challenging environments, for example the hospital environment). Disclosed within are devices, systems, and methods for improving muscle stimulation efficacy that meet both performance and usability criteria to make them acceptable for broad application to subjects in a wide spectrum of environments.

SUMMARY OF THE DISCLOSURE

Detailed within are devices and systems for improved energy delivery to human or animal tissue. Though this disclosure uses the modality of NMES as an illustrative example, it will be obvious to those skilled in the art that with minor modifications the devices and systems described herein may be applied with utility to other energy-delivery therapies, such as TENS or RF or microwave ablative therapies, as well. An objective of the presently-disclosed devices and systems is to enhance the delivery of energy to target regions (in this example, energy delivered via NMES to target muscle and/or nervous tissues) using embodiments that are convenient and practical for use in many environments, including those where available operator time to deploy an intervention is limited. Preferable embodiments will incorporate mechanisms for superficial cooling of tissues in strategic regions in the vicinity of stimulation electrodes. The details of these preferable embodiments and implementations will provide advantages in terms of performance, cost, and convenience/usability over technologies described by the prior art. It should be appreciated that different aspects of the invention can be appreciated individually, collectively, or in combination with each other.

One aspect of the disclosure is a muscle stimulation system, comprising a muscle stimulation control unit adapted to be in communication with a plurality of muscle stimulation electrodes, the plurality of electrodes adapted to be positioned on a subject proximate to a muscle tissue, the muscle stimulation control unit configured to deliver stimulating energy to the plurality of electrodes to stimulate the contraction of muscle tissue; and a thermal device in communication with the muscle stimulation control unit, the thermal device adapted to change the temperature of tissue proximate the plurality of muscle stimulation electrodes, wherein the stimulation control unit includes a temperature controller adapted to modulate the temperature of the thermal device.

In some embodiments the thermal device comprises a thermoelectric device. In some embodiments the thermal device is configured to facilitate gas expansion. In some embodiments the thermal device is a cooling device adapted to lower the temperature of at least one thermal element.

In some embodiments the thermal device is configured such that the thermal element can be releasably interfaced with the thermal device. The thermal device can comprise at least one thermal device receiving element configured to receive and secure a thermal element therein. The thermal device can comprise a plurality of thermal device receiving elements each configured to receive and secure a different thermal element therein.

In some embodiments the system further comprises an indicator configured to provide an indication that the thermal element has reached a predefined temperature. In some embodiments the system includes a controller adapted to control the temperature of the thermal element. The temperature controller can be adapted to independently control the temperatures of more than one thermal element. In some embodiments the thermal device includes a temperature controller adapted to control the temperature of the thermal element.

In some embodiments the thermal device includes a plurality of thermal regions, wherein the thermal device is adapted to reallocate power supplied to a first of the plurality of thermal regions to a second of the plurality of thermal regions. In some embodiments the thermal element is a cooling pack. In some embodiments the thermal device includes a fluid lumen, wherein the thermal device may be configured such that a chilled fluid can flow through the fluid lumen and reduce the temperature of the thermal element.

In some embodiments the system further comprises a muscle stimulation pad comprising the plurality of muscle stimulation electrodes, the pad further configured to integrate with the thermal element so that the thermal element is configured to change the temperature of tissue proximate the plurality of muscle stimulation electrodes.

In some embodiments the thermal element is a fluid. In some embodiments the thermal element is a solid with a melting point between about 0° F. and about 110° F.

One aspect of the disclosure is a muscle stimulation system, comprising a muscle stimulation control unit adapted to be in communication with a plurality of muscle stimulation electrodes, the plurality of electrodes adapted to be positioned on a subject proximate to a muscle tissue, the muscle stimulation control unit configured to deliver stimulating energy to the plurality of electrodes to stimulate the contraction of muscle tissue; and a first thermal element with a first thermal source and a second thermal element with a second thermal source different than the first thermal source, the first and second thermal elements configured to be positioned to change the temperature of tissue proximate the plurality of muscle stimulation electrodes via the first and second thermal sources.

In some embodiments the second thermal element is maintained within the first thermal element. The first thermal element can be a gel matrix, and the second thermal element can be at least one phase change material maintained with the gel matrix. The system can further comprise a housing that contains the first and second thermal elements.

In some embodiments the first thermal element is a cooling pack and the first thermal source comprises a gel. In some embodiments the second thermal element is a lumen and the second thermal source is a fluid. The second thermal element can be configured such that the fluid is initially in a solid state.

In some embodiments the first thermal element is a thermoelectric device.

In some embodiments the system further comprises a muscle stimulation pad comprising the plurality of muscle stimulation electrodes, the pad further comprising an interface configured to secure the first thermal element to the pad. The first thermal element can be a cooling pack. The interface can be an elastic sleeve. The pad can further comprises the second thermal element, such as a lumen for housing a fluid or actively melting a solid.

In some embodiments the system further comprises a muscle stimulation pad comprising the plurality of muscle stimulation electrodes, the pad comprises first and second interfaces adapted to secure the first and second thermal elements to the pad.

In some embodiments the pad comprises the first and second thermal elements.

In some embodiments the release of the second thermal source can be modulated via the system. Energy delivery from the first thermal source may not be adapted to be modulated via the system.

One aspect of the disclosure is a method of stimulating muscle comprising positioning a plurality of muscle stimulation electrodes on a patient proximate muscle to be stimulated; positioning a first thermal element associated with a first thermal source and a second thermal element associated with a second thermal sources relative to a patient proximate the plurality of electrodes; activating the first thermal source to cause a temperature change in the patient's tissue; and stimulating the patient's muscle by delivering stimulating energy to the plurality of muscle stimulation electrodes.

In some embodiments the placement of the first and second thermal elements occurs sequentially. In some embodiments the method further comprises activating the second thermal source to further change the temperature of the tissue. Activating the second thermal source can comprise controlling the further change in temperature.

In some embodiments activating the second thermal source to further change the temperature of the tissue comprises changing the temperature towards a desired temperature or temperature range.

In some embodiments the step of positioning the first thermal element activates the first thermal source to cause a temperature change in the patient's tissue. Positioning the first thermal element can comprise positioning a cooling pack relative to a patient proximate the plurality of electrodes to cause a decrease in temperature of the tissue.

In some embodiments positioning a first thermal element associated with a first thermal source comprises positioning a first thermal element with the first thermal source contained within the first thermal element.

In some embodiments positioning a plurality of muscle stimulation electrodes on a patient comprises positioning a stimulation pad comprising the plurality of muscle stimulation electrodes on the patient, and wherein the pad comprises the first thermal element such that positioning the plurality of muscle stimulation electrodes on a patient also positions the first thermal element relative to the patient proximate the plurality of stimulation electrodes.

In some embodiments the method further comprises initiating the activation of the second thermal source after initiating the activation of the first thermal source.

In some embodiments the stimulating step is initiated after the activating step is initiated.

In some embodiments the method further comprises sensing a signal indicative of the muscle stimulation in response to stimulating the patient's muscle, and activating the second thermal source in response to the sensed signal.

In some embodiments the method further comprises sensing a signal indicative of the muscle stimulation in response to stimulating the patient's muscle, and modifying at least an aspect of the delivery of the second thermal source in response to the sensed signal.

One aspect of the disclosure is a muscle stimulation system, comprising a muscle stimulation control unit in communication with a plurality of muscle stimulation electrodes, the plurality of electrodes adapted to be positioned on a patient, the muscle stimulation control unit configured to deliver stimulating energy to the plurality of electrodes to stimulate the contraction of muscle tissue; a thermal device adapted to be positioned proximate the plurality of muscle stimulation electrodes in a cooling region and to change the temperature of tissue proximate the plurality of muscle stimulation electrodes; a temperature controller configured to adjust the energy delivery of the thermal device; and a sensor adapted to sense a signal indicative of tissue temperature in the cooling region, and wherein the temperature controller is configured to adjust at least one of an aspect of the energy delivery of the thermal device and an aspect of the stimulating energy in response to the sensed signal.

In some embodiments the sensor is a temperature sensor.

In some embodiments the temperature controller is disposed in the muscle stimulation control unit.

In some embodiments the temperature controller is configured to adjust the rate at which energy is delivered via the thermal device. The thermal device can be a thermoelectric device. The temperature controller can be adapted to adjust the rate of gas release from a gas reservoir.

In some embodiments the temperature controller is configured to reduce the thermal conductivity between the thermal device and the patient's skin to adjust the energy delivery of the thermal device. The temperature controller can be configured to cause the distance between the patient's skin and the thermal device to increase.

One aspect of the disclosure a muscle stimulation system, comprising a muscle stimulation control unit in communication with a plurality of muscle stimulation electrodes, the plurality of electrodes adapted to be positioned on a patient, the muscle stimulation control unit configured to deliver stimulating energy to the plurality of electrodes to stimulate the contraction of muscle tissue; a thermal device adapted to be positioned proximate the plurality of muscle stimulation electrodes in a cooling region and to change the temperature of tissue proximate the plurality of muscle stimulation electrodes; a temperature controller configured to adjust the energy delivery of the thermal device; and a sensor adapted to sense a signal indicative of muscle stimulation, and wherein the temperature controller is configured to adjust at least one of an aspect of the energy delivery of the thermal device in response to the sensed signal.

In some embodiments the sensor is a mechanical sensor adapted to characterize muscle contraction.

In some embodiments the temperature controller is disposed in the muscle stimulation control unit.

In some embodiments the temperature controller is configured to adjust the rate at which energy is delivered via the thermal device. The thermal device is a thermoelectric device. The temperature controller is adapted to adjust the rate of gas release from a gas reservoir. The temperature controller can be configured to reduce the thermal conductivity between the thermal device and the patient's skin to adjust the energy delivery of the thermal device. The temperature controller can be configured to cause the distance between the patient's skin and the thermal device to increase.

One aspect of the disclosure is a method of stimulating muscle, comprising: positioning a plurality of muscle stimulation electrodes on a patient in the vicinity of muscle to be stimulated; positioning a thermal element relative to a patient proximate the plurality of electrodes; delivering thermal energy to the patient's skin proximate the plurality of electrodes in a cooling region to change the temperature of skin proximate the plurality of electrodes; stimulating the patient's muscle by delivering stimulating energy to the plurality of muscle stimulation electrodes; and adjusting the delivery of the thermal energy.

In some embodiments the method further comprises sensing a patient signal indicative of the muscle stimulation in response to stimulating the patient's muscle, and wherein adjusting the delivery of the thermal energy is in response to the sensed signal.

In some embodiments adjusting the delivery of the thermal energy comprises adjusting the rate at which energy is delivered via the thermal device.

In some embodiments adjusting the delivery of the thermal energy comprises reducing the thermal conductivity between the thermal device and the patient's skin.

In some embodiments the method further comprises sensing a patient signal indicative of the temperature in the cooling region, and wherein adjusting the delivery of the thermal energy is in response to the sensed signal. Adjusting the delivery of the thermal energy can comprise adjusting the rate at which energy is delivered via the thermal device. Adjusting the delivery of the thermal energy can comprise reducing the thermal conductivity between the thermal device and the patient's skin.

In some embodiments adjusting the delivery of the thermal energy in response to the sensed signal causes the temperature of the skin to be reduced.

In some embodiments the thermal element is a cooled element, and delivering thermal energy comprises reducing the temperature of the skin.

One aspect of the disclosure is a muscle stimulation system, comprising a muscle stimulation control unit adapted to be in communication with a plurality of muscle stimulation electrodes, the plurality of electrodes adapted to be positioned on a subject proximate to a muscle tissue, the muscle stimulation control unit configured to deliver stimulating energy to the plurality of electrodes to stimulate the contraction of muscle tissue; a thermal controller adapted to modulate the temperature of at least one thermal element that is adapted to be positioned relative the patient to change the temperature of tissue proximate the plurality of muscle stimulation electrodes; and an indicator configured to provide an indication that the thermal element has reached a particular temperature.

In some embodiments the indicator is disposed on the muscle stimulation control unit.

In some embodiments the indicator is disposed on the thermal controller.

In some embodiments the indicator is disposed on the thermal element.

One aspect of the disclosure is a muscle stimulation system, comprising a muscle stimulation pad comprising a plurality of muscle stimulating electrodes in a predetermined orientation on the pad, the muscle stimulation pad further comprising an securing member adapted to integrate with a thermal device in such a manner that the thermal device is secured relative to the pad in a position to change the temperature of tissue proximate the plurality of muscle stimulation electrodes, the muscle stimulation pad adapted to be in communication with a muscle stimulation control unit configured to deliver stimulating energy to the plurality of electrodes.

In some embodiments the securing member is adapted to releasably integrate with the thermal device.

In some embodiments the securing member and the thermal device are sized and configured such that the securing member maintains the thermal device firmly in contact with the pad.

In some embodiments the securing member and the thermal device are sized and configured such that the securing member maintains the thermal device firmly in contact with the patient's skin.

In some embodiments the securing member and the thermal device are sized and configured such that the securing applies positive pressure to the thermal device.

In some embodiments the securing member and the thermal device are sized and configured such that the securing member is adapted to apply a downward force on the thermal device towards the patient's skin.

In some embodiments the securing member comprises an elastic material. The elastic material can be an elastic sleeve. The elastic sleeve can have a sleeve dimension in a resting state that is smaller than a corresponding thermal device dimension. The elastic sleeve can have a length in a resting state that is less than a corresponding length of the thermal device.

In some embodiments the securing member comprises straps circumscribing a portion of the thermal element.

One aspect of the disclosure is a muscle stimulation system, comprising a muscle stimulation pad comprising a substrate, a plurality of muscle stimulating electrodes positioned in a predetermined orientation with respect to the substrate, and a thermal region that has a reduced barrier to thermal conductivity, the muscle stimulation pad adapted to interface with a thermal device, the pad adapted to be positioned on a subject such that the plurality of muscle stimulating electrodes are disposed proximate a muscle to be stimulated and such that the thermal device is positioned to change the temperature of tissue proximate the plurality of stimulation electrodes, the muscle stimulation pad adapted to be in communication with a muscle stimulation control unit configured to deliver stimulating energy to the plurality of electrodes to stimulate the contraction of muscle tissue.

In some embodiments the thermal region comprises a discontinuity in the substrate.

In some embodiments the thermal region is a window in the pad.

In some embodiments the thermal region is a discontinuity in the substrate that has therein a material that is more thermally conductive than the substrate. The material can be a thermally-conductive hydrogel.

In some embodiments the thermal region is a region of the pad with less insulation that other sections of the pad. The pad can includes an insulation layer, and in the thermal region the insulation layer has a thickness that is less than a thickness of the insulation outside of the thermal region. The thermal region can be void of the insulation layer.

In some embodiments the thickness of the thermal region measured from a top surface of the pad to a bottom surface of the pad is less than a thickness of the pad outside of the thermal region.

In some embodiments the thermal device overlaps with the entire surface area of the plurality of stimulating electrodes.

In some embodiments the thermal device does not overlap the entire surface area of the plurality of stimulating electrodes. The thermal device can overlap with a portion of the surface area of the plurality of stimulating electrodes.

One aspect of the disclosure is a muscle stimulation system, comprising a muscle stimulation control unit adapted to be in communication with a plurality of muscle stimulation electrodes, the plurality of electrodes adapted to be positioned on a subject proximate to a muscle tissue, the muscle stimulation control unit configured to deliver stimulating energy to the plurality of electrodes to stimulate the contraction of muscle tissue; and a thermal device that is in at least one of electrical and mechanical communication with the muscle stimulation control unit, the thermal device adapted to modulate the temperature of at least one thermal element that is configured to change the temperature of tissue proximate the plurality of muscle stimulation electrodes.

In some embodiments the thermal device is not an integral part of or attached to any of the plurality of stimulation electrodes In some embodiments at least one of (and optionally both) the control unit and the thermal device are integrated into a hospital bed.

In some embodiments the muscle stimulation control unit is attached to the thermal device.

In some embodiments the muscle stimulation control unit comprises a housing, and wherein the thermal device is integrated within the housing.

In some embodiments the thermal device is a cooling device adapted to lower the temperature of at least one thermal element.

In some embodiments the thermal device is configured such that the thermal element can be releasably interfaced with the thermal device. The thermal device can comprise at least one thermal device receiving element configured to receive and secure a thermal element therein. The thermal device can comprise a plurality of thermal device receiving elements each configured to receive and secure a different thermal element therein. The thermal device can comprise a surface upon which the control element can be positioned to releasably secure the thermal element.

In some embodiments the system further comprises an indicator configured to provide an indication that the thermal element has reached a predefined temperature. The thermal device can comprise the indicator, and wherein the indicator is at least one of an audio indicator and a visual indicator. The thermal element can comprise the indicator.

In some embodiments the stimulation control unit includes a temperature controller adapted to control the temperature of the thermal element. The temperature controller can be adapted to independently control the temperatures of more than one thermal element.

In some embodiments the thermal device includes a temperature controller adapted to control the temperature of the thermal element. The temperature controller can be adapted to independently control the temperatures of more than one thermal element.

In some embodiments the thermal device includes a plurality of thermal regions, wherein the thermal device is adapted to reallocate power supplied to a first of the plurality of thermal regions to a second of the plurality of thermal regions.

In some embodiments the thermal element is a cooling pack.

In some embodiments the thermal device includes a fluid lumen, wherein the thermal device is configured such that a chilled fluid can flow through the fluid lumen and reduce the temperature of the thermal element.

In some embodiments the system further comprises a muscle stimulation pad comprising the plurality of muscle stimulation electrodes, the pad further configured to integrate with the thermal element so that the thermal element is configured to change the temperature of tissue proximate the plurality of muscle stimulation electrodes.

In some embodiments the thermal element is a fluid.

In some embodiments the thermal element is a solid with a melting point between about 0° F. and about 110° F.

BRIEF DESCRIPTION OF THE DRAWINGS

FIGS. 12(a)-12(d) show variations of systems and devices that may allow for cooling packs to be implemented to provide local superficial cooling to tissue during muscle stimulation.

FIGS. 15(a)-15(d) illustrate systems and devices that allow for thermoelectric devices to be interfaced with or used in conjunction with muscle stimulation such that surface thermal energy may be provided to tissues.

FIGS. 16(a)-16(d) illustrate systems and devices that use compressed gases or pressure-based canisters to interface with or to be used in conjunction muscle stimulation in order to provide surface cooling to tissues.

DETAILED DESCRIPTION OF THE DISCLOSURE

The disclosure provides devices and systems configured for improved energy delivery to human or animal tissue. Though this disclosure uses the modality of NMES as an illustrative example, it is understood that the disclosure may be applied with utility to other energy-delivery therapies, such as TENS or RF or microwave ablative therapies as well. Various aspects of the disclosure herein may be applied to any of the particular applications set forth below or for any other types of electrical stimulation systems and methods. The disclosure may be applied as a standalone device, or as part of an integrated medical treatment system. It shall be understood that different aspects of the disclosure can be appreciated individually, collectively, or in combination with each other.

While aspects of this disclosure describe devices, systems, and methods to increase the amount of stimulating electrical energy that is delivered to a muscle, such as via a thermal guidance field, the devices, systems, and methods herein are not necessarily configured as such and need not be used in this manner. Increasing the amount of stimulating electrical energy that is delivered to a muscle is merely an example of how the devices and systems herein can be used. For example, the systems, devices, and methods herein can apply thermal energy (which includes the removal of energy) to the body without necessarily increasing the amount of stimulating electrical energy that is delivered to a muscle.

In some embodiments an energy delivery system includes a plurality of surface electrodes configured to facilitate the delivery of electrical energy into and out of a patient's body, a device configured to apply thermal energy to the body proximate to the electrodes, and a stimulation control unit that creates the stimulation energy pulses and delivers them to the electrodes.

In embodiments of NMES herein, electrical energy is applied to muscle tissue transcutaneously by surface electrodes that are secured to a person's skin. Some of the embodiments may provide ways to increase the amount of electrical energy that is delivered to the muscle without increasing the amount of electrical energy delivered to the patient. That is, in these embodiments, a greater percentage of the electrical energy delivered to the subject is delivered to muscle tissue (as opposed to other tissue), which provides for more efficient muscle stimulation. A greater percentage of the electrical energy is thus delivered to muscle tissue by creating an energy guidance field to drive the energy towards muscle tissue.

Figure 1A:
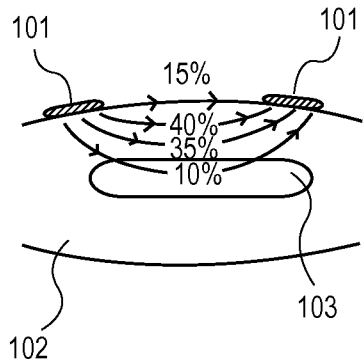
FIGS. 1A-1E illustrate how a cooling element can affect electrical current paths through tissue.

FIGS. 1A-1D schematically illustrate side-views of an exemplary use of systems and devices herein that increase the efficiency of muscle stimulation using NMES. FIG. 1A shows a lateral cross-sectional view of limb 102 of a generally healthy patient with two surface electrodes 101 attached thereto. Electrodes 101 are in communication with a stimulation unit (not shown) configured to deliver current to the electrodes and thereby deliver current through the patient's tissue. FIG. 1A illustrates the direction that the current is traveling (indicated by the arrows) and indicates a percentage of the energy that is reaching a given region of tissue within limb 102. As shown, only a relatively small percentage of the electrical current entering limb 102 reaches deep-lying muscle tissue 103 (shown as 10%).

Figure 1B:
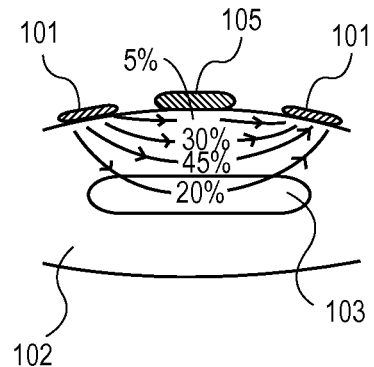

FIG. 1B illustrates limb 102 from FIG. 1A but includes a surface cooling element 105 placed in contact with the surface of the skin, and is disposed on the skin at a location between stimulation electrodes 101. Cooling element 105 generally creates an energy guidance field to drive energy deeper towards muscle tissue. In this embodiment, cooling element 105 creates a temperature gradient from the surface of the skin to a location below the surface of the skin. The surface of the skin can be considered the low temperature end of the temperature gradient. The frequencies of electrical energy utilized by muscle stimulators are generally lower (generally lower than about 10 kHz) than those used in ablative or cosmetic applications (generally greater than about 300 kHz for RF and greater than about 3 GHz for microwave), and thus typically do not generate significant tissue heating, especially in deep tissue regions. Additionally, the use of muscle stimulators typically does not produce tissue temperatures greater than about 40° C. (consistent with many regulatory and governing body guidelines—see Prausnitz 2006 above). For tissue temperatures below 40° C., the effect of temperature on tissue impedance is generally opposite that found at the higher temperatures used during ablative and cosmetic procedures, with tissue impedance increasing by about 2%/° C. (see Miklavcic et al, *Electrical Properties of Tissues*, Wiley Encyclopedia of Biomedical Engineering, 2006, which is incorporated herein by reference). When the tissue nearest the surface of the skin is cooled due to the application of cooling element 105, a three-dimensional temperature gradient will be created in the tissue, which will essentially create a three-dimensional impedance gradient where the impedance of a tissue will increase in proportion to the degree to which it is cooled. The amount of tissue impedance increase from body temperature impedance level is therefore at least partially dependent on the distance between cooling element 105 and the tissue. Tissues nearest the surface where cooling element 105 is disposed are cooled the most and will experience the largest impedance increases relative to body temperature impedance levels. The impedance at depths near muscle tissue 103 will increase less (if at all) than the impedance of the tissue directly under cooling element 105. NMES coupled with surface cooling therefore has the opposite effect that superficial cooling has when used with higher temperature applications such as ablation or cosmetic procedures described above.

In some embodiments the cooling element lowers the skin temperature in the region of cooling to be in the range from about 30 to about 40° F. Maintaining surface temperatures in this range may create a thermal gradient sufficient to change local tissue impedance and increase the efficiency of energy transfer during NMES. Accordingly, the degree of muscle contraction achievable with a given amount of stimulation energy may be increased. Alternatively, surface temperatures cooler than 30° F. and warmer than 40° F. may also be used to increase NMES efficiency, depending upon the local anatomical, physiological, and electrical properties of tissues in the stimulation region and the treatment goals of the NMES therapy session.

As shown, the percentage of electrical energy that travels through muscle tissue is greater in FIG. 1B than in FIG. 1A (due to the energy guidance field created by cooling element 105), while the percentage of electrical energy that travels through the superficial tissue is less in FIG. 1B than it is in FIG. 1A. The increase in the amount of energy that stimulates the muscle tissue, or which stimulates the nerves innervating the muscle tissue, will increase the amount of muscle contraction. The muscle therefore contracts to a greater degree in FIG. 1B than in FIG. 1A. FIG. 1B illustrates the concept of altering the relative impedance of superficial and muscle tissue in the region between the stimulation electrodes in a way that will cause a greater percentage of the electrical current delivered to the body to travel along a tissue pathway that will produce, or result in, muscle contraction.

Figure 1C:
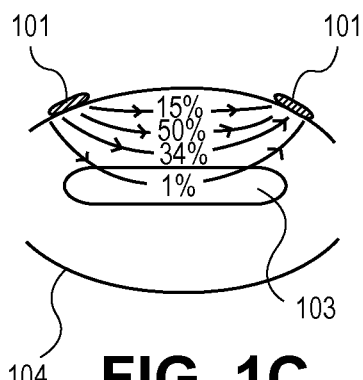
Figure 1D:
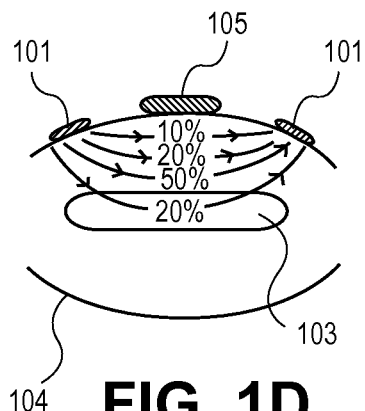

FIG. 1C illustrates a cross-section of an edematous limb 104 with significant tissue swelling. Limb 104 has electrodes 101 positioned similarly to the embodiment shown in FIGS. 1A and 1B. As shown, the distance between the skin surface and muscle 103 is greater than the same distance in the generally healthy limb shown in FIG. 1A. Additionally, short-circuit effects due to excessive ionic fluid may affect the very little (if any) electrical current reaching the deep muscle tissue. As shown, only 1% of the electrical current which is delivered to the limb reaches the muscle. FIG. 1D, compared to FIG. 1C, illustrates the effect that cooling element 105 on the surface of the skin has on the percentage of the electrical current delivered to the body that travels along a tissue pathway that will produce, or result in, muscle contraction. The amount of muscle contraction is greater in FIG. 1D than it is in FIG. 1C. All quantitative information shown in FIGS. 1A-1D is for illustrative purposes and does not necessarily reflect actual functionality of a NMES device applied to a limb surface.

Figure 1E:
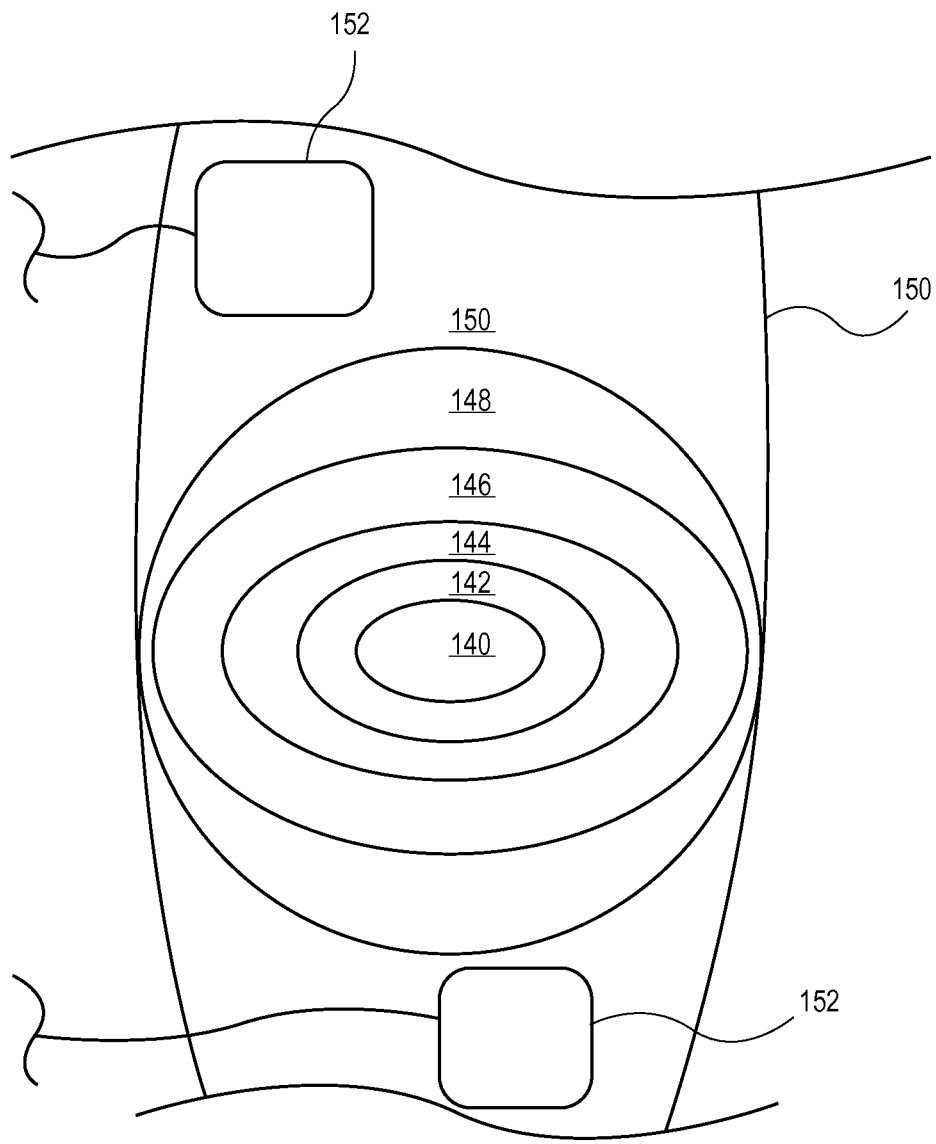

FIG. 1E illustrates a two-dimensional temperature gradient on the skin of a portion of leg 150 after a cooling element was placed on the leg for about 7 minutes. The cooling element was placed generally horizontally on the leg, and had a width generally larger than its height, and approximated the shaping of cooling element 204 shown in FIG. 3B. The cooling element was placed substantially in the region indicated as 140 in FIG. 1E. Electrodes 152 are also shown positioned on the leg. The temperature of the skin on the leg was measured after the cooling element was removed. The sizes of the zones indicated are approximations. In zone 140 the temperature of the skin was about 37° F. In zone 142 the temperature was about 42° F. In zone 144 the temperature of the skin was about 57° F. In zone 146 the temperature of the skin was about 72° F. In zone 148 the temperature of the skin was about 85° F. In zone 150 the temperature of the skin was about 87° F. FIG. 1E represents an exemplary temperature gradient after a generally rectangularly-shaped cooling element is placed horizontally between electrodes. Cooling elements with alternative shapes will likely create different temperature gradients, and may in some instances cool the skin that is closer to the electrodes more than that which is discussed in reference to FIG. 1E. For example, one or more of electrodes 152 could be in region 148, 146, 144, or perhaps in some embodiments could even be in zones 142 or 140. While not shown in FIG. 1E, it is understood that the cooling element also creates a temperature gradient through the depth of the leg.

In some embodiments of NMES therapy systems and methods herein, there is generally no or little cooling effect at the anatomical locations where energy enters or exits the body (i.e., skin upon which the skin electrodes are disposed and closely adjacent thereto), and therefore impedance changes in these regions are minimal or negligible. Energy delivery to and from the body should therefore not be altered significantly because, for example, the impedance in the skin directly adjacent the surface electrodes will not substantially increase. Also, because cooling occurs in precise locations that assist energy transfer to non-superficial muscles, the total path impedance is increased much less than it would be if cooling were applied to the skin over larger anatomical regions (i.e., those that include the electrode locations). Additionally, excessive heat will not be generated in the surface electrodes, and thus drying of hydrogel layers should not be accelerated.

FIGS. 1B and 1D illustrate an exemplary embodiment which does not significantly increase skin temperature or tissue impedance on the locations where energy enters or exits the body. As illustrated in FIGS. 1B and 1D, the cooling element is positioned at a location on the skin that substantially avoids a cooling effect at the location of the skin where the electrodes are positioned. Because there is substantially no or very little cooling in the skin to which the electrodes are attached, there is a negligible change in impedance at that location. Electrodes 101 are shown positioned on the skin at a location that is different than the location cooling element 105 is positioned. In particular, in FIGS. 1B and 1D, cooling element 105 is positioned between electrodes 101. By positioning the cooling element between the electrodes, energy transfer in and out of the body remains substantially unaffected.

While the systems and methods of use herein are described as not markedly increasing skin or superficial tissue impedance in the locations where energy enters or exits into the body, in some alternative embodiments the temperature at tissue where energy enters or exits is decreased. The tissue impedance in this region would therefore increase to some extent (perhaps only minimally) and the energy transfer through the tissue will likely not be as efficient as in embodiments where cooling does not occur where energy enters or exits the body. For example, in FIGS. 1B and 1D, the cooling element could extend over one or both electrodes 101.

As shown in FIGS. 1C and 1D, the application of NMES with tissue cooling can be particularly useful in edematous patients whose tissues may exhibit properties such as the 'short circuit' condition described herein. The systems can, however, also have significant value for healthy or non-edematous persons as well. The systems will allow for more efficient muscle stimulation, which decreases the amount of energy that needs to be to be delivered to the body to produce a given amount of muscle contraction. The reduction in required energy may increase patient tolerance of NMES therapy, in part by reducing the current amplitude reaching superficial nerves (i.e., reduction of the 'pins and needles' discomfort phenomenon). This reduction in energy will also reduce the risk for burns, nerve and/or muscle damage, and other potential complications. The therapies described herein may also be immensely helpful in the NMES treatment of overweight or obese persons (who may be defined by body-mass index), or other persons who require large stimulation energy amplitude to elicit significant muscle contraction. These individuals typically require large stimulation energies to combat the capacitive effect created by excessive adipose located superficial to muscle tissue. For these individuals, the highest energy amplitude allowed by regulatory and/or overseeing body safety standards are frequently required to induce even minimal muscle contraction. As further energy amplitude increases are not an option for these individuals, a more efficient use of the energy that is delivered is imperative to induce effective muscle contraction. Additionally, by reducing inter-patient performance variability, there can be more widespread adoption of the therapies described herein in critical care, skilled nursing facilities, and long-term rehabilitation care settings.

Figure 2:
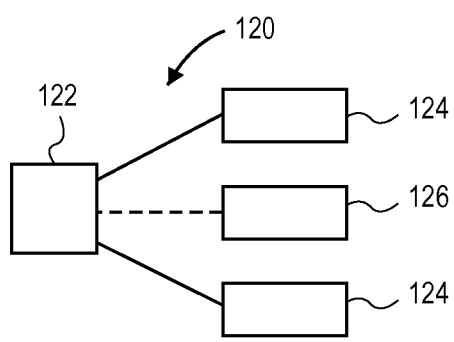
FIG. 2 illustrates an exemplary NMES system.

FIG. 2 illustrates an exemplary schematic representation of a NMES therapy system 120 including stimulation control unit 122, surface electrodes 124, and cooling element 126. Stimulation control unit 122 creates stimulation energy pulses and delivers them to surface electrodes 124, which deliver electrical energy into and out of the body. Cooling element 126 is adapted to apply thermal energy to the body in a region proximate the surface electrodes 124, such as between and/or surrounding surface electrodes 124. Control unit 122 communicates with surface electrodes 124 in a manner suitable for transmitting and receiving electrical signals, such as with a standard cable connection, a wireless connection such as Blue-tooth, WiFi, RF, infrared, optical, acoustic, or other suitable type of connection. In some embodiments control unit 122 is in communication with cooling element 126. Control unit 122 is a housing generally separate from electrodes 124, and can be positioned a distance from the person receiving therapy on whom the electrodes are positioned. In alternate embodiments, the control unit may be integrated into a housing unit that includes the stimulating electrodes and/or cooling element. In some embodiments, examples of which are provided below, the stimulation electrodes are housed in a stimulation pad such that the electrode layout and configuration is optimized for a particular region of the body.

In some embodiment herein, the control unit may also control the operation of the cooling element or thermal mechanism as it may be referred to herein. In some embodiments, the stimulation electrodes will be assembled into a custom stimulation pad such that electrode layout and configuration is pre-optimized for a particular region of the body. The control unit can communicate with the stimulation pad through a wired connection, radiofrequency transmission, optical, acoustic, or electromagnetic signals, or another suitable mechanism. The control unit is a separate unit that may be located some distance from the person receiving therapy. In an alternate embodiment, the control unit may be integrated into a housing unit that includes the stimulating electrodes and/or temperature-change components, or in another way be adapted to reside proximate to the region of NMES.

The control unit can include components such as a signal generator, memory, processor, and power supply. The primary operation of the control unit may be provided by a microprocessor, field programmable gate array (FPGA), application specific integrated circuit, some combination of these mechanisms, or other suitable mechanism. Some electrical stimulation parameters, including the duration of therapy, are adjustable by the operator through buttons, knobs, dials, or switches on the control unit. Other electrical stimulation parameters, such as stimulation pulse energy amplitude, may be adjusted by the user through control unit controls or be automatically optimized using automatic algorithms implemented by the control unit. The control unit may also include items such as a touchscreen or other form of display and/or user interface, data acquisition channels and associated hardware/software, and other safety-control features.

In some embodiments, the control unit is capable of transmitting stimulation pulses on at least one and preferably many more (e.g., 6-12) channels simultaneously and independently. In some embodiments, the control unit is also capable of creating arbitrary phase delays between pulses originating from different channels. In variations of these embodiments, the control unit is configured to transmit pulses on some channels dependently and others on different channels independently.

An exemplary method of using NMES therapy systems referred to generally in FIGS. 1 and 2 will now be described. Methods of using the systems and devices described herein may include one or more of the following steps, performed in any suitable order during the therapy procedure. The order of the following steps is exemplary only and is in no way intended to be limiting. The exemplary method provides for a more efficient transfer of electrical energy to deep-lying muscle tissues while minimizing the increase in the degree of heat generated in skin electrodes. At least two electrodes are placed on the surface of the skin in the vicinity of a muscle to be stimulated. Cooling energy is applied to skin tissue in a region proximate the electrodes, such as between and/or surrounding, the stimulation electrodes. The application of the cooling energy creates a temperature gradient in which the temperature of the skin and superficial tissue is lowered from their normal temperature to a greater extent than the temperature of deeper-lying tissue (e.g., muscle) is lowered from its normal temperature. Stimulation energy is then applied through the subject by applying stimulation energy to the surface electrodes. The stimulation energy is generated and delivered to the electrodes by a stimulation control unit in communication with the electrodes.

In some methods of therapy it is not required to simultaneously apply surface cooling and electrical stimulation. For example, superficial tissue may first be pre-cooled by, for example, a predetermined temperature or for a predetermined amount of time, after which the thermal stimulus is removed. The temperature gradient will begin to decay at a given rate once the thermal stimulus is removed. Experience suggests that the re-warming rate of the body part is relatively slow, and it could take as long as about 30 minutes or more for a large body part such as the thigh to regain its pre-cooled temperature distribution. During the re-warming period, the NMES performance would be improved by some degree without the need for simultaneous cooling. This particular embodiment of the method is a further example of how known therapies have not recognized the benefit of combining temperature gradients with muscle stimulation.

In some methods cooling is administered intermittently. In these embodiments, surface cooling has "on" periods and "off" periods. For example, during a 60 minute NMES session, cooling energy can be applied every 10 minutes for 5 minutes. One advantage of intermittent cooling is that after superficial tissue temperatures are lowered enough to cause effective changes in tissue impedance, surface cooling can be discontinued, which can prevent skin temperatures from cooling to the extent that the thermal stimulus becomes uncomfortable, intolerable, or unsafe to the person receiving NMES.

Figure 3A:
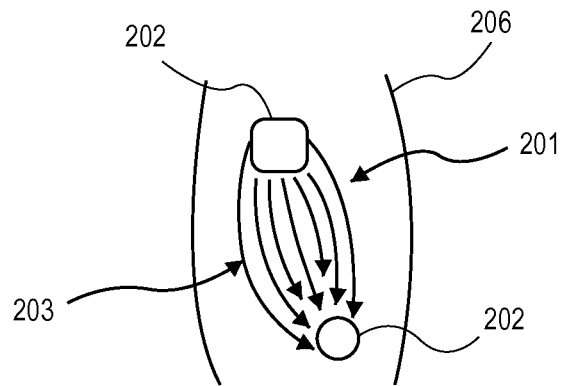
FIGS. 3A-3C illustrate the effect that cooling superficial tissue can have on the paths that current take through tissue.
Figure 3B:
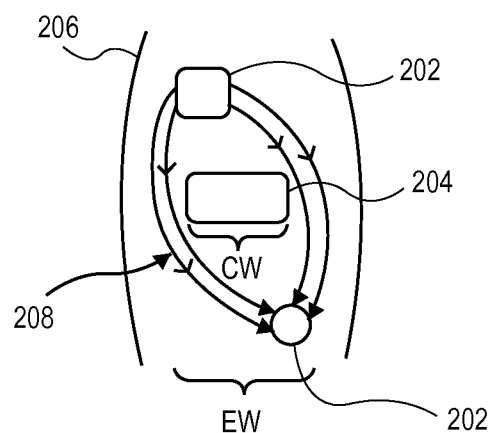
Figure 3C:
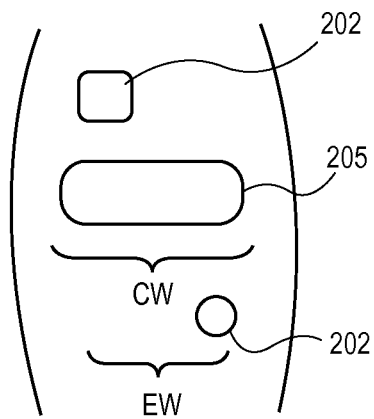

In some embodiments, the surface tissue is cooled to increase the impedance of the surface tissue and superficial tissue in order to divert a greater percentage of the electrical energy entering the body to non-superficial muscle tissue (e.g., deep-lying muscle). One goal in these embodiments is therefore to increase the amount of energy that travels along a deeper path and decrease the amount of energy that travels along a shallow path (i.e., a path closer to the surface). As current travels from one electrode to another, however, a large percentage of the energy (or a larger percentage of energy than that which is desired) may travel along or in close proximity to the surface of the skin if the cooling effect is limited to a small region of skin, or if the cooling does not adequately reduce the temperature of the surface of the skin. FIG. 3A illustrates an example of this by illustrating a top-view of low impedance superficial current pathways between two surface electrodes during NMES. In FIG. 3A electrodes 202 are positioned on the surface of skin 206 in stimulation region 201. A distribution of energy pathways 203 illustrate the path current may take when flowing between electrodes 202 under normal conditions. In FIG. 3B cooling element 204 is positioned between electrodes 202. Cooling element 204 has a width "CW" that is similar to a width that electrodes 204 span, "EW." Cooling element 204 eliminates many of the low impedance superficial energy pathways, although some may remain. FIG. 3B shows current paths 208 that exist where low impedance superficial tissue pathways were not eliminated because the cooling effect from cooling element 104 does not sufficiently cool the superficial tissue to increase the impedance sufficiently. Current paths 208 arc around the cooler tissue region. FIG. 3C illustrates cooling element 205 width "CW" that is wider than the width the electrodes span, "EW." The region of superficial cooling is wider (along the transverse plane) than the width of the stimulation electrode distribution. Width CW increases tissue electrical impedance over a large area and thus eliminates nearly all of the low impedance superficial energy pathways. In FIG. 3C current pathways exist below the surface of the skin (not shown). In FIG. 3C, the region of cooling-induced impedance change is sufficient to minimize or even eliminate the existence of superficial low-impedance electrical pathways that arc around the cooled region of tissue.

The size, shape, configuration, etc., of the cooling element can therefore have an effect on the temperature gradient and the degree to which superficial tissue impedance in the stimulation area is altered.

In some embodiments, however, the cooled tissue region may have a width that is similar to the width of the electrode distribution, or even less than the width of the electrode distribution. The width of the cooled tissue region can depend on the local electrical characteristics of the tissue and/or the treatment goals of the NMES therapy session.

Figure 4A:
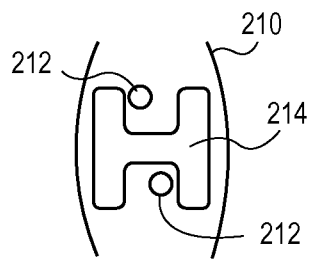
FIGS. 4A-4D illustrate exemplary cooling elements.
Figure 4B:
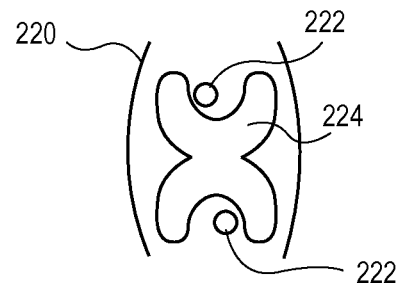
Figure 4C:
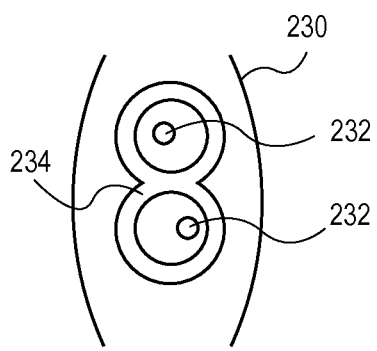
Figure 4D:
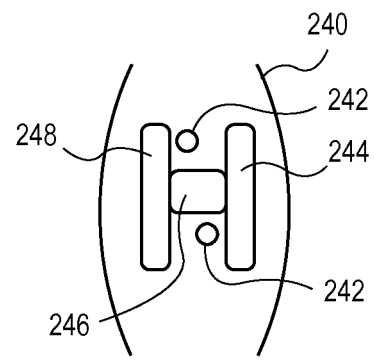

FIGS. 4A-4D show alternative configurations of exemplary cooling elements which are positioned between and at least partially surrounding the electrodes. In the figures, the electrodes have reference numbers 212, 222, 232, and 242 respectively. In FIG. 4A, cooling element 214 is substantially "H-shaped" and placed on skin 210 to minimize the superficial low impedance electrical pathways. In FIG. 4b, cooling element 224 with a shape which mimics two integrated "U" shapes is positioned between and partially surrounding electrodes 224 on skin 220. Cooling element 224 could alternatively be two distinct cooling elements positioned on the skin in the configuration shown in FIG. 4B. In FIG. 4C, cooling element 324 has a substantial FIG. 8 configuration and is positioned on skin 230 between and surrounding electrodes 232. Cooling element 234 could alternatively be two "O" shaped cooling elements positioned on the skin in the configuration shown in FIG. 4C. FIG. 4D shows the "H-shaped" cooling element in FIG. 4A as three discrete cooling elements, 244, 246, and 248 positioned on skin 240 between electrodes 242. Alternative configurations, shapes, and sizes of cooling elements may also be used.

Figure 5:
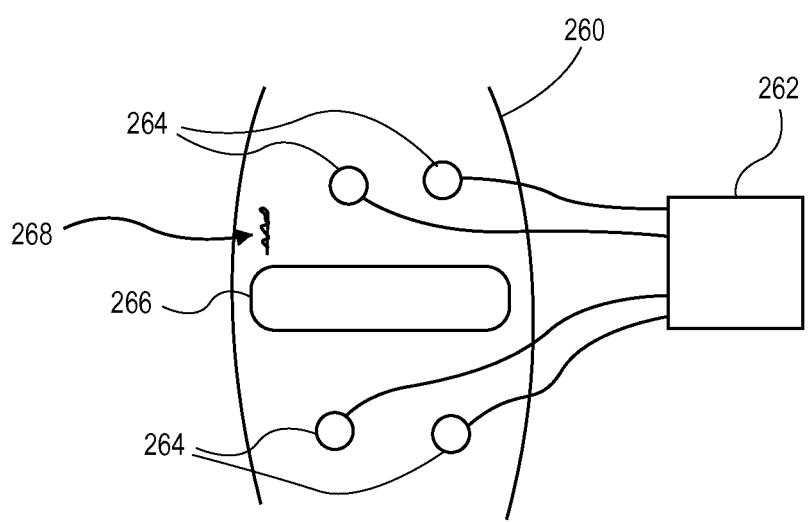
FIG. 5 illustrates an exemplary system that includes discrete electrodes and a cooling element.

In some embodiments the system includes a plurality of electrodes and a cooling element that are discrete elements and not coupled to one another. The electrodes and cooling elements are, in these embodiments, secured to the skin as separate elements. FIGS. 3 and 4 show such embodiments. The electrodes themselves may also be uncoupled from one or more other electrodes. FIG. 5 shows a plurality of discrete electrodes 264 placed on skin 260. Electrodes 264 are in electrical communication with control unit 262 by leads. Cooling element 264 is not coupled to electrodes 264. Electrodes which are not coupled to the cooling element and/or each other can be useful in patients with abnormal pathology or who have other simultaneous medical interventions that would prevent the use of a pre-manufactured stimulation pad as described below. For example, electrodes 264 and cooling element 266 can be positioned on skin 260 to avoid a broken region of skin 268 (although broken skin is not a contraindication to NMES therapy in general). The use of discrete surface electrodes and cooling element(s) can enable an NMES operator to place the stimulation system components in safe and effective locations that are tailored to the needs of the individual.

In some embodiments two or more stimulation electrodes are secured to each other in a single housing, or pad (which may also be referred to herein as a patch), while in some embodiments one or more electrodes are housed with one or more cooling elements in a single housing, or pad. In some embodiments the system includes a custom stimulation pad that has surface electrodes placed in predetermined configurations or positions on the pad. As used herein, a predetermined configuration includes electrodes that can move, such as by flexing, with respect to the pad. A predetermined configuration of electrodes as used herein refers to a general position of the electrode with respect to a pad substrate, with the understanding that it can be configured to move (e.g., flex) to some degree with respect to other pad components.

Additionally, as used herein, a predetermined configuration includes the idea what electrodes can be removed completely from the pad. That is, the electrodes can be in predetermined configuration and still be attached and detached from the pad.

Any number of electrodes can be included in a stimulation pad. A custom stimulation pad can also be configured with a built-in cooling element, or it can be configured such that a detachable cooling element can be easily attached, integrated, connected, or used in conjunction with the stimulation pad. As used herein integrated include positioning the cooling element relative the pad but not being in contact with the pad. These embodiments can assist an NMES operator in applying the surface cooling in the optimal location to increase the efficiency of energy delivery to deep muscle tissues. A stimulation pad can also be configured such that individual electrodes can be detached from the pad.

In an exemplary embodiment of a system with a stimulation pad, the stimulation electrodes are arranged in a configurable array. The array is configurable such that, at any given time during therapy, any number of electrodes in the array, including only a subset of the electrodes in the array, are actively delivering energy to a person receiving NMES. However, electrodes inactive for energy delivery may still be configured to deliver relevant information to the control unit, described in more detail below. For example, one or more inactive electrodes can be used to measure electrical impedance between it and a second electrode.

Figure 6:
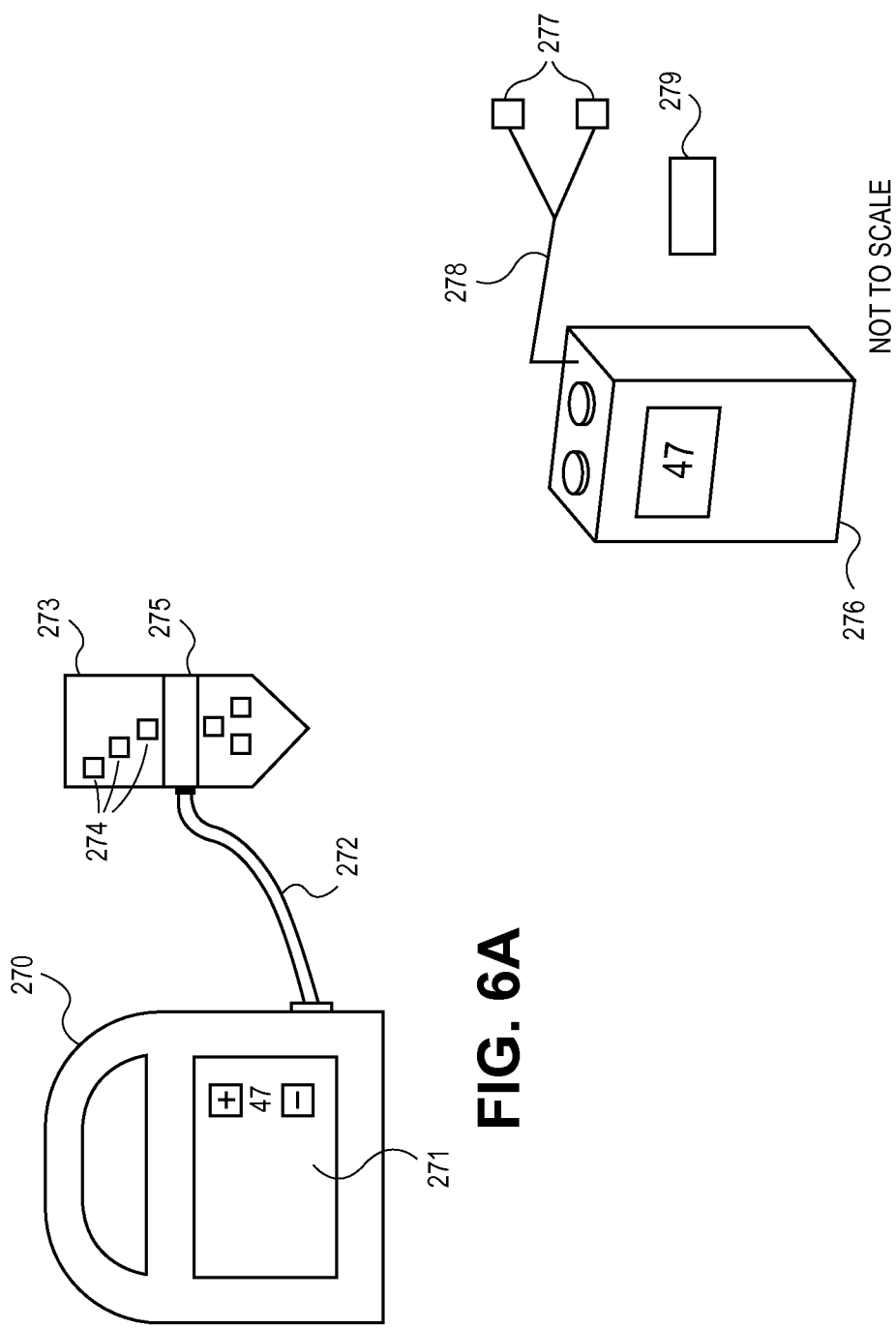
FIGS. 6A and 6B illustrate exemplary NMES systems that employ a thermal element.

FIG. 6A illustrates an exemplary system that includes control unit 270 connected to stimulation pad 273 via a wired interface cable 272. Control unit 270 includes user interface 271, shown as an LCD touchscreen display. Other components of the control unit (for example power entry module, internal electronics) are not referenced but their inclusion in control unit 270 is implied. Stimulation pad 273 includes stimulation electrodes 274 in a predetermined layout that are configured to deliver stimulation energy generated by control unit 101 to the person receiving therapy. Stimulation pad 273 also includes a thermal element interface region where cooling element 275 integrates to provide surface cooling to the person receiving therapy. FIG. 6B illustrates a system that does not include a pad, the system including control unit 276 in wired connection 278 with discrete electrodes 277 that can be placed in the intended region of treatment. A separate cooling element 279 may be placed proximate to the region of stimulation.

In some embodiments the stimulation pad is comprised of a thin and flexible housing with an adhesive backing, such as hydrogel, to facilitate maintenance of skin contact. A hydrogel backing will also enhance the coupling of electrical energy and signals between stimulation electrodes and the person's body. In some embodiments more than one adhesive material may be used. For example, electrode contact areas may have a hydrogel or similar backing while other pad areas may be secured with a more gentle adhesive, such as adhesives used in bandages. A hydrogel backing for electrodes will also enhance the coupling of electrical energy and signals between stimulation electrodes and the person's body.

In some embodiments a stimulation pad may also include a small and lightweight control unit that is intended to sit proximate to the region of tissue being treated.

Figure 7:
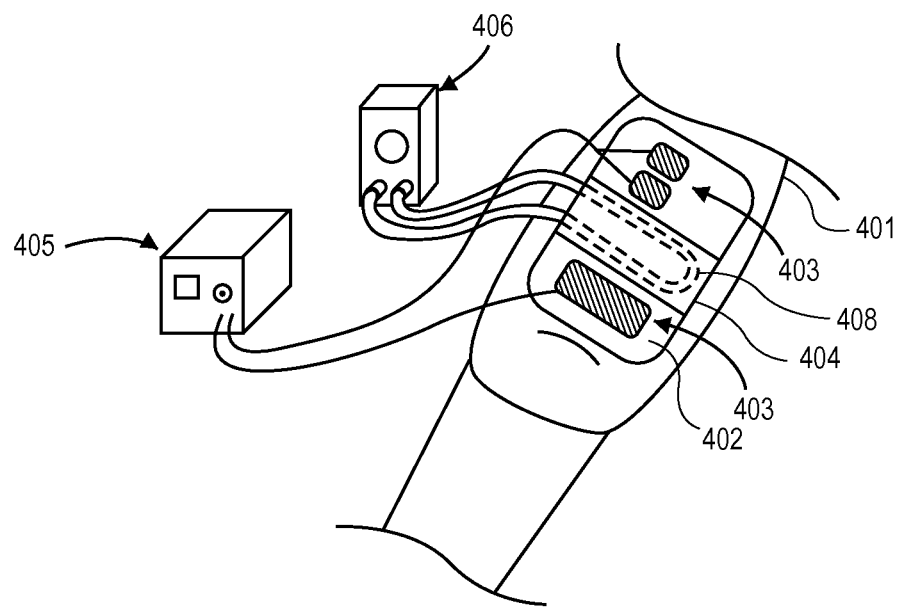
FIG. 7 illustrates a stimulation pad with a cooling element comprises a fluid lumen.

FIG. 7 illustrates an exemplary embodiment of an NMES system including a stimulation pad positioned on a thigh region of leg 401. Surface electrodes 403 and cooling element 404 are integrated into stimulation pad 402, which is thermally conductive, soft, and flexible. The flexibility allows it to flex as needed when being applied to a region of the body with contours. Control unit 405 communicates with the stimulation electrodes via a wired connection to deliver electrical energy to the leg. Thermal control 406, which in this embodiment includes a pump, is in communication with a cooling element 404. Cooling element 404 includes a lumen 408 within the pad which is in fluid communication with the pump of thermal control 406. The pump (e.g., a peristaltic pump) is connected via inflow and outflow tubes to the cooling element lumen, and is used to circulate chilled fluid, such as water, saline, air, etc., through the lumen. The fluid can be continuously pumped or it can be intermittently pumped through the cooling element. Although three stimulation electrodes are shown, any number of electrodes greater than or equal to two could be incorporated into the pad. Muscle groups other than those in the leg can be stimulated using the systems and methods described herein.

Figure 8:
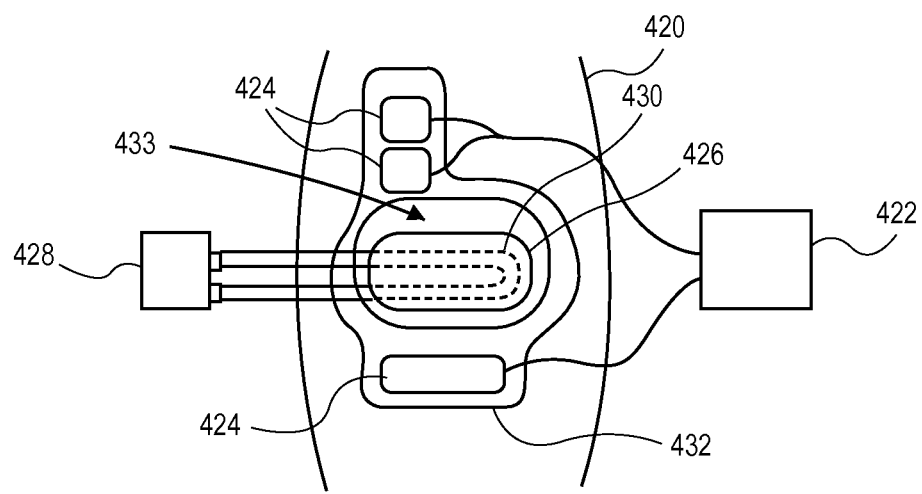
FIG. 8 shows a stimulation pad and a separate cooling element.

FIG. 8 shows an exemplary embodiment in which the system includes a stimulation pad and a cooling element that is not housed in the stimulation pad. In this embodiment, the cooling pad is a separate component that is placed on a person independently of the stimulation pad or stimulation electrodes. Stimulation pad 432 includes a flexible housing that includes stimulation electrodes 424. Electrodes 424 are in electrical communication with stimulation control unit 422. Cooling element 426 is not attached to simulation pad 432, but has lumen 430 that is in fluid communication with thermal control 428, which includes a pump. The pump can be, for example without limitation, a peristaltic pump. As shown, cooling element 426 is positioned between electrodes 424 in a window region 433 of the pad, thereby cooling superficial tissues and optionally creating a temperature gradient as described herein. In this embodiment window region 433 is an opening in the housing material, allowing cooling element to be disposed directly on the skin of the patient. In some embodiments the window element is not a "closed" window as in FIG. 8, but rather is a configuration of the pad that allows for a cooling element to be positioned between the electrodes and still be in contact with skin. For example, the open window could have a general "U" or "C" configuration that is configured to allow the cooling element to be positioned in contact with skin. Cooling element 426 and window region 433 are configured so that cooling element can be disposed within window 433 as shown.

Figure 9:
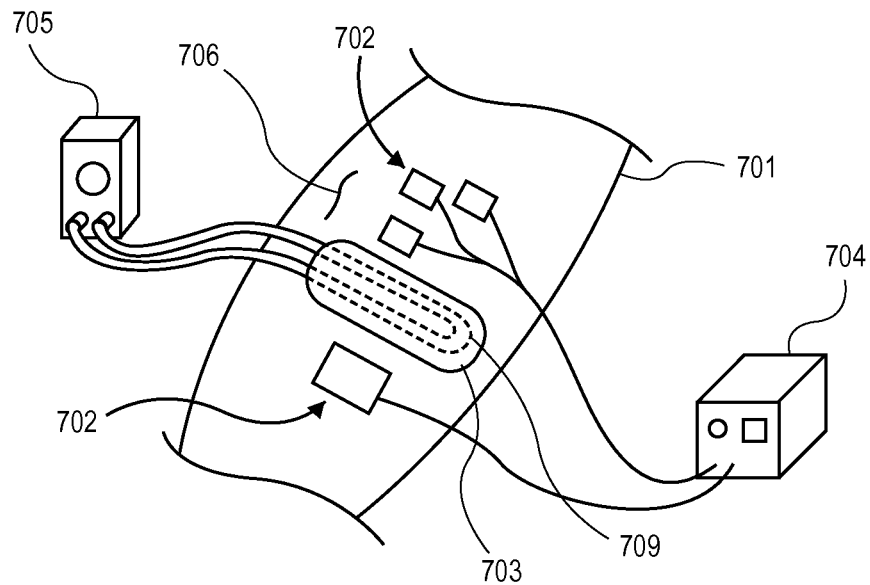
FIG. 9 shows discrete electrodes and a cooling element with a fluid lumen.

FIG. 9 illustrates an exemplary embodiment in which the electrodes are discrete from one another as well as from the cooling element. Stimulation electrodes 702 are positioned independently on leg 701 (although the system can be used on other body parts). Cooling element 703 includes hollow lumen 709 that is in fluid communication with thermal control 705, which includes a pump. Cooling element 703 is used to achieve surface cooling in the region between stimulation electrodes 702. Cooling element 703 is placed on the skin independently of the stimulation electrodes. The pump can pump a chilled fluid through lumen 709, either continuously or non-continuously, and can also include a fluid reservoir.

Figure 10:
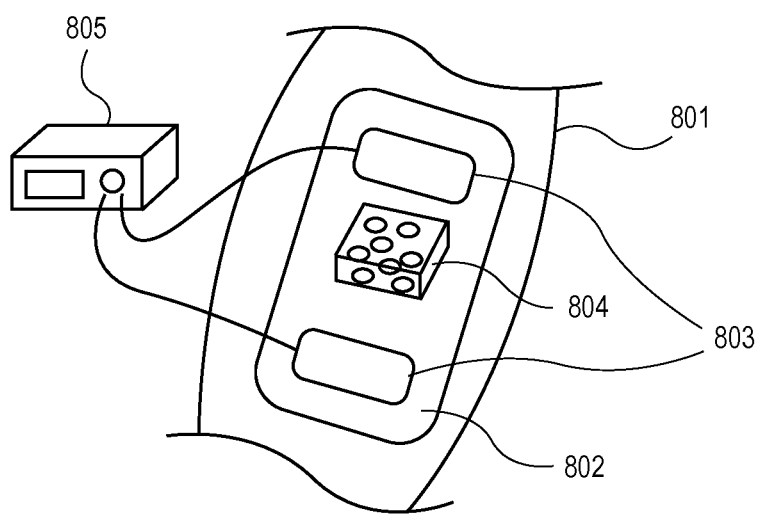
FIG. 10 shows a stimulation pad with an ice pack integrated therein.
Figure 11A:
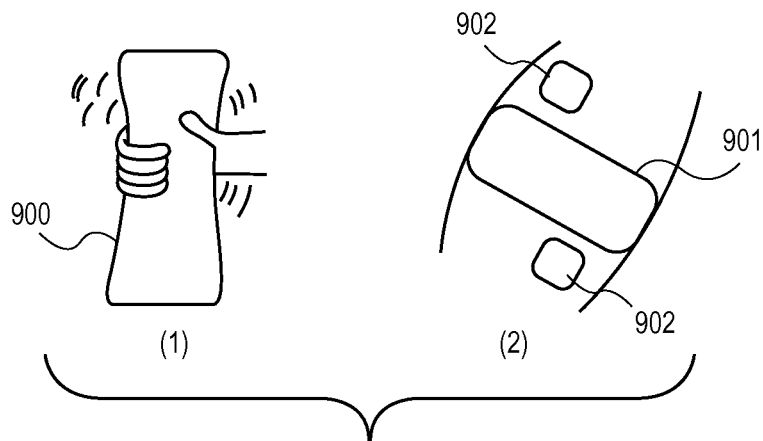
FIGS. 11A-11C show chemical cooling packs.
Figure 11B:
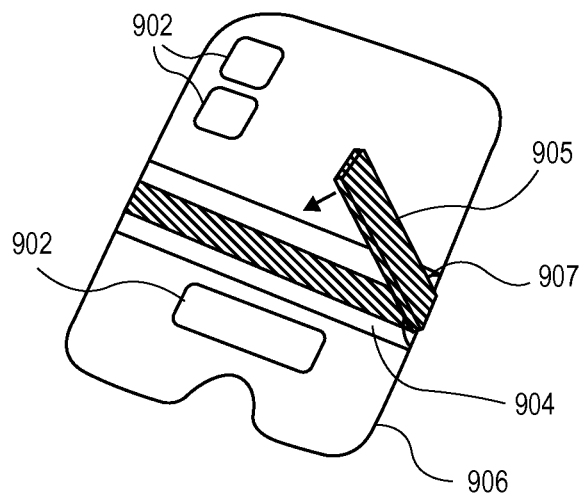
Figure 11C:
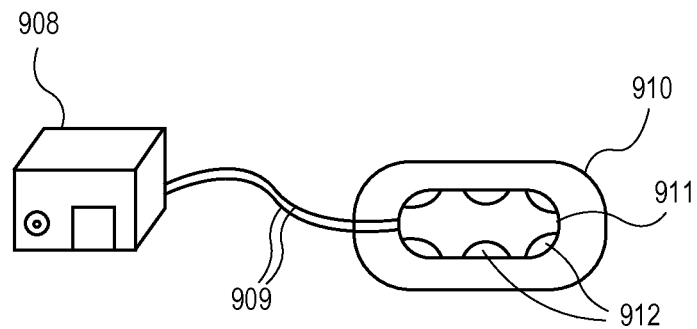

FIG. 10 illustrates an alternative embodiment of a NMES therapy system which includes a cooling element incorporated into a stimulation pad. System includes pad 802, which includes a fluid-tight and flexible ice water bath 804 in contact with the skin on partial portion of leg 801. Control unit 805 is in wired connection with stimulation electrodes 803, which are also incorporated into pad 802. Both the flexible ice bath and surface electrodes are part of stimulation pad 802, which fixes the relative positions of the two components of the system in an optimized configuration. The ice bath can alternatively be housed in its own pad, while the electrodes are housed in a separate pad. By using an ice bath, the temperature of the cooling agent (i.e., the ice) will naturally decrease over time as heat is transferred from the patient to the ice. Ice may therefore act as a time-dependent cooling mechanism and may help reduce the "pins and needles" sensation. FIGS. 11A-11C illustrate exemplary embodiments of NMES therapy systems that include a chemical cooling pack. In particular, the embodiments in FIGS. 11A-11C illustrate exemplary devices and methods of activation mechanisms for a chemical cooling pack to be incorporated with NMES therapy. In FIG. 11A(1), chemical cooling pack 900 is squeezed, thereby breaking an inner lumen to mix chemicals and provide a cold source. In FIG. 11A(2), cold source 901 is placed in the region of muscle stimulation in a location between stimulation electrodes 902. In FIG. 11B, stimulation pad 906 includes stimulation electrodes 902, cooling element receiving element 904, and integration element 905 configured to reversibly attach a cooling element to pad 906. The cooling element receiving element can be a window region in the pad ("closed" or "open"), it can be a reduced barrier section as described herein, or it could be a region of the pad between the electrodes. A cooling element in the form of a chemical cooling pack is described with respect to this embodiment, but other suitable cooling elements can be used with integration element 905 to secure the cooling element with respect to the patient. In this embodiment integration element 905 is a strap and hook mechanism. After positioning the cooling pack in the desired location with respect to the pad, the strap is pulled tight around pivot point 907. Pulling the strap exerts force on the chemical pack, breaking an inner lumen and mixing chemicals to create a cold source. The strap is then secured to itself using, for example, a Velcro strap, snap, or other securing mechanism. The cooling element is thereafter secured in place. The secured strap therefore reversibly secures the cooling element with respect to the patient, and depending on the pad configuration the cooling element is in direct contact with the patient or with the pad, or both. In FIG. 11C, the stimulation pad is in electrical communication with control unit 908. A cross-sectional view of the chemical cooling pack is shown. Wires 909 from control unit 908 extend through outer compartment 910 of the cooling pack and connect to resistive heating components 912 secured to inner lumen 911 of the cooling pack. At a desired time, control unit 908 sends electrical signals to resisting heating components 912 via wires 909, which melts portions of the inner lumen, causing the chemicals to mix and thereby create a cold source which can then be applied to the skin.

In some embodiments the cooling element is one or more cooling packs configured to interface with the control unit and/or stimulation electrodes, with or without integration into a larger stimulation pad subsystem. A cooling pack includes gel and ice packs, packs of phase-change material, chemical packs (e.g., ammonium nitrate/water mix or equivalent), or comprised of another suitable material. Preparation may differ depending on the type of cooling pack. For example, gel or phase-change material cooling packs may require that they be pre-cooled for a period of time, such as about one hour, prior to use while chemical packs may be activated immediately prior to use by mixing chemical components. Once prepared, cooling packs interface with other system components to provide surface cooling to tissues, such as by residing proximate to discrete electrodes on a skin surface or interfacing with a stimulation pad that includes integrated stimulation electrodes. In some embodiments, cooling packs may interface with electrodes in a region between electrode pairs or groups of electrodes in electrical communication with one another (e.g., between anode/cathode or the equivalent).

In some embodiments using cooling packs, cooling pack preparation is available at the point-of-care. This feature provides significant benefits to the practicality of a cooling-pack solution in a busy hospital environment. In some embodiments the preparation device is a cold-chamber that is configured to reside nearby, or proximal to, the control unit. For example, the cold-chamber and control unit can be configured to reside nearby one another on the same hospital cart. This allows for the two devices to be easily transported together and positioned in close proximity to a patient. In some embodiments the cold-chamber is a housing that is attached to the control unit housing. In some embodiments the cold chamber is integrated into the control unit such that the cold-chamber and the control unit are considered to be the same housing.

FIG. 12(a) illustrates an exemplary embodiment in which the devices and system integrate cooling chamber 288 into control unit 286. Control unit 286 communicates with stimulation electrodes via a wired connection 287 (only a portion of connection 287 is shown, and electrodes are not shown). As shown, cooling chamber 288 includes four cooling sub-chambers 290 configured to accommodate and cool a cooling pack 291. Only one cooling pack 291 is shown, but up to four packs can be positioned in the cooling sub-chambers. In some embodiments the cooling packs are, for example, gel, chemical, phase-change material, or other cooling packs. In this embodiment sub-chambers 290 are slots configured such that cooling pack(s) 291 can be easily inserted into and removed from the slot. In some embodiments cold chamber 288 has individual sub-zones for each sub-chamber 290 that may drive and maintain the pack temperature at desired settings. Each sub-zone can be configured to be individually set by the control unit to custom target temperatures. Alternative embodiments have sub-zones that include more than one sub-chamber but not all of the sub-chambers. Alternate embodiments do not use sub-zones and instead implement a bulk cooling approach where each cooling element is cooled to the same temperature.

Cooling chamber 288 includes four indicators 289 (for example, visual indicators such as LEDs), each associated with one of the sub-chambers 290. The indicators are configured to indicate whether or not a cold pack in the sub-chamber has been successfully regenerated with appropriate levels of thermal energy and therefore is at an appropriate temperature for use.

In some embodiments the control unit is configured to analyze information from one or more temperature sensors internal in the cooling chamber and determine if the desired temperature has been reached. If it has, the control unit controls the illumination of the indicator. In some embodiments the cooling chamber 288 has a single indicator that is configured to indicate that any and all cooling elements that may be positioned in a sub-chamber are at the desired temperature. The control unit can be configured to analyze sensed information from the cooling chamber. As an illustrative example, some embodiments may implement a red LED (or non-illuminated LED) when the cold pack is still in the regeneration phase and thus not ready for use, and a green LED when the cool pack has achieved a desired temperature and is ready for use.

In alternative embodiments an indicators is located directly on a cold packs. For example, the indicator can be a thermochromic sticker or label configured to indicate to the user that the cold pack is currently within a suitable temperature range for use with muscle stimulation.

FIG. 12(b) illustrates an embodiment of a stimulation pad 292 comprising stimulation electrodes 293 that is configured to interface with cooling pack 291 in a region proximate to the zone of stimulation after cooling pack 291 has been cooled in cooling chamber 288. Cooling pack 291 can be secured to the pad in any of the manners described herein.

FIG. 12(c) illustrates an embodiment of a cooling chamber that operates independently of a control unit. The cooling chamber in this embodiment can be in communication with any cooling element herein. Cooling chamber 294 includes two relatively large sub-chambers 295 accessible via separate entry doors 296. Each sub-chamber 295 is adapted to store and cool one or more cooling packs 297 (two are shown in phantom in one sub-chamber) and can have internal elements configured to hold the packs in a fixed position, such as in a flat and upright configuration. FIG. 12(d) shows an embodiment of a cooling chamber that cools stored cooling packs with a chilled circulating fluid. Fluid is stored in reservoir 299 and pumped in a circulating fashion through internal conduits (not shown) within cooling chamber 298 via, for example, a pump and internal lumens. The cooling chamber 298 can be any cooling chamber herein, such as cooling chamber 294 or 288.

In some embodiments, temperature and/or cooling protocols in the cold-chamber may be controlled by the control unit directly. In alternative implementations, these features may be controlled by software and/or circuitry specific to the cold-chamber. Low temperatures in the cold-chamber can be achieved using known methods, such as compressor/refrigeration systems, thermoelectric systems, circulating fluid systems, gas-exchange systems, or other appropriate methods. Some embodiments of systems and devices that implement a cooling-pack thermal mechanism will make use of a cold-chamber configured to cool individual or sets of cooling-packs that are removed from the chamber and subsequently interfaced with stimulation pads or other body-contact mechanisms. In some alternative embodiments, the entire, or substantially all of, stimulation pad assembly can be pre-cooled in a cold-chamber and then applied as a whole to a user. In these implementations, a cooling-pack may be pre-integrated into a pad, reducing the number of steps needed to deliver NMES.

Some embodiments that include cooling packs prepared with cold-chambers can include cooling chambers with that are configured with "quick-freeze" options or capabilities. In the event an operator has not prepared a cooling-pack or assembly with sufficient chamber-time prior to the desired time of use, power of the cold-chamber may be temporarily altered or re-purposed to rapidly cool a pack for immediate use. For example, if a cold-chamber has six sub-zones, cooling power to four of these may be temporarily re-allocated to rapidly cool cooling-packs located in the two remaining zones.

In alternative embodiments at least one of the control unit and the cooling chamber is built into a hospital bed. In this manner one or both of them would not need to be transported to the patient's room, providing easy point of care for the patient. The bed could have a wired connection enabling it to plug into a standard electrical outlet, providing power to one or both of the control unit and cooling chamber. If NMES is needed for therapy, medical personnel can access the cooling elements kept inside.

As set forth herein, some embodiments include a stimulation pad with one or more securing mechanism configured to allow cold packs or other cooling elements to interface with the stimulation pad as well as to secure the cooling element in place with respect to the cooling region. The securing mechanism can be a variety of mechanisms to secure the cooling element or elements to the pad. In some embodiments the securing mechanism is a strap, such as is described with respect to FIG. 11B above.

Figure 13A:
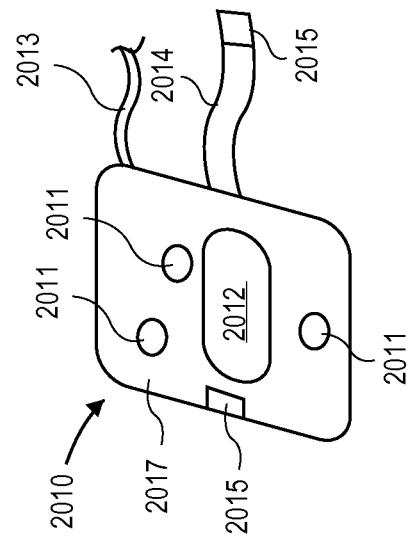
FIGS. 13A-13B illustrate an exemplary securing mechanism to secure a cooling element to a pad.
Figure 13B:
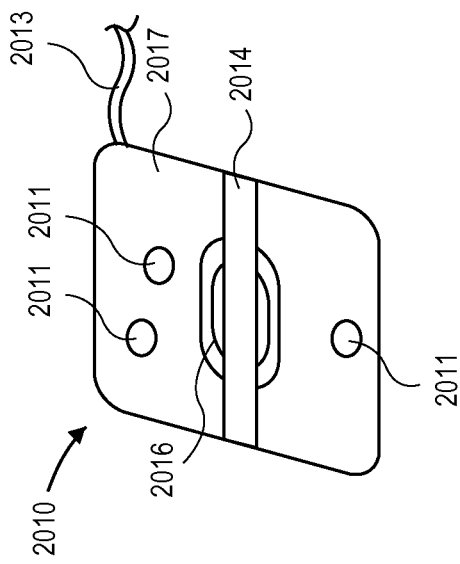

FIGS. 13A and 13B illustrate an exemplary pad that includes a securing mechanism configured to secure a cooling element to the pad. In this embodiment pad 2010 includes a housing 2017 that maintains electrodes 2011 in a predetermined configuration. Pad 2010 includes reduced barrier to thermal conductivity region 2012, which can be either a window that allows the cooling element to be completely or partially in direct contact with skin, or a region that includes pad material that is configured to a reduced barrier to thermal conductivity, examples of which are described herein. Pad 2010 includes wired connection 2013 configured to be secured to a control unit (not shown). The securing mechanism includes strap 2013 secured to pad 2010, with two securing elements 2015 configured to engage and be secured with respect to one another. For example, securing elements 2015 can be velcro strips, or a loop/strap configuration. FIG. 13B illustrates the system after cooling element 216 has been positioned in region 2012 and after strap 214 has been positioned over cooling element 216, the two securing elements 215 engaged with one another to secure them together and securing cooling element 216 in place with respect to the pad and with respect to the patient. In this manner securing mechanism allows the cooling element to be releasably secured to the pad and to the patient.

Figure 14A:
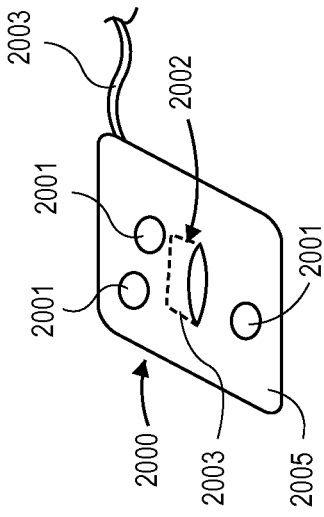
FIGS. 14A-14B illustrate an exemplary securing mechanism to secure a cooling element to a pad.
Figure 14B:
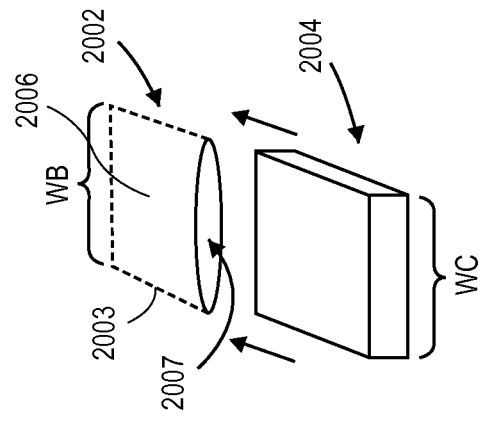

FIGS. 14A and 14B illustrate an alternative embodiment of a pad that includes a reversible securing mechanism to secure a cooling element in place with respect to the pad and patient. Pad 2000 includes housing 2005, or substrate as it may be referred to herein, electrodes 2001, wired connection 2003 configured to be in communication with a control unit (not shown), and securing mechanism 2002. In this embodiment securing mechanism 2002 is an elastic sleeve configured to hold a cold pack firmly in contact with the cooling region. The configuration of the sleeve with respect to the cooling pack allows mild positive pressure to be applied to the cold pack in order to facilitate thermal coupling and ensure adequate contact with the skin. In this exemplary embodiment, the elastic sleeve is smaller in an at-rest, or substantially unstretched, state, than the cold pack. Insertion of the cold pack into the sleeve will therefore stretch the elastic material of the sleeve, resulting in and providing a downward force on the cold pack, securing it in place with respect to the pad or with the skin directly. The downward force both secures the cooling element in place and also facilitates contact between the cooling element and either the skin directly or with the pad.

FIG. 14B illustrates a highlighted view showing only the securing mechanism 2002 and cooling element 2004 (e.g., a cooling pack), showing arrows which illustrate the direction in which cooling element 2004 is advanced to integrate it with the securing mechanism 2002. Securing element includes elastic material 2006 that partially defines slot or opening 2007, which is configured to receive the cooling element 2004 therein. The securing mechanism is configured like a pocket adapted to receive and secure a cooling element therein. Opening 2007 is large enough relative to cooling element 2004 to allow cooling element to be advanced therethrough, but small enough to secure the cooling element therein. In this exemplary embodiment the cooling element has a volume that is larger than the volume within the pocket, which is partially defined by the elastic material. In this exemplary embodiment the width of the pocket "WP" is the same or substantially the same as the width of the cooling element WC. It may be preferred that WP is substantially the same as or greater than WC, but WC could be greater than WP. The elastic material can be configured to be, prior to cooling element insertion, substantially in the plane of the pad housing. Material 2006 can be, for example without limitation, an elastomer, webbed material, etc. Other suitable materials can be used for the material 2006. If material 2006 is configured to breathe to some extent it may prevent or minimize condensation in the cooling region.

In FIGS. 14A and B, the pad can be configured with a reduced thermal barrier region where the cooling element is to be positioned. For example, the reduced thermal barrier region can be a window, or opening configured to allow the cooling element to be secured directly against skin. In alternative embodiments the reduced thermal barrier region is a portion of the pad that includes material, but provides less of a barrier to thermal conductivity to the skin than other regions of the pad.

In some embodiments the system utilizes a chemical mechanism to achieve superficial cooling. For example, the stimulation pad may have an open center portion, or window, such that the skin surface between the stimulation electrodes is exposed, examples of which are shown and described herein. After placement of the stimulation pad (or, in some embodiments, after placement of discrete electrodes), a chemical agent is applied to the exposed surface, reducing the temperature of superficial tissues. In some embodiments the agent is an agent that is adapted to be sprayed, wiped, or otherwise applied onto the exposed skin surface. Alternatively, a chemical mechanism may be part of or integrated into a separate system component (e.g., an instant cooling pack), that may be positioned in contact with superficial tissue.

In some embodiments the system includes a cooling element that is a thermoelectric element configured to cool the skin tissue as described herein. For example, the system can include a peltier device, examples of which are known for cooling (or heating if implemented). A thermoelectric device can interface with the control unit and/or the stimulation electrodes subsystems, whether or not the electrodes are integrated into a stimulation pad.

In some embodiments, thermoelectric elements and/or control units may also be configured so as to provide operator—or automatically—controlled mild therapeutic heating at various locations during and/or between stimulation treatments. For example without limitation, heating can be administered near the cooling region to reverse a cooling effect on the skin. This could be implemented into a feedback system, examples of which are described below, to manually or automatically modify superficial temperatures.

In some embodiments the control unit includes hardware, software, or firmware components configured to control both stimulation events and thermoelectric device operation. In addition to exemplary control unit components specified above, a control unit may also include an additional power supply for the thermoelectric device (or a more robust single supply for both stimulation and thermoelectric purposes), temperature control sensors and electronics configured to sense temperature of one or more device components, such as thermocouple hardware/software, and additional safety or operational components. A dedicated wired connection can travel from the control unit to the thermoelectric device, providing a means for both output, such as power, and input, such as importing sensed temperature information, etc. In some embodiments, a shared connection may be used that connects the control unit to the stimulation electrodes (or pad if one is used) and to the thermoelectric device(s). In some embodiments, the control unit may communicate wirelessly with a thermoelectric device housed remotely.

In some implementations, a thermoelectric device is configured to interface, reversibly or irreversibly, with a stimulation pad that includes one or more pairs of stimulation electrodes. FIG. 15(a) illustrates an exemplary system that includes a reusable thermoelectric cooling component that is configured to reversibly interface with a disposable stimulation pad that has been applied to a body. In FIG. 15(a), leg 301 is shown as an example target for NMES. Control unit 302 communicates with a stimulation pad 305 via cable 304. A second and separate cable 303 connects control unit 302 to thermoelectric device 307, which includes a plurality of thermoelectric elements 308, which in this embodiment have ovular configurations. Thermoelectric device 307 is configured to integrate with stimulation pad 305 in a predetermined cooling-interface zone 306, such as with a reversible securing mechanism. For example, the pad and thermoelectric device could have velcro regions at the corners.

FIG. 15(b) illustrates an exemplary thermoelectric device 309 that includes a housing and a plurality of thermoelectric elements 310 disposed therein. In this embodiment device 309 includes the elements 301 in a grid pattern, wherein the elements are small, rectangularly-shaped elements. Elements 310 could be in any pattern or non-patterned, and could also have any shape. The thermoelectric elements 310 are configured for the application of cold energy (e.g., by removing heat from the patient). One or more other regions 311 on the underside of the thermoelectric device 309 do not generate thermal energy directly, and are void of thermoelectric elements 310. This embodiment provides an exemplary benefit in that by using a plurality of small elements 310, as opposed to one or more elements that extend across a substantial portion of the device 309, device 309 is much better configured to conform to the surface of the body to which it is secured (even if there isn't direct contact between device 309 and skin). The spaces between elements 310 allow the device to flex and bend more than if the spaces are absent. These smaller elements may be better suited for conforming to rounded body parts. In some implementations, the different elements comprising an arrangement may be variably controlled such that spatial temperature gradients can be created, or such that regions of tissue requiring greater thermal energy can be properly cooled without over-cooling other regions. Variations of this embodiment may implement the use of elongated or rod-like elements, or may employ a single larger element covering the entire region of intended cooling.

FIG. 15(c) is a sectional view illustrating different layers of an exemplary thermoelectric device that can be used in any embodiment herein to apply cooling energy to the skin. Thermal coupling and/or distribution layer (for example, hydrogel layer) 312 is on the bottom (tissue-contact) side of the device. Atop this layer sits a layer 313 that includes one or more thermoelectric elements 235. A heat dissipation layer (e.g., phase change material, heat sink structure with or without fans, etc., examples of which are known in cooling devices) 314 sits atop layer 313 and is configured to safely dissipate the heat created on the non-treatment side of thermoelectric elements 325. An insulating layer 315 is provided to add extra isolation of heat generated during the thermoelectric process from operators of the device and/or recipients of the stimulation therapy. A label layer 316 resides on the top portion of the thermoelectric device and may be used primarily for aesthetic reasons, though several potential functionalities may be incorporated into this layer. For example, layer 316 can include components to facilitate integration and/or securement to a stimulation pad, which is described herein. These layers are merely illustrative and a thermoelectric device used herein not need include each layer. Additionally, other elements can be included in thermoelectric devices herein.

FIG. 15(d) illustrates how a thermoelectric device 318 connected to a thermoelectric driving unit (not shown) via cable 319 can be advanced into sleeve 317 prior to being placed proximate to the region of stimulation. In this embodiment the sleeve can be a part of the pad, such as an elastic sleeve as described herein, or the sleeve can be a separate component that is configured to interface with the pad. It may be easier to reversibly integrate a thermoelastic device with a pad by using a separate component such as a sleeve.

A thermoelectric component may contact the body directly or be placed in contact with an interface material, for example a hydrogel, water, foam, or other material suitable as an interface layer. In some implementations, the thermoelectric component docks with the stimulation pad and is secured through the use of buttons, snaps, straps, or other suitable connectors. In variation implementations, the thermoelectric component slides into a sleeve on a stimulation pad. In similar variations the thermoelectric component slides into a sleeve which then docks with a stimulation pad or alternatively is placed in direct contact with a person's body. It will be apparent to those skilled in the art that additional interface mechanisms are suitable, and that the implementations provided here are described by way of example.

Various embodiments employ thermoelectric components with different structures. In some embodiments, such as in FIG. 15(c), a multi-layer structure is employed. By way of example, a hydrogel or similar thermal coupling layer may reside at the bottom of the thermoelectric component on the side intended for contact with a person. This layer will serve to effectively couple thermal energy into the body. In some implementations, this layer may be fluid-based so as to distribute energy evenly over a curved surfaced. On top of this layer resides one or more thermoelectric elements (e.g., square plates). Atop of this a layer of phase-change material sits to help dispose of heat generated during the thermoelectric cooling process on the other side of the thermoelectric elements. In alternative embodiments, fans, heat-sink grids, or other suitable heat disposal/transfer means is integrated into one or more pad layers instead of a phase-change material layer. In a layer proximate to the heat dissipation layer sits an insulating material to keep heat from the heat dissipation layer away from regions that can be touched by a person or an operator, thus working to prevent burns. Some embodiments may also employ a top outer or label layer for marketing and finish-quality purposes.

In some embodiments, the one or more thermoelectric elements are configured so as not to cover the entire stimulation region. For example, cooling may be provided in regions between, surrounding, partially-covering, or adjoining the stimulation electrodes. In variation embodiments, thermoelectric elements may be large enough to cover the entire stimulation region, though the control unit may disable and/or limit thermal energy in any constituent thermoelectric elements in regions outside the intended region of temperature exchange. In further variation embodiments, thermoelectric elements may cover large regions of the body that include the stimulation region.

In some embodiments the cooling mechanism can include the use of gas expansion and devices configured for such uses. By decreasing the pressure of gas in a fixed volume, the temperature of the gas decreases and can be used to cool the superficial tissues. In some embodiments the use of gas expansion is incorporated into one or more different cooling mechanisms, such as a circulating fluid, a chemical cooling mechanism, and/or a thermoelectric cooling mechanism. Gas-expansion mechanisms can be configured to interface with the control unit and/or stimulation electrode subsystems, whether or not the electrodes are part of a stimulation pad. The gas-expansion mechanisms can be configured so as to provide surface cooling to a region proximate to the region of stimulation. Through the controlled release of gas, such as carbon dioxide, from pressurized chambers, thermal energy will be transferred in a way that may be used to lower temperatures of superficial tissues. The rate or timing of gas release and/or exchange may be controlled by the control unit, automatically or manually by the operator, or via hybrid mechanisms (examples of which are described below) for example where the operator selects a parameter (e.g., rate of gas release) on the control unit which then automatically carries out the necessary steps to assure conformity to this parameter. Compressed room air may also be used in gas-expansion embodiments rather than specific chemical compounds.

In some embodiments, a canister or reservoir contains a pressurized gas and a tube or other conduit through which gas may escape. The pressurized gas can be in a liquid state while under pressure. A valve in-line with the outlet tube controls the outflow of gas from the canister into the tube, which terminates at a nozzle that interfaces with a desired region of cooling. In some embodiments, this interface involves the nozzle being embedded or proximate to a gel or water zone in contact with the surface to be cooled. This gel or water zone may be stand-alone or may be integrated into another structure, for example a larger stimulation pad containing one or more pairs of stimulation electrodes. Compressed gas is released so that is expands at the nozzle, and thus the nozzle is the site of cooling. The gel or water zone then acts to dissipate the cold temperatures across the desired cooling region. In a variation of this implementation, a tube with multiple nozzles may be utilized to spread the cooling effect across a wider region to obtain more uniform cooling. In a further variation, multiple canisters may be used, each having one or more nozzles through which a gas-expansion process may take place. In a further variation, a single tube may have several off-shoot orifices which act similarly to full-termination nozzles to create a cooling zone with a wide coverage area. With any of these implementations as well as with others that will be obvious to those skilled in the art, other interface media aside from gel or water zones may be appropriate in alternative embodiments. For example, metallic thermal plates, foam materials, phase change materials, and other materials known in the art may be suitable as interface mechanisms in a number of the various implementations described herein.

In some embodiments of devices and systems that utilize gas-expansion mechanisms to provide thermal energy to tissue, a stimulation pad that includes one or more pairs of stimulation electrodes includes an interface mechanism configured to interface with a gas-expansion mechanism. In one implementation, a single- or multiple-use canister may integrate into a stimulation pad with internal tubing and nozzles built into one or more pad layers. In some implementations, the valve may be manually-controlled at the integration point. In other variations, the valve is also internal to the pad and is controlled via control signals from the control unit that dictate the operation of other mechanical control mechanisms. In further variations, multiple valves are available to control which portions of a pre-defined cooling zone receive cooling energy. In a variation embodiment, a tube or hose extends from a stimulation pad to a canister located remotely (for example, at the site of the control unit). In a further variation, no stimulation pad is utilized, and instead the canister system integrates with a patient interface located proximate to discretely-placed stimulation electrodes.

In some embodiments incorporating gas expansion mechanisms, the devices and systems as described above are reconfigured such that the gas expansion step of the process occurs within or near the exit point of the canister. A valve still controls outflow and a nozzle is present to vent gas, but the expansion and thus the temperature change occurs within or near the exit point of the canister. In this embodiment the canister itself is interfaced with the intended cooling zone to provide cooling via direct contact. In some implementations of this embodiment, the effective area of cooling may be increased by placing the cold canister in contact with a gel or water-based skin interface. In various implementations active spreading of the cooling area is accomplished through fluid, gas, or other types of heat-exchange media pumped through the cooling zone.

In some embodiments of the presently-disclosed devices and systems, circulating fluid mechanisms are used to interface with the control unit and/or stimulation electrode subsystems, with or without a pad. This may be accomplished in conjunction with multiple types of energy sources, for example thermoelectric coolers, ice water baths, compressors/refrigerants, and other suitable systems.

FIGS. 16($a$)-16($d$) illustrate exemplary embodiments of devices and systems with gas-expansion mechanisms that are configured to provide local cooling. In FIG. 16($a$), canister 471 contains a compressed gas 470 that can escape the canister via tube 472 when valve 473 is open. Gas expansion and thus local cooling occurs at nozzle 473, which is situated in a cooling zone 477 located proximate to stimulation electrode 475 that have been placed discretely on the body part 474 of the recipient of stimulation treatment. Cooling zone 477 can be part of a cooling pad that is placed on the subject between the electrodes.

FIG. 16 ($b$) illustrates an exemplary stimulation pad that includes a pre-defined integrated cooling zone 477. Stimulation pad 478 includes integrated electrodes 475 and a pre-defined, integrated cooling zone 477. The tube conveying gas 470 from canister 471, via valve 473, to the cooling zone contains numerous branches and nozzles 479 allowing for numerous points of gas expansion and cooling, thus spreading cooling energy over a greater spatial region of the patient.

FIG. 16($c$) illustrates an embodiment that includes multiple fluid canisters in communication with a pad. Multiple canisters 471 are used to simultaneously provide cooling energy to a cooling area integrated into stimulation pad 478. Gas expansion and thus cooling takes place at the nozzle 476 associated with each canister.

In the embodiment of FIG. 16($d$), control unit 481 has an interface means to allow for an integrated canister 471 and controls the release of gas by opening and closing valve 473. Compressed gas travels via tube 472 into pad 478 which includes an elongated, circuitously-shaped internal tube 480 that contains a plurality of orifices 471 along its length that act similarly to full-termination nozzles in the sense that they allow for gas expansion and thus cooling in that location. Tube 480 can be configured with any suitable configuration to increase the cooling area. In some embodiments the tube can have more nozzles in a particular region in which greater cooling is desired. For example, in a region more centrally disposed between electrodes, the pad can include a greater concentration of nozzles than in regions closer to the electrodes.

Figure 17B:
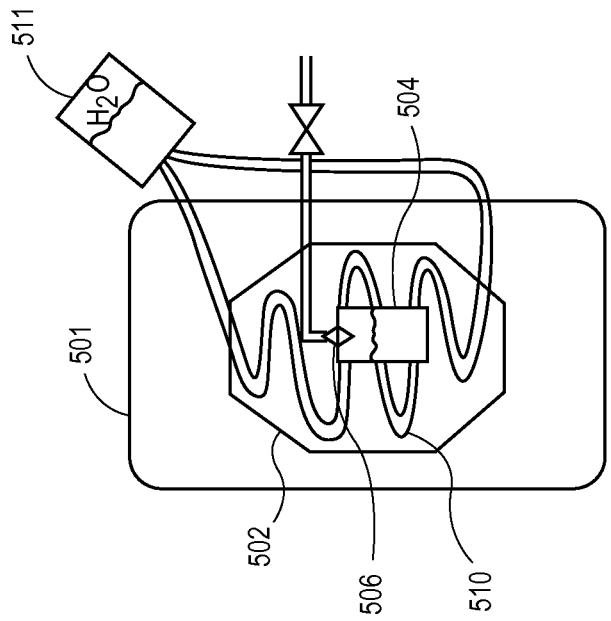
FIGS. 17(a)-17(b) illustrate embodiments of systems and devices that use controlled-release of compressed gases from integrated canisters to provide surface cooling to tissues during muscle stimulation.
Figure 17A:
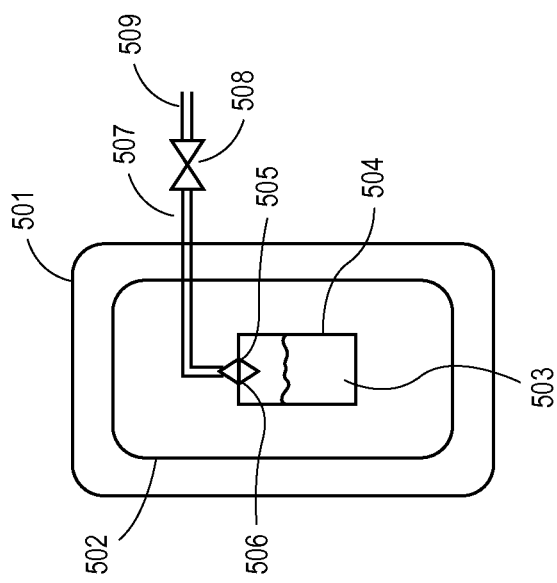

FIGS. 17(a) and 17(b) illustrate alternative embodiments of devices and systems that are configured with gas-expansion mechanisms to provide local cooling. In FIG. 17(a) stimulation pad 501 includes a pre-defined cooling zone 502 and at least one pair of stimulation electrodes (not shown), as well as other components not shown for simplicity. Canister 504 containing a compressed gas 503 therein is integrated with cooling zone 502. Canister 504 can be permanently integrated with pad, or the pad can accommodate reversible integration. For example, the canister can be positioned in a window region of the pad. Valve 508 controls outflow of gas from canister through primary nozzle 505, allowing for gas expansion at the canister escape point, resulting in cooling originating from location 506. Tubing 507 allows gas to vent out of secondary nozzle 509, though no or substantially no additional cooling or gas expansion occurs at this location.

Figure 18A:
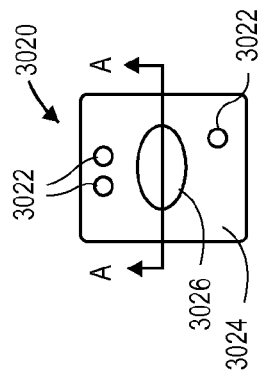
FIGS. 18A-18B illustrate an embodiment of a pad with a region that has a reduced thermal barrier to conductivity.
Figure 18B:
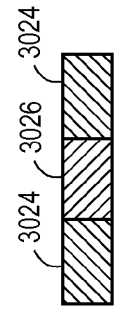

FIG. 15(d) illustrates an exemplary embodiment that includes first and second thermal devices, wherein the second thermal device is used to facilitate cooling that occurs with the use of the first thermal device. In the embodiment in FIG. 15(b), canister 504 integrates with cooling zone 502 of stimulation pad 501. Gas expansion and cooling occurs at location 506. Fluid reservoir 511 interfaces with a pump (not shown) to circulate fluid through a circuitous conduit 510 that extends throughout the cooling zone. Cooling occurring at point 506 will transfer in-part to the fluid moving through this region, cooling the circulating fluid. Chilled fluid circulating through the greater cooling zone 502 will expand the effective area of surface cooling As set forth herein, a stimulation pad with one or more electrodes can include a region with a reduced barrier to thermal conductivity to make more efficient the cooling of the superficial tissue in the region. The reduced barrier to thermal conductivity allows for superficial cooling to be preferentially or exclusively applied in a desired cooling region. In these embodiments an applied cooling mechanism will have fewer thermal barriers between it and a subject's skin than in other areas of the pad. As illustrated above, in some embodiments the pad includes a reduced barrier in the form of a closed or open "window," or "cut out" region. The cooling element can thus make direct contact with the skin without the pad providing a thermal barrier to conductivity. FIGS. 18A and 18B illustrate an embodiment of pad 3000 that can be used in any suitable system herein. Pad 3000 includes housing 3003, electrodes 3001, and window 3002. FIG. 18B illustrates the pad through section A-A in FIG. 18A, showing the housing 3003 and window region 3002. Any type of securing mechanism can be integrated into the pad as well.

Figure 19A:
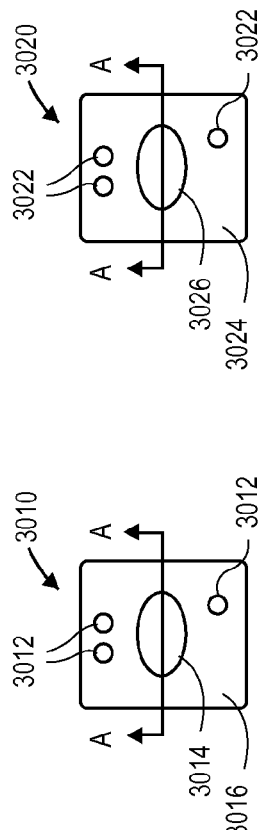
FIGS. 19A-19B illustrate an embodiment of a pad with a region that has a reduced thermal barrier to conductivity.
Figure 19B:
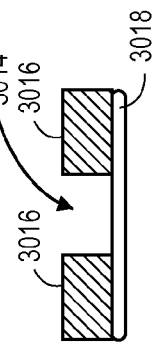

FIGS. 19A and 19B illustrate an exemplary embodiment in which the reduced barrier region comprises a window in a first layer of the pad, but wherein the pad also includes a backing that prevents the cooling element from contacting skin. Pad 3010 includes electrodes 3012 therein and reduced thermal barrier region 3014. As seen in FIG. 19B, region 3014 includes a window in housing layer 3016, but the pad also includes a backing layer 318, such as a hydrogel backing. A cooling element can be positioned within the window, but does not make direct contact with the skin. Similarly, a cooling element can be positioned over a region greater than just the window, but because of the window the tissue under the window can be cooled to a greater extent that tissue that is disposed under housing layer 316.

Figure 20A:
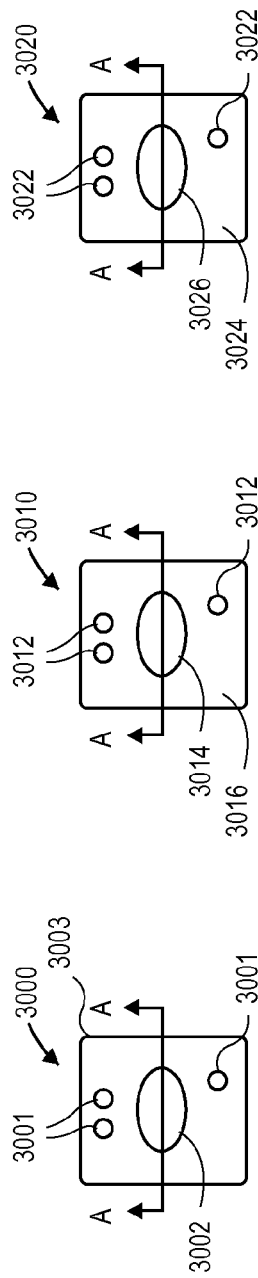
FIGS. 20A-20B illustrate an embodiment of a pad with a region that has a reduced thermal barrier to conductivity.
Figure 20B:

FIGS. 20A and 20B illustrates an embodiment in which a housing layer has a discontinuity that is filled with a thermally conductive element to facilitate superficial cooling via a thermal mechanism. Pad 3020 includes electrodes 3022 and housing 3024, and reduced barrier region 3026. As shown in the cross section A-A in FIG. 20B, the pad includes housing layer 3024, with a section removed, creating a discontinuity. The removed section has been replaced with, in this embodiment, a thermally-conductive hydrogel to facilitate superficial cooling. In other embodiment the pad can also include a backing layer such as in FIGS. 19A and 19B.

Figure 21A:
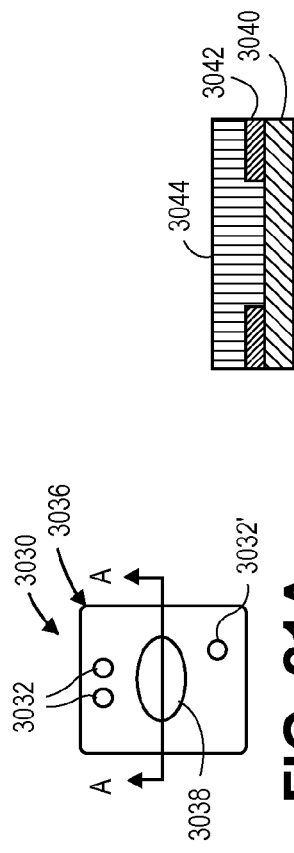
FIGS. 21A-21C illustrate an embodiment of a pad with a region that has a reduced thermal barrier to conductivity.
Figure 21B:
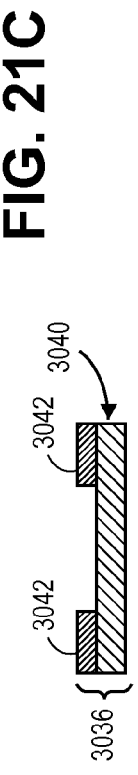

FIGS. 21A and 21B illustrate an exemplary embodiment wherein the pad has a reduced thermal barrier region with less insulation that in other regions of the pad. Pad 3030 includes electrodes 3032, housing 3036, and reduced thermal barrier region 3038. As shown in FIG. 21B, reduced thermal barrier region 3038 includes bandage layer 3040 and insulation layer 3042. In region 3038 there is an absence of the insulation layer, thus providing a reduced barrier to thermal conductivity in region 3038. In some embodiments region 3038 can include some thickness of insulation, but it can be less than in regions outside of region 3038.

Figure 21C:

FIG. 21C illustrates how a cooling element 3044 that at least partially overlaps with insulation layer 3042 can be applied to the pad, and insulation 3042 will cause less cooling in regions of the skin outside region 3038. Cooling element 3044 can in some embodiments cover more than or equal to half of the area of the body covered by the pad, though due to the pads selective insulation design meaningful cooling will only be achieved in the desired region proximate to the un-insulated or less-insulated region. In some embodiments the cooling element covers, or overlaps with, no more than about 5% of the area of the body covered by the pad, not more than about 10% of the area of the body covered by the pad, not more than about 15% of the area of the body covered by the pad, not more than about 20% of the area of the body covered by the pad, not more than about 25% of the area of the body covered by the pad, not more than about 30% of the area of the body covered by the pad, not more than about 35% of the area of the body covered by the pad, not more than about 40% of the area of the body covered by the pad, not more than about 45% of the area of the body covered by the pad, not more than about 50% of the area of the body covered by the pad, not more than about 55% of the area of the body covered by the pad, not more than about 60% of the area of the body covered by the pad, not more than about 65% of the area of the body covered by the pad, not more than about 70% of the area of the body covered by the pad, not more than about 75% of the area of the body covered by the pad, not more than about 80% of the area of the body covered by the pad, not more than about 85% of the area of the body covered by the pad, not more than about 90% of the area of the body covered by the pad, not more than about 95% of the area of the body covered by the pad.

In some embodiments the cooling element covers between about 1% and no more than about 95% of the area of the body covered by the pad. In some embodiments the cooling element covers between about 1% and no more than about 90% of the area of the body covered by the pad. In some embodiments the cooling element covers between about 1% and no more than about 85% of the area of the body covered by the pad. In some embodiments the cooling element covers between about 1% and no more than about 80% of the area of the body covered by the pad. In some embodiments the cooling element covers between about 1% and no more than about 75% of the area of the body covered by the pad. In some embodiments the cooling element covers between about 1% and no more than about 70% of the area of the body covered by the pad. In some embodiments the cooling element covers between about 1% and no more than about 65% of the area of the body covered by the pad. In some embodiments the cooling element covers between about 1% and no more than about 60% of the area of the body covered by the pad. In some embodiments the cooling element covers between about 1% and no more than about 55% of the area of the body covered by the pad. In some embodiments the cooling element covers between about 1% and no more than about 50% of the area of the body covered by the pad. In some embodiments the cooling element covers between about 1% and no more than about 45% of the area of the body covered by the pad. In some embodiments the cooling element covers between about 1% and no more than about 40% of the area of the body covered by the pad. In some embodiments the cooling element covers between about 1% and no more than about 35% of the area of the body covered by the pad. In some embodiments the cooling element covers between about 1% and no more than about 30% of the area of the body covered by the pad. In some embodiments the cooling element covers between about 1% and no more than about 25% of the area of the body covered by the pad. In some embodiments the cooling element covers between about 1% and no more than about 20% of the area of the body covered by the pad. In some embodiments the cooling element covers between about 1% and no more than about 15% of the area of the body covered by the pad. In some embodiments the cooling element covers between about 1% and no more than about 10% of the area of the body covered by the pad. In some embodiments the cooling element covers between about 1% and no more than about 5% of the area of the body covered by the pad.

Figure 22:
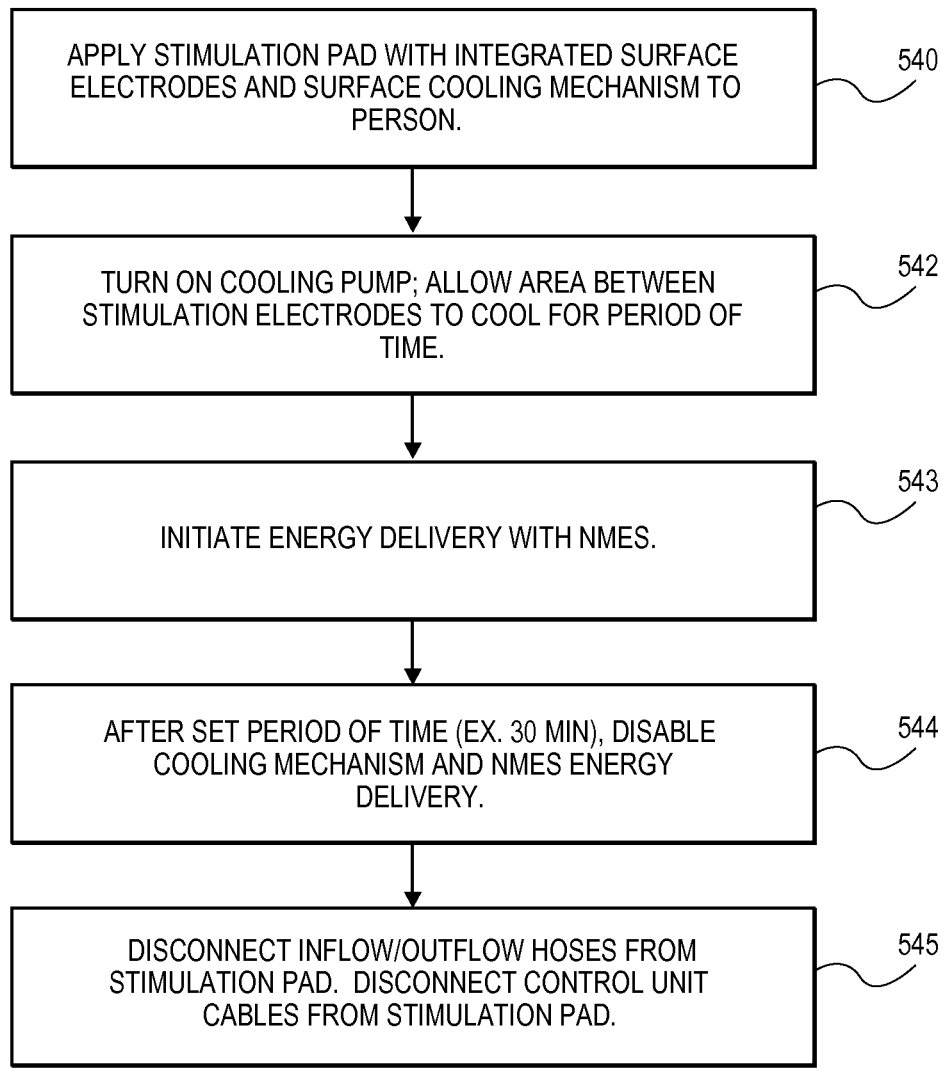
FIG. 22 shows an exemplary method of using a NMES therapy system.

FIG. 22 illustrates a merely exemplary embodiment of a method of using a system for NMES therapy. The order of the steps is not intended to be limiting, and some steps need not be performed. Other steps not shown can be included at any suitable time during the procedure. First, stimulation electrodes and a cooling element are applied to the surface of the skin at step 540. The electrodes can be discrete or they can be incorporated into a pad, and optionally with the cooling element. In step 540 the electrodes and cooling element can be positioned on the subject sequentially or simultaneously. In embodiments which include a cooling pump, the pump is turned on in step 542 which cools the area proximate, such as between, the electrodes for a given period of time. Electrical energy is then delivered to the patient through the electrodes at step 543. After a set period of time (e.g., 30 minutes) the cooling mechanism and NMES energy delivery are discontinued as shown in step 544. Finally, the inflow/outflow hoses are disconnected from the stimulation pad and the control unit is disconnected from the stimulation pad. Any of these steps may be optional or may be interchanged with other steps, or the order of the steps may be varied. For example, if the system includes a different type of cooling device, step 542 can be replaced with activating the cooling element to cool tissue. For example, if a cooling pack is used, step 540 includes position the cooling element in its cooling position relative the person. Cooling step 542 there inherently occurs as a result of step 540.

Application of the surface cooling can begin several minutes (e.g., about 5 to about 10 minutes) before NMES energy delivery begins. Alternatively, cooling can begin at substantially the same time that stimulation begins. Depending upon the embodiment of the devices and systems used to apply NMES, surface electrodes are applied to the body either before or after the cooling is initiated. Surface cooling can continue during NMES energy delivery. During this period, the temperature of superficial tissues may be held constant, or, in some embodiments, superficial temperature may continue to decrease during NMES. In some embodiments, surface cooling may be used intermittently during the NMES therapy session. Surface cooling may alternatively be implemented only prior to initiating NMES energy delivery. Surface cooling may alternatively be applied to the stimulation region after NMES energy has begun. For example, a 10 minute NMES warm-up period may precede a period of cooling with NMES therapy and/or a period of cooling followed by NMES therapy.

Figure 23A:
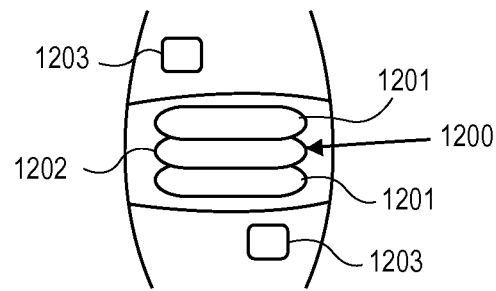
FIGS. 23A-23C show exemplary cooling elements with multiple cooling zones.
Figure 23B:
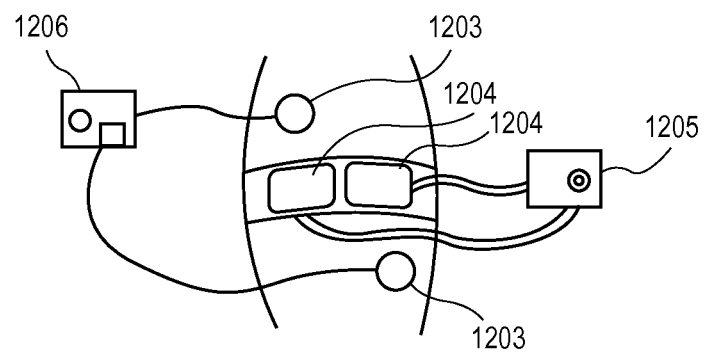
Figure 23C:
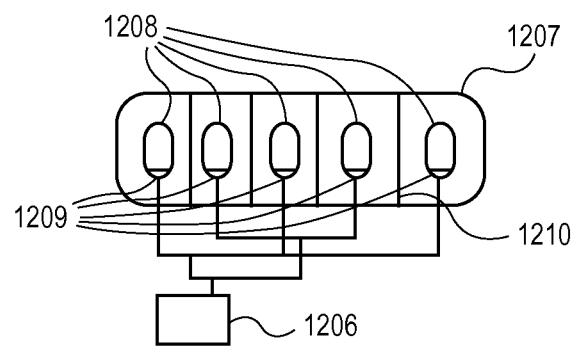

FIGS. 23A-23C illustrate embodiments in which the system includes a cooling element with a plurality of zones, or regions, of cooling. FIG. 23A shows a partial portion of a leg with cooling element 1200 which includes first cooling zone 1201 and second cooling zone 1202. Each of the zones is positioned between stimulation electrodes 1203. Each cooling zone may be controlled independently or dependently of the other zones. That is, the zones can be active or inactive independent of the other zone(s). The zones can be independent or dependently controlled by a control unit (not shown). In FIG. 23B control unit 1206 communicates with electrodes 1203. Pump 1205, driven either by control unit 1206 or independently controlled, circulates a cooled fluid through two or more separate zone housings 1204. The plurality of housings are not in fluid communication with each other. Valves or similar mechanisms can also be used to allow fluid to be directed to each housing individually or through multiple housings simultaneously. The embodiment in FIG. 23C utilizes a chemical cooling pack with multiple cooling zones. Outside compartment 1207 of the cooling pack houses more than one inner lumen 1208 that are sealed, or chemically isolated, from one another by compartmentalization elements 1210 (only one of four is identified). Each inner lumen may be broken by melting a portion of it by delivering energy from control unit 1206 to resistive heating elements 1209. Chemicals in the different zone of the cooling pack can be mixed at any time individually based upon instructions from the control unit.

For NMES therapy sessions expected to last for more than about 15 to about 30 minutes, there may be a concern of skin damage due to extended cold exposure. In some methods a first superficial region of tissue is cooled, and then a second, different, superficial region of tissue is cooled. By shifting the cooling regions, some risk of skin damage due to extended cold exposure may be reduced. In some embodiments the second region overlaps the first region. Given the relatively long re-warming time for tissue (after exposure to a cooling element has been discontinued) and extended period of increased NMES efficiency after cooling is removed from an area, adjusting the region of thermal transfer may allow for maintenance of an effective thermal gradient in tissues slightly deeper than the skin while avoiding potential low impedance electrical pathways on the skin surface. In embodiments that use a circulating cooled fluid as the cooling mechanism, the region of cooling may be alternated or changed by selectively opening and closing valves that control the flow of the fluid to certain regions of the cooling element. In embodiments that use a chemical instant cool pack as the cooling mechanism, a cold pack with a two-stage lumen may be used such that chemicals only mix in specific regions at specific times. Initially, the first stage inner lumen of the pack is broken to mix chemicals and cool one area. As the chemical reaction (and thus the cold source) ends in one area, the second stage of the lumen is broken to extend the thermal stimulus to a second area of skin. Variations may be provided using lumens with any number of stages to provide the desired amount and/or timing of thermal stimulus to one or more desired areas of skin. In embodiments that include thermoelectric devices as the cooling mechanism, the control unit may selectively activate specific zones of thermoelectric elements (independently or dependently of one another) by selectively sending energy or signals to each zone. For example, in FIG. 23A cooling zones 1201 and 1202 can be discrete (two or more) thermoelectric devices. The zones can be in communication with a cooling control unit, which is either housed with the stimulation control unit or is in a separate housing. The cooling control unit can be adapted to control the thermoelectric devices such that cooling zones 1201 and 1202 can be set to different temperatures, can be activated for different cooling times, etc. The thermoelectric devices can also have different sizes and shapes.

Figure 24:
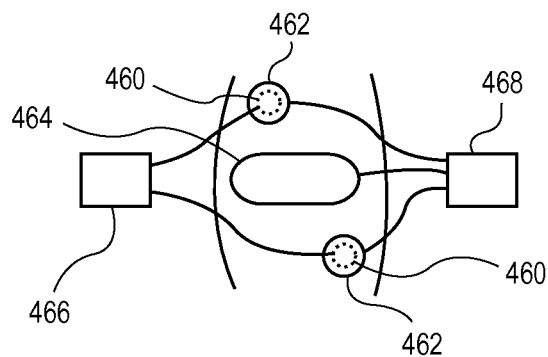
FIG. 24 shows a muscle stimulation system with cooling elements overlapping surface electrodes.

In some embodiments different regions, or zones can be subject to different degrees of cooling, which allows for different regions of skin to be subjected to different temperatures. As described herein, in some embodiments it may not be desirable to excessively cool tissue in the location where energy enters and exits the body (i.e., the location of the surface electrodes) because this increases local impedance and impairs electrode performance and sustainability without enhancing energy delivery to deep-lying muscle and/or nervous tissues. However, in some embodiments, it may be desirable to mildly cool (for example, on the order of about 1 to about 5° C.) tissue regions in the electrode location (or the electrodes themselves) to provide additional protection against the risk of burns. This mild cooling may provide additional burn protection without substantially raising tissue impedance in the region where energy enters or exits the body. In one or more other spatial zones located between the electrodes used for stimulation, more appreciable superficial cooling (for example, on the order of about 20 to about 30° C.) may be implemented to increase the efficiency of energy transfer to deep-lying muscle and/or nervous tissues. Any of the suitable embodiments described herein which describe a plurality of cooling regions, or zones, can be adapted to provide a plurality of different cooling zones, each of which (or some of which) can have a different thermal effect of different regions of tissue. For example, FIG. 24 illustrates an exemplary embodiment of a system which includes control unit 466 in communication with electrodes 460 (shown in phantom). The cooling element includes first cooling element 462 and second cooling element 464. Pump 468 is in fluid communication with both of the cooling elements. First cooling element 462 includes two discrete cooling elements positioned over electrodes 460. Second cooling element 464 cools the region between electrodes 460 more than first cooling element 462 cools the region (or also the electrodes) near the electrodes. This allows for a milder decrease in temperature in the region where energy enters and exist the body, but provides for a greater degree of cooling between the electrodes. Any other suitable cooling mechanism can be incorporated into this embodiment.

Figure 25A:
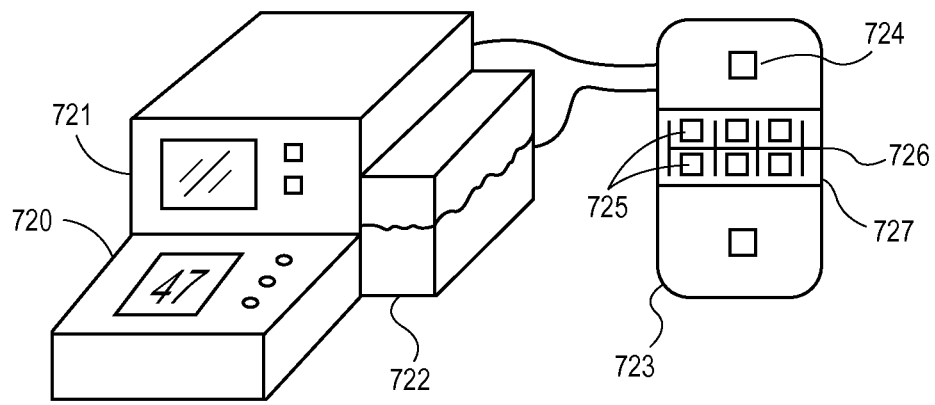
FIGS. 25(a) and 25(b) illustrate embodiments of systems and devices configured with hybrid mechanisms of generating thermal energy to be used in conjunction muscle stimulation.

In some embodiments herein the system is configured for hybrid cooling, in which the systems and devices include two thermal sources that are configured to cool the tissue. FIG. 25(a) illustrates an exemplary hybrid system. In FIG. 25(a), control unit 720 includes a thermoelectric controller 721 and a fluid reservoir/water pump system 722. Through various connections the control unit subsystems communicate with stimulation pad 723 that includes at least one pair of stimulation electrodes 724. Stimulation pad includes temperature change zone 727, which includes a grid of thermoelectric elements 725 as well as tubing 726 configured for circulation of fluid. Temperature changes in the zone 727 are achieved through simultaneous or independent operation of fluid circulation and thermoelectric subsystems. Operation of both thermal devices need not be required, but the system is configured to facilitate that if desired.

Figure 25B:
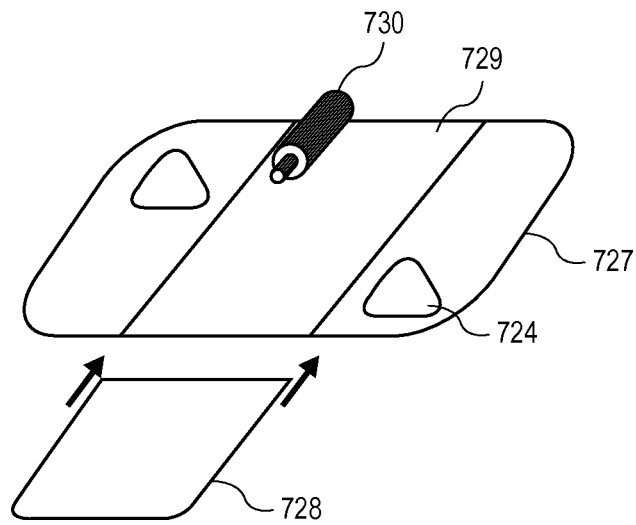

FIG. 25(b) illustrates an exemplary embodiment of a hybrid system. In FIG. 25(b), stimulation pad 727 includes at least one pair of stimulation electrodes 724. Canister 730 contains a compressed gas and integrates with cooling zone 729 of pad 728. The canister and cooling zone are configured to integrate with one another. Cooling pack 728, exemplary uses of which are described herein, also interfaces with cooling zone 729 after an operator slides it into a sleeve built into the pad, examples of which are described above. Cooling can be achieved through the use of the cold pack, and additional cooling energy to the region can be provided by expansion of gas from the canister, examples of which are described herein.

The different thermal mechanisms described herein can be mixed and matched to create any suitable type of hybrid system. For example without limitation, a cooling pack can be used with a thermoelectric device, a gas expansion device, or circulating fluid. In some embodiments a thermoelectric device can be used with a gas expansion device or circulating fluid. In some embodiments a gas expansion device can be used with a circulating fluid. These are merely exemplary combinations that can be used in a system. In some systems more than one of the same type of thermal mechanism can be used. For example, two different circulating fluid circuits could be used independently (i.e., not in fluid communication) to cool tissue as described herein. In alternative embodiments more than two cooling elements can be incorporated in a system or its method of use.

It may be desirable to maintain a relatively constant cooling temperature during a part of or the entire duration of the therapy. In these instances, a circulating cooled fluid, a chemical approach, or a thermoelectric approach may be more beneficial than using a cooling element such as an ice bag, cooling pack, or ice bath, as the cooling element will begin to inherently cool and will be unable to sustain the skin at a constant temperature over time. There may be additional advantages of the cooled fluid and chemical mechanisms of cooling that are related to workflow. For example, a cooling pump or instant chemical cooling pack can be kept conveniently in a storage area by a patient's bedside, such as on a hospital cart, and be activated when needed without requiring time associated with setup and storage that an ice bag, ice pack, or cooling pack may require. Additionally, ice bag and/or ice baths may be prone to moisture creation and/or leakage. Different types of cooling elements can therefore be used to adjust the temperature of the cooling element over time.

One or more cooling elements (or at least portions of the one or more cooling elements) is preferably held in secured contact with the skin. Movement of the region of stimulation caused by voluntary or involuntary muscle contraction or by other sources of motion could shift the position of or dislodge the cooling element from direct and efficacious thermal contact with superficial tissues. Some embodiments of the system therefore maintain desired thermal contact between the cooling element and the superficial tissues, even when such motion occurs.

Figure 26A:
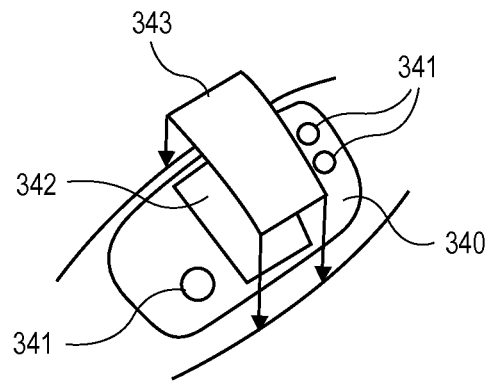
FIGS. 26A-26C show embodiments that allow for a cooling element to be held securely in place in the region of stimulation.
Figure 26B:
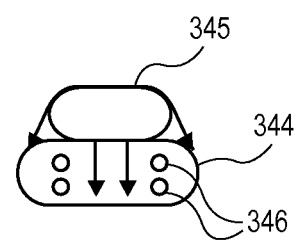
Figure 26C:
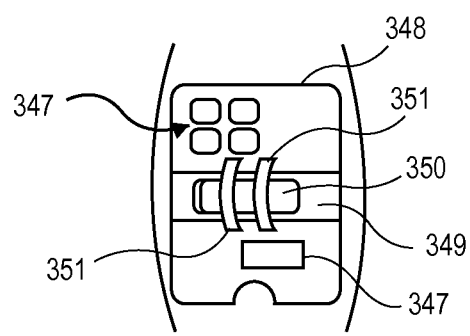
Figure 27A:
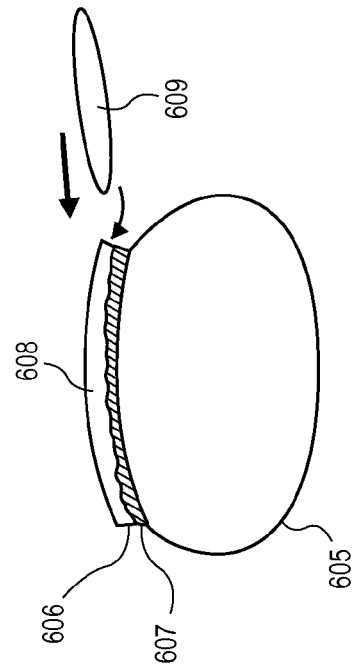
FIGS. 27(a)-27(d) illustrate interface mechanisms to facilitate coupling of thermal energy to tissue and embodiments of cooling zones.
Figure 27B:
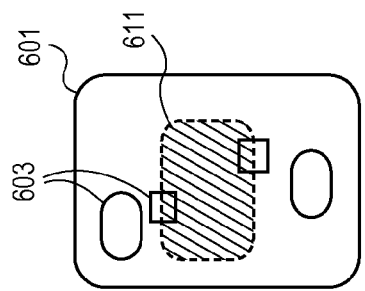
Figure 27C:
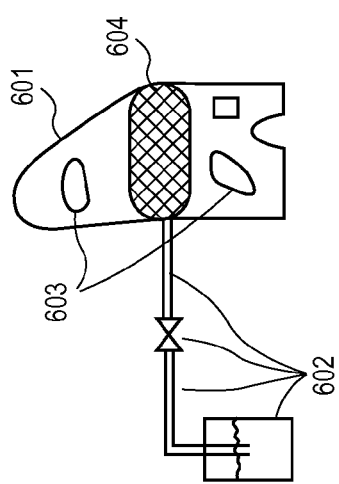
Figure 27D:
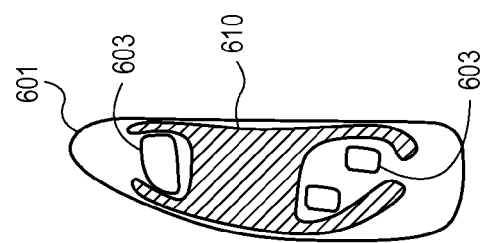

Some embodiments above describe exemplary securement mechanisms to secure the one or more cooling elements in place with respect to a pad. FIGS. 26A-26C illustrate additional embodiments of tightly securing the cooling element to the skin. In FIG. 26A the system includes stimulation pad 340, which includes three stimulation electrodes 341, cooling element 342, and weight 343. In one embodiment the weight is flexible and is similar in mass and flexibility to a sandbag. Cooling element 342 is positioned on the desired region of the skin and weight 343 is positioned atop the cooling element. Weight 343 secures cooling element 342 in place against the desired region of skin. In FIG. 26B, weight 345 sits atop cooling element 344 and is attached thereto using connectors 346, which are in the form of snap connectors. Other types of connecting elements may be used. In FIG. 26C, stimulation pad 348 comprises built-in stimulation electrodes 347 and a built-in cooling element 349. Weight 350, which can be flexible, sits atop cooling element 349 to exert downward pressure, and is held in place with the use of straps 351 that are adapted to couple to the stimulation pad on either side of the weight/cooling mechanism assembly. The straps can be elastic and can be configured to that when weight 350 is inserted, they will apply a downward pressure on the cooling element, assisting in maintaining contact with the skin. Alternative mechanisms of applying pressure to the cooling element may be used to maintain the cooling element is secured contact with the skin.

Tightly securing the cooling element to the skin may both maintain the cooling mechanism in a desired position as well as provide a tight seal between the cooling mechanism and the skin surface to minimize the build-up of moisture in the stimulation region. Alternative embodiments may include the use of mild adhesives or circumferential straps for maintaining the placement of the cooling element.

In some embodiments the NMES therapy system includes a way to prevent or minimize moisture from forming on the surface of the skin. When warm air comes in contact with a colder surface, moisture from the air may condense on the colder surface. Moisture on the skin surface may decrease the electrical impedance of the skin and also may pose a safety hazard during energy delivery. In some embodiments the pad on the skin includes several layers to avoid excess skin moisture during NMES with surface cooling. For example, in one embodiment the cold source is an inner layer contained within a compartment that is surrounded by a middle absorptive layer that may be thin enough so as not to serve as a thermal insulator. The middle layer can be a material similar to a paper towel, foam, or other suitable material. A thin outer layer that makes contact with the skin is comprised of non-absorptive material and surrounds the middle layer. The outer layer prevents moisture from forming on the surface of the skin.

In alternative embodiments, moisture build-up in the region of stimulation may be reduced by preventing warm air from reaching the cold source/skin interface, which can be accomplished by reducing or eliminating the air between the cooling element and the skin. Suction and/or vacuum pumps can be used remove the air. Applying sufficient pressure on the cooling element can also reduce the amount of air for circulation. Weights, straps, or other devices can be used to apply pressure to the cooling element. FIGS. 27(*a*)-27(*d*) illustrate alternative embodiments of NMES systems. FIG. 27(*a*) illustrates an example of a system with a distribution element configure to distribute applied cooling energy. In FIG. 27(*a*), stimulation pad 601 includes stimulation electrodes 603 and interfaces with gas-expansion system 602. Cooling zone 604 is comprised of a three-dimensional printed metal sponge, comprised of thermally-conductive material, to more evenly-distribute the cold energy provided by the gas-expansion across a wide coverage area. FIG. 27(*b*) is an exemplary embodiment that includes a distribution element configured to distribute applied cooling energy. In FIG. 27(*b*), thermal interface region 606 is positioned atop body part 605. Interface region as shown has two zones, an upper pocket zone 608 which remains empty when not being used and a fluid-like or gel-type lower zone 607 on the tissue-contacting side. Cooling element 609, such as a cooling pack, is inserted into or otherwise interfaces with thermal interface region 606 during use and occupies space 608, while lower zone 607 serves to distribute cooling energy across body part 605.

In FIG. 27(*c*), stimulation pad 601 includes electrodes 603. Cooling zone 610 has an irregular shape that partially encompasses electrodes 603. In FIG. 27(*d*), stimulation pad 601 includes electrodes 603. Cooling zone 611 extends over a coverage area that includes at least a portion of one or more electrodes. In this embodiment the cooling zone 611 is considered to overlap with one or more electrodes.

Figure 28:
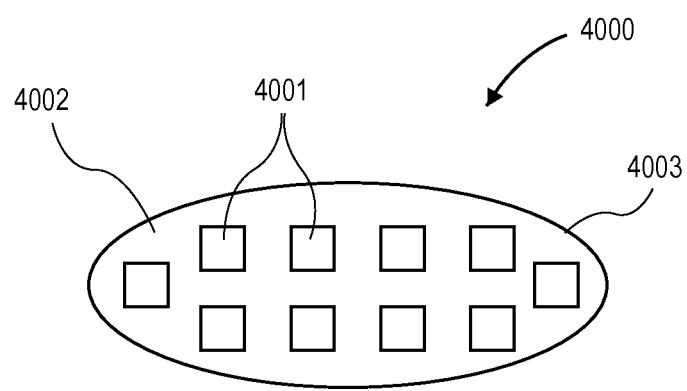
FIG. 28 illustrates an exemplary embodiment of a cooling element that includes first and second thermal sources integrated into a singular cooling element.

FIG. 28 illustrates an exemplary embodiment of cooling element that includes first and second thermal sources integrated into a singular cooling element. Cooling element 4000 includes an outer housing 4003 that contains gel matrix 4002 and a plurality of discrete phase change material elements 4001 (only two are labeled but 10 are shown) therein. Cooling element 4000 is more deformable than a rigid cooling element, and thus conforms better to body contours.

In some embodiments of the presently-disclosed devices and systems, vacuum techniques can be integrated into the systems, devices, and/or methods of use. Without wishing to be bound by any theory, it is believed that small magnitude negative pressure or vacuum may improve therapy efficacy due to vasodilation, improved contact, and/or improved heat transfer. In some implementations, vacuum is provided with a stimulation pad. For example, a hand-pump can be integrated into a pad, or used separately. In variation implementations, vacuum is controlled via the control unit and the use of other pumps or compressors. In some embodiments, the systems and/or devices are designed so as to interface with suction means integrated into a hospital room, for example suction means commonly used to clear lungs of mucous in patients.

In general, the NMES therapy systems have a stimulation control unit, in communication with the surface electrodes, that generates electrical energy and delivers it to the surface electrodes. In general, the control unit has a power source (e.g., a battery or isolation transformer for use with mains power), and can include any of the following: hardware components, software components, a voltage/current amplifier, a microcontroller, FGPA, timing circuitry, waveform generation circuitry, signal processing circuitry, and memory. In some embodiments the primary operation of the control unit can be provided by a microprocessor, field programmable gate array (FPGA), application specific integrated circuit, some combination of these mechanisms, or other suitable mechanism. When activated, the control unit generates electrical stimulation signals that are transmitted to the surface electrodes, which couple the energy into the body to stimulate muscle tissue.

Parameters of the electrical stimulation can be established prior to stimulation, and the control unit can be adapted to allow stimulation parameters to be adjusted at any time before, during, or after stimulation therapy. Parameters can be adjusted manually or the control unit can be configured such that parameters are adjusted automatically, which can occur according to a pre-established therapy protocol, or based on feedback signals monitored and sensed from the patient, discussed more below. Exemplary electrical stimulation parameters include, without limitation, the duration of therapy, stimulation pulse energy amplitude, etc.

In some embodiments the control unit includes a user interface to allow medical personnel to control the parameters of electrical energy delivery to the patient. The control unit can be adapted to allow a user to manually set (i.e., establish) the parameters of electrical stimulation, or it can be adapted to allow a user to adjust the parameters of electrical stimulation at any point during or after the therapy. The user interface can be housed in the control unit, or it can be a separate device similar to a remote control that is in communication with the control unit. The user interface can include buttons, knobs, dials, switches, etc., to control the parameters of energy delivery. The user interface may also include functionality to allow the user to test the operation of the control unit or any other component of the system to detect any errors or malfunctioning components.

In some embodiments the control unit is configured to automatically adjust one or more stimulation parameters based upon a preprogrammed therapy that includes portions with different parameters. For example, a therapy session can include a program in which the power automatically varies throughout the therapy.

In some embodiments the control unit is configured to automatically adjust stimulation parameters delivered to the stimulation electrodes based on optimization software in the control unit.

In some embodiments the control unit is configured to receive sensed patient signals that are generally sensed using one or more sensors positioned on or within the patient. One or more sensors can be used to sense parameters from the subject and provide feedback to the control unit, which can use the sensed information to adjust a parameter of the stimulation and/or an aspect of the cooling.

In some embodiments the system is configured to receive as sensed information one or both of information indicative of muscle stimulation and information indicative of tissue temperature. The system can be configured to use one or both of these types of sensed information to modify one or both of a muscle stimulation parameter and an aspect of thermal application.

In some embodiments, the control unit will make use of sensors and feedback control in order to modify at least one aspect of thermal energy delivery to reach target temperatures. This can include fine-tuning thermal delivery to reach a desirable thermal application. This allows thermal energy delivery to be optimized to improve therapy, or according to the needs of a particular patient. It also allows for energy delivery to be altered or maintained with a high degree of precision throughout an NMES session. In embodiments using thermoelectric or gas-exchange means of cooling, the control unit may fine-tune thermal energy delivery by adjusting the rate at which energy is delivered. For example, the control unit can modify the power/intensity delivered to a thermoelectric device or the rate of gas-release from a canister.

In embodiments using cooling packs, which are generally considered not to be under the direct control of a control unit once applied, a balloon, air baffle, or similar structure between the cooling pack and the person receiving therapy may be inflated and/or expanded to provide an air gap or separation between the cooling pack and the skin, adjusting both the contact pressure and contact time so as to adjust the amount of thermal energy delivered. In variation embodiments, the balloon or similar structure may mechanically lift a cooling pack away from patient contact when the desired cooling period is paused or ended and not in response to any sort of feedback mechanisms. These are examples of how a barrier to thermal conductivity can be increased during therapy by a cooling element generally not under the direct control of the control unit once applied to the treatment region.

In some embodiments sensors are configured to relay measured temperatures for display to the operator, for example with a display on the control unit or on the stimulation pad. In some implementations an alert, for example an audio alarm or a visual indicator (e.g., a flashing light), will be activated to indicate to an operator that a temperature measured by a sensor is out of a desired range.

In some embodiments incorporating temperature sensing, the stimulation pad or cooling mechanism includes an integrated temperature measurement sensor, such as a thermister, thermocouple, infrared sensor, photoacoustic sensor, or other suitable sensing device. This sensor is configured to relay sensed information, for example electrical information proportional or descriptive of the temperature of tissue (temperature of skin and/or of tissue at a specified depth) in sensing regions, back to the control unit. Electronics and/or software in the control unit may interpret this information and modify one or more aspects of the thermal application. For example, the control unit can activate or deactivate cooling via electrical or mechanical control mechanisms, for example ceasing power to a thermoelectric device. Alternatively, the control unit can modify an aspect of thermal energy delivery while the thermal energy is being applied. In some implementations this sensing and control/feedback process may happen continuously, while in others implementations it may occur at discrete intervals. In some embodiments the sensing occurs automatically under the control of the control unit, while in some embodiment it is under at least the partial control of the operator and may be initiated through commands on a user interface on the control unit.

In some embodiments the sensor can include a temperature sensor configured to monitor the temperature on the skin of the patient. The control unit can be configured to continuously or periodically receive the sensed temperature and a control algorithm can compare the sensed temperature with a reference temperature to determine if the sensed temperature is higher or lower than the reference temperature. Based on the comparison, the therapy may require that the cooling element be activated, deactivated, or adjusted to increase or decrease the temperature of the skin. The degree of cooling can be adjusted manually, or the control unit can have software built-in to modify the cooling protocol to control the skin temperature. Monitoring the skin temperature can provide an indication of the temperature gradient created in the tissue and therefore provide an indication if the gradient is sufficient to deliver a sufficient percentage of energy entering the patient to deep-lying muscle tissue. Thus, temperature is an exemplary patient parameter than can be sensed to control the amount of surface cooling by the cooling element, examples of which are described herein.

In some embodiments temperatures sensors are used to modify one or more aspects of muscle stimulation. For example, if the tissue temperature is not at a desired minimum temperature, the power of the stimulating energy can be increased to compensate for a lack of increased impedance in the superficial tissue.

In some embodiments the sensor includes a sensor to sense the degree of muscle stimulation, or contraction. Sensing muscle contraction can be performed with, for example without limitation, an EMG. When the sensor is adapted to sense muscle contraction, the sensed parameter can be any parameter indicative of the amount of muscle contraction. The control unit can be adapted to receive the sensed parameter indicative of muscle contraction and use this information to control the operation of the cooling element or to control the electrical stimulation. For example, if the sensed parameter indicative of muscle contraction indicates an insufficient amount of contraction, it may be desirable to either increase the cooling effect on the surface of the skin (to increase the superficial skin impedance) or to increase the amount of electrical stimulation, or a combination of the two. The response to the sensed parameter can be a manually adjusted (e.g., via a user interface) or it can be automatically controlled by the control unit. Exemplary muscle sensors that can be incorporated into the NMES therapy devices and methods herein can be found in application Ser. No. 12/497,230, filed Jul. 2, 2009, which is incorporated by reference herein.

In some embodiments one or more sensors are coupled to the person receiving NMES and are adapted to record data indicative of muscle contraction, and feedback control systems within the control unit are used for closed-loop optimization of stimulation energy waveforms and/or closed loop optimization of aspect of thermal energy application.

In some embodiments the system can use one or both of temperature sensing and muscle contraction sensing to modify one or more aspects of thermal energy delivery. As set forth above, the systems can be hybrid systems in that they can utilize one or more thermal source to fine-tune, or modify the tissue temperature. For example, in the embodiment in FIG. 25(a), cooling can be initiated with a cooling fluid being circulated through a conduit. As the tissue temperature is sensed, the control unit can, either automatically or manually, modify as aspect of thermal energy being delivered from the thermoelectric device to control the tissue temperature. For example, if the sensor indicates the tissue is too warm, the thermoelectric device can be activated or power can be increased to further cool the tissue. Alternatively, if the sensed information indicates the tissue temperature is too cold, the thermoelectric device can be used to apply heat to the skin until the temperature is sensed to be within a desired range or at a certain threshold. In this manner a hybrid system can be used to provide fine-tune control of the tissue temperature to improve the efficiency and effectiveness of the NMES therapy.

The control unit can be configured to activate, or initiate, a cooling element. In one exemplary embodiment, local tissue cooling in the stimulation region is initiated after several minutes of "warm-up" stimulation energy is applied to the subject. It may be beneficial if the system does not require a care provider to return and make adjustments after the "warm-up" stimulation energy such that cooling is automatically initiated at a pre-established time during a therapy procedure.

In embodiments that use a circulating cooled fluid (examples of which are described herein) to create a temperature gradient, the control unit can be in communication with a pumping element that controls the flow of fluid to the cooling element. The control unit therefore controls the skin temperature of the patient. The control unit can be adapted to activate the cooling mechanism at a predetermined time or at a feedback determined time.

Other embodiments use an instant chemical cooling pack (such as urea-based or ammonium-nitrate/water packs that are commercially available) that activates when an inner lumen is broken, causing two substances to mix and chemically react. Examples of such embodiments are described herein. Electrical current generated in the control unit can be used to melt or break predetermined regions of the inner lumen of the cooling pack, causing the substances to mix.

The system, such as in the control unit, can also include one or more memory units to store, for example without limitation, algorithms used to carry out the functionality of the NMES therapy, therapy protocols, sensed patient parameters, stimulation parameters, and/or cooling parameters. The memory can be in any of the following forms: RAM, ROM, EEPROM, volatile memory, non-volatile memory, or any combination thereof. The memory units can be in communication with a processor to carry out the NMES therapy.

One or more processors in the control unit can be coupled to a clock for timing and synchronizing various aspects of the therapy.

The control unit can also include a communication interface adapted to communicate with a remote device such as, for example without limitation, a personal computer or a network to provide for communication of data, programming commands, etc. Communication can be carried out using conventional wireless protocols, such as telemetry, inductive coil links, RF links, other electromagnetic links, magnetic links, infrared links, optical links, ultrasound links, etc. The communication interface can include both a receiver and a transmitter to allow for two-way communication so as to allow for providing software updates to the control unit, transmit stored or real-time data, transmit inputs from medical personnel, etc.

The control unit can be used to control various aspects of the therapy even if not specified described herein. The control unit may be a single housing or it may be more than one housing, any number of which are in communication.

Figure 29:
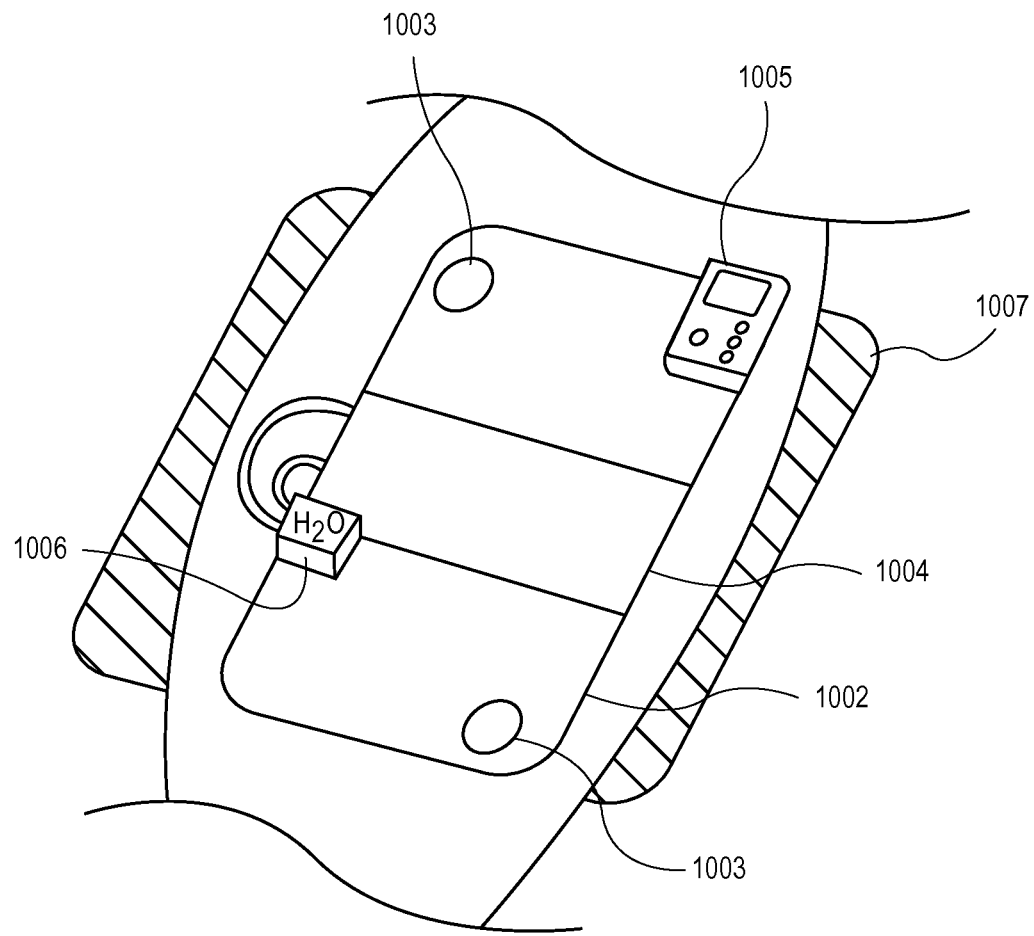
FIG. 29 shows an embodiment with an optional heating element disposed on a posterior portion of a leg.

In some embodiments the systems include a heating element in addition to a cooling element. While the cooling element is used to decrease the temperature of tissue, the heating element is used to increase the temperature of issue. In FIG. 29 heating element 107 is positioned on the posterior side of leg 1001 (or the leg presses against the heating element when the patient is lying on a table), while stimulation pad 1002 is positioned on the anterior portion of leg 1001. Stimulation pad 1002 includes cooling element 1004 and stimulation electrodes 1003. Control unit 1005, as well as and pump and fluid reserve 1006 are also incorporated into stimulation pad 1002. Surface cooling is applied by cooling element 1004 as described herein. Heating element 1007 is positioned to apply surface warming near the hamstrings and/or gluteals, although the system can be applied to other muscles. The posterior warming acts synergistically with the anterior surface cooling to increase the temperature gradient between deep-lying muscle tissue and superficial tissues on the anterior side of the leg, increasing the efficiency of electrical current deposition to muscle tissues. Secondly, the warming can help maintain core body temperature within normal levels. Prolonged surface cooling may change temperatures near large blood vessels, which may in turn cool blood and thus lower internal core temperature. A posterior heating element may help offset any cooling induced changes in core temperature by warming tissues near large vessels, without decreasing the temperature gradient on the anterior portion of the leg. The warming element can be coupled to its own control unit to control the temperature of the heating element. The warming element can be similar to a heating pad.

Figure 30A:
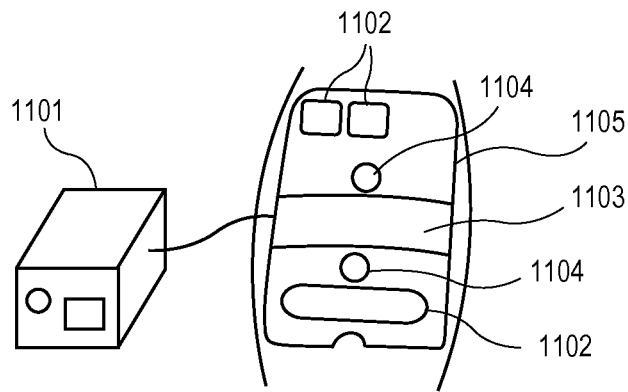
FIGS. 30A-30C show an embodiment with an ultrasound transducer.
Figure 30B:
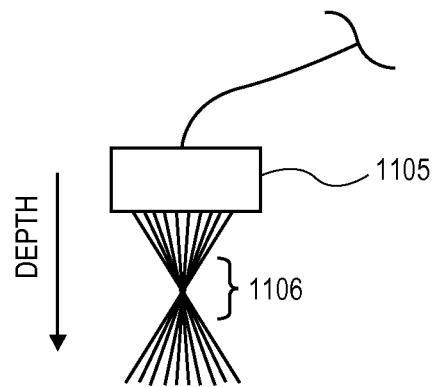
Figure 30C:
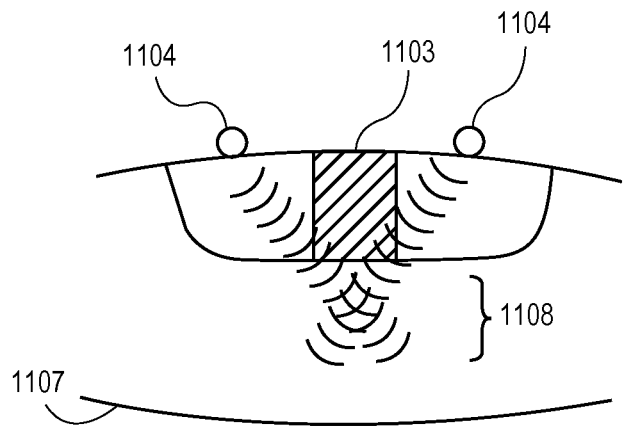

FIGS. 30A-30C illustrate alternate embodiments which comprise an ultrasound transducer. In FIG. 30A, control unit 1101 is in electrical communication with stimulation pad 1105, which includes stimulation electrodes 1102, cooling element 1103, and two ultrasound transducers 1104. FIG. 30B shows the acoustic energy distribution from focused ultrasound transducer 1105, with the peak spatial distribution of energy in the beam occurring in the focal region 1106. Tissue heating may occur primarily in the focal region, as in other regions the energy is too spread out spatially to significantly raise temperatures. FIG. 30C is a cross-sectional side view of limb 1107 being treated with NMES therapy. Ultrasound transducers 1104 transmit acoustic energy from the surface of the skin through superficial tissues, with a focus in deeper regions of tissue 1108.

Operated by the control unit or other control device, transducers may use relatively low frequency ultrasound energy (e.g., from about 1 to about 4 MHz) with an electronic and/or concave lens focus to a depth appropriate for the muscle group being stimulated. Ultrasound energy may be partially absorbed by tissue through which it propagates, and this energy may be converted to heat. Due to the focal nature of ultrasound, it is possible to deposit the overwhelming majority of the energy in the focal region while depositing minimal energy in more superficial regions of tissue. Accordingly, deeper tissues in the focal region may be warmed without significant warming of superficial regions. This method may strengthen the thermal gradient that is produced by the superficial cooling mechanism, as well as help ensure that the core body temperature does not drop too low.

EXAMPLE

A research study has investigated the NMES therapy with skin cooling disclosed herein. Twenty healthy volunteers were recruited. The first group (Group 1) of ten volunteers included all-corners (median age 44 years, range 22-70 years, median BMI 25.0, range 22.0-38.3). The second group (Group 2) of volunteers consisted entirely of clinically obese (BMI>30.0) individuals (median age 53 years, range 25-75 years, median BMI 32.4, range 30.1-39.6). An additional research study that recruits critically ill patients is underway, and preliminary results are available.

In the first study, volunteers had their posture stabilized and muscle stimulation electrodes were applied in a mirror image configuration on each thigh in the region of the quadriceps. A medical dynamometer was placed over each ankle. During muscle stimulation, the quadriceps contracts, causing the leg to extend. The medical dynamometer reads this leg extension force. Leg extension force for a fixed (constant) amount of stimulation energy is a proxy for the number of muscle motor units recruited during stimulation with that amount of energy, and thus serves as a good descriptor of muscle stimulation efficiency. After baseline measurements of muscle strength in each leg were made, one leg was randomly chosen to receive an ice bag placed on it in the region between stimulation electrodes, while on the other leg a room-temperature control bag was placed. Measurements of leg extension force were made in each leg at 3 minute intervals. After 20-30 minutes of cooling, both ice and control bags were removed from the legs, and measurements were continued during the re-warming period.

In the study, muscle stimulation was provided as a pulse train composed of a series of asymmetric, biphasic square waves with pulse durations of 300 microseconds and at repetition rates of 40 Hz. Pulse trains lasted for 5 seconds with 1 second energy ramp up and ramp down times (i.e., 3 seconds of maximum energy delivery), and were followed by resting periods of at least 10 seconds. The maximum current delivered by each stimulator channel to each individual ranged from about 30 to about 80 mA.

In some embodiments the frequency content of the individual pulses is about 10 kHz or lower. In some embodiments it may be about 5 kHz, while in some embodiments it may be about 1 kHz. In some embodiments the pulse repetition rates are about 30 Hz or greater. In some embodiments the pulse repetition rates are between about 30 Hz to about 50 Hz. In some embodiments the energy is delivered with an alternating series of on (during which pulses are applied at a given repetition rate) and off times (during which no pulses are applied). In some embodiments the on times last for about 5 seconds to about 10 seconds. In some embodiments the off times last for about 10 seconds to about 20 seconds.

This study showed the immense usefulness of the systems and methods described herein. Leg extension force (and thus muscle stimulation efficiency) increased in the experimental leg during the cooling period in all 20 volunteers. The average peak increase in extension force from baseline achieved with superficial cooling in the experimental leg was 69.9% in Group 1 and 94.8% in Group 2. This larger increase in the clinically-obese group shows the extreme efficacy of the NMES therapy with cooling for improving results in challenging stimulation cases (i.e., persons who generally require the maximum energy allowed by regulatory and/or overseeing body safety standards is required to achieve even mild muscle contraction). The large increase in Group 2 is especially significant because it allows for muscle contraction to go from a level that is not strong enough to prevent atrophy, to one that is useful for preserving muscle strength and improving functional outcomes. Accordingly, the presently disclosed devices, systems, and methods will enable this group of individuals to receive significant or improved benefit from NMES therapy.

Relative to the control leg, the mean 9-minute average increase in extension force achieved with superficial cooling in the experimental leg was 52.6% relative to baseline, indicating that increases in stimulation efficiency are sustainable over a significant period of time. Overall, muscle contraction strength increases achieved with superficial cooling were determined to be extremely statistically significant ($p<0.0001$) with a paired t-test analysis.

Figure 31:
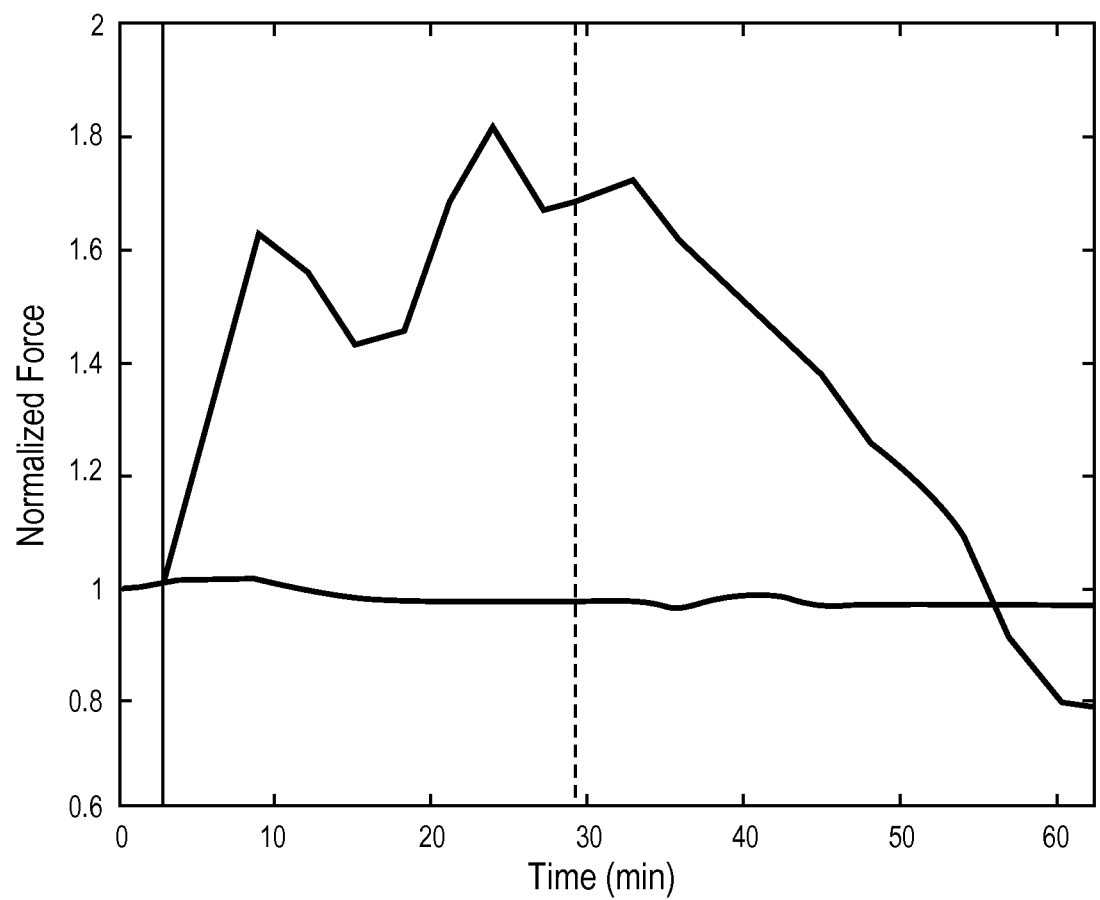
FIG. 31 shows empirical data from a human volunteer.

FIG. 31 shows empirical data from a human volunteer from the first study. The ordinate axis shows the maximum leg-extension force produced (as measured at the ankle by a dynamometer) by stimulation of the quadriceps muscle, normalized by baseline measurements for each leg. The electrical current settings on the NMES device were held constant throughout the measurement period. Time is shown on the abscissa. The measurements at time t=0-6 min were taken as baseline readings. At time t=6 min (solid vertical line), a waterproof bag containing ice cubes was used to cool superficial tissues on the experimental leg (upper data trace) in the location between the stimulation electrodes, while a room temperature bag was placed on the control leg (lower data trace). Both ice and room temperature bags were removed at time t=29 min (dotted vertical line). As shown, the improved efficiency of electrical current transfer to the quadriceps muscles (as evidenced by force of leg extension) is still evident more than 20 min following removal of the thermal stimulus. In addition to showing increased muscle stimulation (and increased contraction) FIG. 17 supports the functionality of cooling applied to superficial tissues intermittently during NMES or only prior to NMES.

Figure 32:
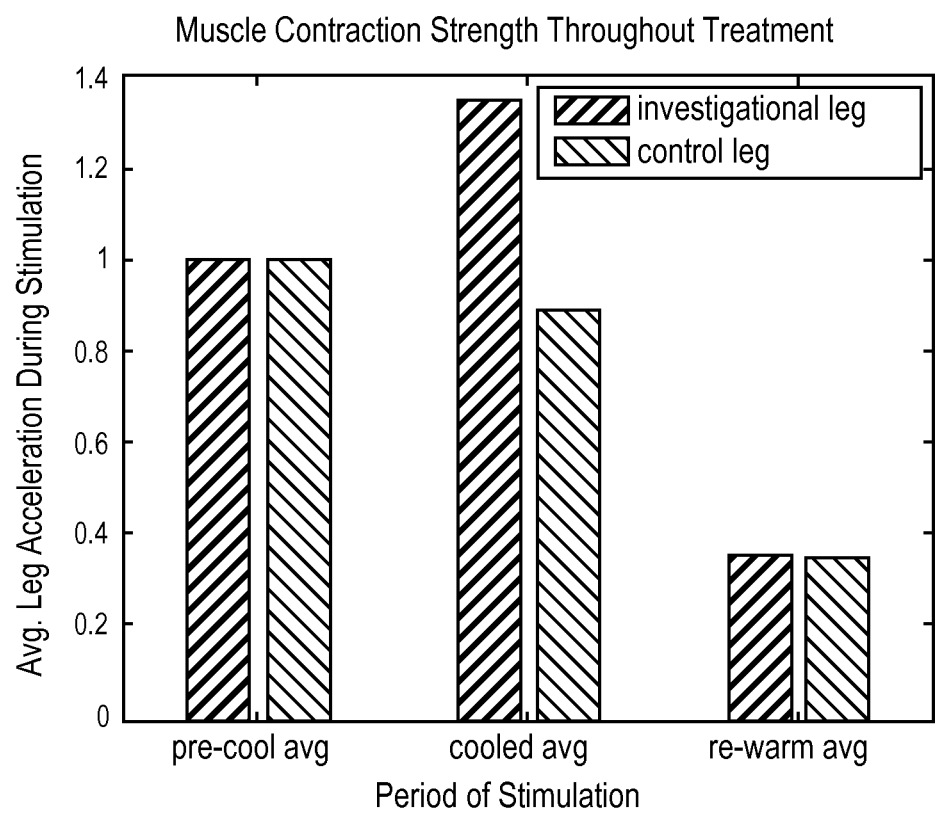
FIG. 32 shows empirical muscle stimulation data from a critically ill patient.

FIG. 32 shows empirical muscle stimulation data from a critically ill patient, which is part of the preliminary results from the second study. During stimulation, accelerometers placed on the patient's legs measured movement during stimulation of the quadriceps muscles. The amount of movement recorded is an adequate proxy for the degree to which a given amount of energy produces muscle contraction. After a series of baseline measurements acquired with both legs at body temperature were made (the set of columns on the far left), a temperature gradient was induced superficially on one leg with an ice bag while the other leg remained the body-temperature control. As shown by the center set of columns, muscle contraction strength improved during time periods when thermal stimuli were applied to the investigational leg but declined in the control leg. The decline in the control leg was likely due to fatigue. Relative to the control leg, muscle contraction was improved by 46%. Following the period of cooling, additional measurements were taken while the investigational leg was in the process of re-warming. As shown in the set of columns on the far right, contraction strength in both legs is once again similar, and dramatically less than at baseline. The decrease is again likely due to fatigue. The same energy was applied to both legs of the patient during pre-cooling, tissue cooling, and post-cool re-warming periods.

The disclosure herein generally describes muscle stimulation with an applied energy guidance field, but as set forth above the systems and device need not be used explicitly in this regard. In the embodiments herein the energy guidance field alters the electrical impedance in surface tissues and tissue proximate thereto. While one mechanism to generate the energy the guidance field is cooling the skin, other mechanisms may be used. For example, any of the following can theoretically be used, alone or in combination with other mechanisms, to generate the energy guidance field: 1) pulses or static electromagnetic fields, or magnet-based approaches in general; 2) applying a chemical agent topically or injecting a chemical agent to change conductive properties of local superficial tissues; 3) selective regional vasodilation (i.e., controlling how much blood vessels are constricted); 4) multiple energy source interference patterns to set up pathways of optimal transmission; and 5) injection of a temporary solution or material at depth to reduce the impedance of deep tissue.

The devices and methods described herein can be configured to be used on tissue surfaces inside the body as opposed to skin surfaces. In one example embodiment, surface electrodes are configured to stimulate the heart with trans-esophageal access. By applying a surface cooling device to the esophagus in a location between active stimulation electrodes, the efficiency of energy transfer to the heart may be improved. In one implementation of this embodiment, the cooling element is a compact pad with a hollow lumen, with a chilled fluid circulating through the lumen by way of small-sized inflow and outflow tubes. A variation of this embodiment with a slightly different configuration can be used in the application of diaphragmatic stimulation.

The methods described herein can be utilized effectively with any of the embodiments or variations of the devices and systems described above, as well as with other embodiments and variations not described explicitly in this document. The features of any of the systems or system components described in any of the embodiments herein can be used in any other suitable embodiment of a system or system component.

Various aspects of the disclosure described herein may be applied to any of the particular applications set forth below or for any other types of electrical stimulation and sensing systems or methods. The disclosure may be applied as a standalone system or method, or as part of an integrated medical treatment system. It shall be understood that different aspects of the disclosure can be appreciated individually, collectively, or in combination with each other.

The NMES system may be applied to any anatomical region of a subject, which may include a quadriceps region, or any other leg region. The NMES system may also be applicable to other anatomical regions as well. For example, the NMES system may target muscle tissue provided in the calves. In another example, the NMES system may target muscle tissue in the upper or lower arms. The NMES system may also target muscle tissue in the torso of a subject. For example, the system may provide stimulation to a subject's waist, or may provide stimulation to the subject's upper torso, and may use anatomical features such as armpits as a guide. The NMES system may target any other muscle tissue in a subject's body.

Any of the devices, systems, and methods described herein may incorporate suitable aspects, features, or steps used in other NMES applications. For example, the disclosure of U.S. patent application Ser. No. 12/497,230 filed Jul. 2, 2009 is hereby incorporated by reference in its entirety.

It should be understood from the foregoing that, while particular implementations have been illustrated and described, various modifications can be made thereto and are contemplated herein. It is also not intended that the disclosure be limited by the specific examples provided within the specification. Furthermore, it shall be understood that all aspects of the disclosure are not limited to the specific depictions, configurations or relative proportions set forth herein which depend upon a variety of conditions and variables. Various modifications in form and detail of the embodiments of the disclosure will be apparent to a person skilled in the art. It is therefore contemplated that the disclosure shall also cover any such modifications, variations and equivalents.

The invention claimed is:

1. A muscle stimulation system, comprising:
 a muscle stimulation pad comprising a substrate, a plurality of muscle stimulating electrodes positioned in a predetermined orientation with respect to the substrate, and a thermal region that has a reduced barrier to thermal conductivity,
 a thermal component adapted to interface with the muscle stimulation pad,
 the pad adapted to be positioned on a subject such that the plurality of muscle stimulating electrodes are disposed proximate a muscle to be stimulated and such that the thermal component is positioned to change the temperature of tissue proximate the plurality of stimulation electrodes,
 a muscle stimulation control unit adapted to be in communication with the muscle stimulation pad, the muscle stimulation control unit configured to deliver stimulating energy to the plurality of electrodes to stimulate the contraction of muscle tissue.

2. The system of claim 1 wherein the thermal region comprises a discontinuity in the substrate.

3. The system of claim 1 wherein the thermal region is a window in the pad.

4. The system of claim 3 wherein the window has a material therein that is more thermally conductive than the substrate.

5. The system of claim 4 wherein the material is a thermally-conductive hydrogel.

6. The system of claim 1 wherein the thermal region is a region of the pad configured to insulates the skin less than other sections of the pad.

7. The system of claim 1 wherein the thickness of the thermal region measured from a top surface of the pad to a bottom surface of the pad is less than a thickness of the pad outside of the thermal region.

8. The system of claim 1 wherein the thermal device overlaps with the entire surface area of the plurality of stimulating electrodes.

9. The system of claim 1 wherein the thermal device overlaps with a portion of the surface area of the plurality of stimulating electrodes.

10. A muscle stimulation system, comprising:
 a muscle stimulation control unit;
 a plurality of muscle stimulation electrodes in communication with the muscle stimulation control unit, the plurality of muscle stimulation electrodes adapted to be positioned on a subject proximate to a muscle tissue, the muscle stimulation control unit configured to deliver stimulating energy to the plurality of muscle stimulation electrodes to stimulate the contraction of muscle tissue; and a thermal device that is in at least one of electrical and mechanical communication with the muscle stimulation control unit, at least one thermal element, the thermal device adapted to modulate the temperature of the at least one thermal element to change the temperature of tissue proximate the plurality of muscle stimulation electrodes.

11. The system of claim 10 wherein the thermal device is not an integral part of or attached to any of the plurality of stimulation electrodes.

12. The system of claim 10 wherein the muscle stimulation control unit is attached to the thermal device.

13. The system of claim 10 wherein the muscle stimulation control unit comprises a housing, and wherein the thermal device is integrated within the housing.

14. The system of claim 10 wherein the thermal device comprises at least one thermal device receiving element configured to receive and secure a thermal element therein.

15. The system of claim 10 wherein the thermal device is adapted to independently control the temperature of more than one thermal element.

16. The system of claim 10 further comprising a muscle stimulation pad comprising the plurality of muscle stimulation electrodes, the pad further configured to integrate with the at least one thermal element so that the at least one thermal element is configured to change the temperature of tissue proximate the plurality of muscle stimulation electrodes.

\* \* \* \* \*